United States Patent
Che et al.

(10) Patent No.: US 12,098,126 B2
(45) Date of Patent: Sep. 24, 2024

(54) METHODS OF IRON CATALYZED C-H BOND AMINATION

(71) Applicants: Versitech Limited, Hong Kong (CN); Laboratory for Synthetic Chemistry and Chemical Biology Limited, Hong Kong (CN)

(72) Inventors: Chi-Ming Che, Hong Kong (CN); Tingjie You, Hong Kong (CN)

(73) Assignees: VERSITECH LIMITED, Hong Kong (CN); LABORATORY FOR SYNTHETIC CHEMISTRY AND CHEMICAL BIOLOGY LIMITED, Hong Kong (CN)

( * ) Notice: Subject to any disclaimer, the term of this patent is extended or adjusted under 35 U.S.C. 154(b) by 4 days.

(21) Appl. No.: 17/821,314

(22) Filed: Aug. 22, 2022

(65) Prior Publication Data

US 2023/0121302 A1    Apr. 20, 2023

Related U.S. Application Data

(60) Provisional application No. 63/236,050, filed on Aug. 23, 2021.

(51) Int. Cl.
*C07D 207/06* (2006.01)
*B01J 31/22* (2006.01)
(Continued)

(52) U.S. Cl.
CPC ........ *C07D 207/06* (2013.01); *B01J 31/2295* (2013.01); *C07D 207/12* (2013.01);
(Continued)

(58) Field of Classification Search
CPC .. C07D 207/06; C07D 207/12; C07D 207/14; C07D 217/26; C07D 221/22; C07D 223/18; C07D 233/32; C07D 401/04; C07D 403/10; C07D 405/04; C07D 417/04; C07D 471/04; C07D 487/04; B01J 31/2295
See application file for complete search history.

(56) References Cited

U.S. PATENT DOCUMENTS

2020/0079799 A1    3/2020    Negishi

FOREIGN PATENT DOCUMENTS

| WO | 2005120479 | 12/2005 |
| WO | 2014079709 | 5/2014 |

OTHER PUBLICATIONS

Berhal; Organic Letters 2012, 14, 3308-3311, with supporting information, 70 pages. https://doi.org/10.1021/ol301281s (Year: 2012).*

(Continued)

*Primary Examiner* — Clinton A Brooks
*Assistant Examiner* — Kyle Nottingham
(74) *Attorney, Agent, or Firm* — PABST PATENT GROUP LLP

(57) ABSTRACT

Described herein is an iron(II)-phthalocyanine catalyzed C—H bond amination of alkyl azides. The catalyst is effective to produce intramolecular amination of saturated C—H bonds in moderate to excellent yields and the methods are tolerant of a wide scope of substrates. The methods described are useful for the synthesis of natural products derivatives and for the late-stage functionalization of pharmaceuticals.

17 Claims, 1 Drawing Sheet

(51) Int. Cl.
   C07D 207/12    (2006.01)
   C07D 207/14    (2006.01)
   C07D 217/26    (2006.01)
   C07D 221/22    (2006.01)
   C07D 223/18    (2006.01)
   C07D 233/32    (2006.01)
   C07D 401/04    (2006.01)
   C07D 403/10    (2006.01)
   C07D 405/04    (2006.01)
   C07D 417/04    (2006.01)
   C07D 471/04    (2006.01)
   C07D 487/04    (2006.01)
   C07D 487/22    (2006.01)

(52) U.S. Cl.
   CPC ......... *C07D 207/14* (2013.01); *C07D 217/26* (2013.01); *C07D 221/22* (2013.01); *C07D 223/18* (2013.01); *C07D 233/32* (2013.01); *C07D 401/04* (2013.01); *C07D 403/10* (2013.01); *C07D 405/04* (2013.01); *C07D 417/04* (2013.01); *C07D 471/04* (2013.01); *C07D 487/04* (2013.01); *C07D 487/22* (2013.01)

(56) References Cited

OTHER PUBLICATIONS

Pazynina; Zhurnal Organicheskoi Khimii 1984, 20, 802-804. Abstract from CAS SciFinder, 1 page. (Year: 1984).*
"5.1: Isomers." Chemistry LibreTexts, Aug. 5, 2016, https://chem.libretexts.org/Courses/University_of_Kentucky/UK%3A_CHE_103_-_Chemistry_for_Allied_Health_(Soult)/Chapters/Chapter_5%3A_Properties_of_Compounds/5.1%3A_Isomers. (Year: 2016).*
Yu et al. "Three-Dimensional Heterocycles by Iron-Catalyzed Ring-Closing Sulfoxide Imidation." Angewandte Chemie International Edition, vol. 57, No. 37, Sep. 2018, pp. 12053-12056 (Year: 2018).*
Badiei, et al., "Copper-Nitrene Complexes in Catalytic C-H Amination", Angew. Chem. Int. Ed., 47(51):9961-9964 (2008).
Baek, "Direct Manipulation of Metal Imido Geometry: Key Principles to Enhance C-H Amination Efficacy", J. Am. Chem. Soc., 141(42): 16944-16953 (2019a).
Baek, et al., "C-H Amination Mediated by Cobalt Organoazide Adducts and the Corresponding Cobalt Nitrenoid Intermediates", J. Am. Chem. Soc., 142(25):11232-11243 (2020).
Baek, et al., "Catalytic C-H Amination Mediated by Dipyrrin Cobalt Imidos", J. Am. Chem. Soc., 141(19):7797-7806 (2019b).
Bagh, et al., "Catalytic Synthesis of N-Heterocycles via Direct C(sp3)-H Amination Using an Air-Stable Iron(III) Species with a Redox-Active Ligand", J. Am. Chem. Soc., 139(14):5117-5124 (2017).
Borges, et al., "Stereoselective biotransformations using fungi as biocatalysts", Tetrahedron: Asymmetry, 20(4):385-397 (2009).
Broere, et al., "Intramolecular redox-active ligand-to-substrate single-electron transfer: radical reactivity with a palladium(II) complex", J. Am. Chem. Soc., 136(33):11574-11577 (2014).
Broere, et al., "Reversible Redox Chemistry and Catalytic C(sp(3))-H Amination Reactivity of a Paramagnetic Pd Complex Bearing a Redox-Active o-Aminophenol-Derived NNO Pincer Ligand", Inorg. Chem., 55(17):8603-8611 (2016).
Chen, et al., "Rapid and Efficient Copper-Catalyzed Finkelstein Reaction of (Hetero)Aromatics under Continuous-Flow Conditions", Angew. Chem. Int. Ed., 54(1):263-266 (2015).
Coppola, et al., "Alkylation of N -boc-1,2,3,4-tetrahydroisoquinolines in the 1-position and its application to the synthesis of isoquinoline alkaloids", Journal of Heterocyclic Chemistry, 28(7):1769-1772 (1991).

Dai, et al., "Catalytic Asymmetric Synthesis of α-Arylpyrrolidines and Benzo-fused Nitrogen Heterocycles", Angew. Chem. Int. Ed., 58(11):3407-3411 (2019).
Darses, et al., "Transition metal-catalyzed iodine(iii)-mediated nitrene transfer reactions: efficient tools for challenging syntheses", Chem. Commun., 53(3):493-508 (2017).
Dong, et al., "Efficient C-H Amination Catalysis Using Nickel-Dipyrrin Complexes", J. Am. Chem. Soc., 142(25):10996-11005 (2020).
Driver, "Recent advances in transition metal-catalyzed N-atom transfer reactions of azides", Org. Biomol. Chem., 8(17):3831-3846 (2010).
Du, et al., "An Effective [Fe III (TF 4 DMAP)Cl] Catalyst for C-H Bond Amination with Aryl and Alkyl Azides", Organic Letters, 21(4):895-899 (2019a).
Du, et al., "Iron porphyrin catalysed light driven C-H bond amination and alkene aziridination with organic azides", Chem. Sci., 11(18):4680-4686 (2020).
Ercolani, et al., "Unequivocal evidence about the presence of Fe(III) in μ-oxo-bis[tetrakis(t-butyl)phthalocyaninatoiron]", J. Porphyrins Phthalocyanines, 5(9):668-673 (2001).
Fuwa, et al., "Total Synthesis of Isoindolobenzazepine Alkaloids, Lennoxamine And Chilenine, Based On Palladium-Catalyzed Reduction Of Alkenyl Phosphates", Heterocycles, 76(1):521-539 (2008).
Goddard-Borger, et al., "An Efficient, Inexpensive, and Shelf-Stable Diazotransfer Reagent: Imidazole-1-sulfonyl Azide Hydrochloride", Org. Lett., 9(19):3797-3800 (2007).
Goswami, et al., "Application of [Co(Corrole)]- Complexes in Ring-Closing C-H Amination of Aliphatic Azides via Nitrene Radical Intermediates", Eur. J. Inorg. Chem., 617-626 (2018).
Harden, et al., "Cobalt-catalyzed intermolecular C-H amination with bromamine-T as nitrene source", Chem. Commun., 44:4644-4646 (2007).
Hennessy, et al., "Complex N-heterocycle synthesis via iron-catalyzed, direct C-H bond amination", Science, 340(6132):591-595 (2013).
Intrieri, et al., "Organic azides: "energetic reagents" for the intermolecular amination of C-H bonds", Chem. Commun., 50:11440-11453 (2014).
Iovan, et al., "Diastereoselective C-H Bond Amination for Disubstituted Pyrrolidines", Angew. Chem. Int. Ed., 56:15599 (2017).
Ito, et al., "Copper(I)-Catalyzed Boryl Substitution of Unactivated Alkyl Halides", Org. Lett., 14(3):890-893 (2012).
Jakobsson, et al., "Organocatalyst-assisted Ar-18F bond formation: a universal procedure for direct aromatic radiofluorination", Chem. Commun., 53:12906 (2017).
Kawano, et al., "A new entry of amination reagents for heteroaromatic C-H bonds: copper-catalyzed direct amination of azoles with chloroamines at room temperature", J. Am. Chem. Soc., 132(20):6900-6901 (2010).
Kuijpers, et al., "Cobalt-Porphyrin-Catalysed Intramolecular Ring-Closing C-H Amination of Aliphatic Azides: A Nitrene-Radical Approach to Saturated Heterocycles", Chem. Eur. J., 23:7945-7952 (2017).
Legros, et al., "New radioligands for describing the molecular pharmacology of MT1 and MT2 melatonin receptors", Int. J. Mol. Sci., 14(5):8948-8962 (2013).
Liang, et al., "Iron-Phosphine Complex-Catalyzed Intramolecular C(sp3)-H Amination of Azides", Org. Lett., 22(5):1961-1965 (2020).
Liu, et al., "Iron-catalyzed C-H amination and its application in organic synthesis", Tetrahedron, 75:130607 (2019).
Liu, et al., "Iron- and cobalt-catalyzed C(sp3)-H bond functionalization reactions and their application in organic synthesis", Chem. Soc. Rev., 49(15):5310-5358 (2020).
Liu, et al., "Stereoselectivity in N-Iminium Ion Cyclization: Development of an Efficient Synthesis of (+)-Cephalotaxine", Org. Lett., 17(18):4444-4447 (2015).
Mailyan, et al., "Cutting-Edge and Time-Honored Strategies for Stereoselective Construction of C-N Bonds in Total Synthesis", Chem. Rev., 116(7):4441-4557 (2016).
Metz, et al., "Synthesis and properties of substituted (phthalocyaninato)-iron and -cobalt compounds and their pyridine adducts", Inorganic Chemistry, 23(8):1065-1071 (1984).

(56) References Cited

OTHER PUBLICATIONS

Neu, et al., "Binuclear Iron(III) Phthalocyanine(u-Oxodimer)-Catalyzed Oxygenation of Aromatic Hydrocarbons with Iodosylbenzene Sulfate and Iodosylbenzene as the Oxidants", Adv. Synth. Catal., 351(18):3168-3174 (2009).

Nguyen, et al., "Retinoid derivative Tp80 exhibits anti-hepatitis C virus activity through restoration of GI-GPx expression", J. of Med. Virol., 89(7):1224-1234 (2016).

Plietker, et al., "Recent advances in Fe-catalyzed C-H aminations using azides as nitrene precursors", Catal. Sci. Technol., 9:4188 (2019).

Qin, et al., "Enantioselective intramolecular C-H amination of aliphatic azides by dual ruthenium and phosphine catalysis", Chem. Sci., 10(11):3202-3207 (2019).

Ruchti, et al., "Ir-catalyzed reverse prenylation of 3-substituted indoles: total synthesis of (+)- aszonalenin and (-)-brevicompanine B", J. Am. Chem. Soc., 136(48):16756 (2014).

Ruiz, et al., "An efficient entry to pyrrolo[1,2-b]isoquinolines and related systems through Parham cyclisation", Tetrahedron, 61(13):3311-3324 (2005).

Shin, et al., "Transition-metal-catalyzed C-N bond forming reactions using organic azides as the nitrogen source: a journey for the mild and versatile C-H amination", Acc. Chem. Res., 48(4):1040-1052 (2015).

Shing, et al., "N-Heterocyclic Carbene Iron(III) PorphyrinCatalyzed Intramolecular C(sp3)-H Amination of Alkyl Azides", Angew. Chem. Int. Ed., 57(37):11947-11951 (2018).

Sorokin, et al., "Bio-inspired oxidation of methane in water catalyzed by N-bridged diiron phthalocyanine complex", Chem. Commun., 22:2562-2564 (2008).

Su, et al., "Copper-Catalyzed Formation of α-Alkoxycycloalkenones from N-Tosylhydrazones", Angew. Chem. Int. Ed., 54(44):12942-12946 (2015).

Taylor, et al., "Rings in Drugs", J. Med. Chem., 57:5845-5859 (2014).

Weix, et al., "[5]HELOL Phosphite: A Helically Grooved Sensor of Remote Chirality", J. Am. Chem. Soc., 122(41):10027-10032 (2000).

Yamato, et al., "Asymmetric synthesis of 1-alkyltetrahydroisoquinolines using chiral oxazolo[2,3-a]tetrahydroisoquinolines", Tetrahedron, 46(17):5909-5920 (1990).

Yi, et al., "Redox-Neutral α-C-H Functionalization of Pyrrolidin-3-ol", Org. Lett., 20(3):668-671 (2018).

You, et al., ")-phthalocyanine-catalyzed intramolecular C(sp 3 )H amination with alkyl azides", Chemical Communications, 57(82):10711-10714 (2021).

Yus, et al., "Negishi cross-coupling with functionalised organozinc compounds prepared by lithium- zinc transmetallation", Tetrahedron Lett., 42(33):5721-5724 (2001).

Zhou, et al., "Catalytic Enantioselective Intramolecular C(sp3)-H Amination of 2-Azidoacetamides", Angew. Chem. Int. Ed., 58(4):1088-1093 (2019).

* cited by examiner

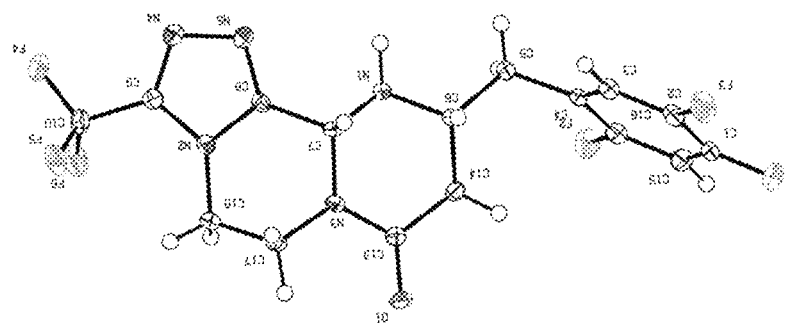
38b
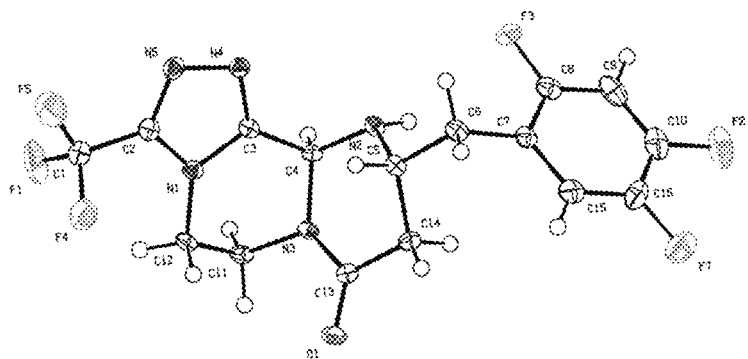
38b'

METHODS OF IRON CATALYZED C-H BOND AMINATION

CROSS-REFERENCE TO RELATED APPLICATION

This application claims the benefit of and priority to U.S. Provisional Application No. 63/236,050 filed Aug. 23, 2021, which is hereby incorporated herein by reference in its entirety.

FIELD OF THE INVENTION

The disclosed invention is generally in the field of methods of transition-metal catalyzed C—H bond aminations.

BACKGROUND OF THE INVENTION

Nitrogen-containing compounds are prevalent in bioactive molecules, natural products and pharmaceutically important molecules. Such compounds can include vesicare (solifenacin), cryptostylines I-III, norlaudanosine, tadalafil, aspidospermidine, and sitagliptin (A. K. Mailyan, et al., *Chem. Rev.*, 2016, 116, 4441. R. D. Taylor, M. MacCoss; A. D. G. Lawson, *J. Med. Chem.*, 2014, 57, 5845) It is also important to consider methods relevant to the synthesis of such compounds.

As one example, the catalytic transfer of a nitrene moiety to C—H bonds is a useful tool in direct C—H amination because it avoids pre-functionalization of starting materials and/or the use of toxic reagents. Hence, it is regarded as both time- and atom-efficient (B. Darses, et al., *Chem. Commun.*, 2017, 53, 493; Y. Liu, et al., *Chem. Soc. Rev.*, 2020, 49, 5310; Y. Liu, et al., *Tetrahedron*, 2019, 75, 130607). Over the past years, nitrene sources involved in this transformation have been used and explored including iminoiodinane (PhI=NTs, etc.) (B. Darses, et al., *Chem. Commun.* 2017, 53, 493), oxidative amide salts (such as bromamine-T, chloramine-T, etc.) (J. D. Harden, et al., *Chem. Commun.*, 2007, 4644; T. Kawano, et al., *J. Am. Chem. Soc.*, 2010, 132, 6900) to the use of organic azide ($RN_3$) (Y. M. Badiei, et al., *Angew. Chem. Int. Ed.*, 2008, 47, 9961; K. Shin, et al., *Acc. Chem. Res.*, 2015, 48, 1040; D. Intrieri, et al., *Chem. Commun.*, 2014, 50, 11440; T. G. Driver, *Org. Biomol. Chem.*, 2010, 8, 3831; B. Plietker, et al., *Catal. Sci. Technol.*, 2019, 9, 4188.)

Following reports of the use of iron-dipyrrinato catalysts to realize intramolecular $C(sp^3)$—H bonds of alkyl azides by Betley and co-workers (E. T. Hennessy, et al., *Science*, 2013, 340, 591; D. A. Iovan, et al., *Angew. Chem. Int. Ed.*, 2017, 56, 15599), many types of catalysts including iron (B. Bagh, et al., *J. Am. Chem. Soc.*, 2017, 139, 5117; K.-P. Shing, et al., *Angew. Chem. Int. Ed.*, 2018, 57, 11947; Y.-D. Du, et al., *Org. Lett.*, 2019, 21, 895; Y.-D. Du, et al., *Chem. Sci.*, 2020, 11, 4680; S. Liang, et al., *Org. Lett.*, 2020, 22, 1961), cobalt (P. F. Kuijpers, et al, *Chem. Eur. J.*, 2017, 23, 7945; M. Goswami, et al, *Eur. J. Inorg. Chem.*, 2018, 2018, 617; Y. Baek, et al, *J. Am. Chem. Soc.*, 2019, 141, 7797; Y. Baek, *J. Am. Chem. Soc.*, 2019, 141, 16944; Y. Baek, et al, *J. Am. Chem. Soc.*, 2020, 142, 11232), ruthenium (J. Qin, et al, *Chem. Sci.*, 2019, 10, 3202; Z. Zhou, et al, *Angew. Chem. Int. Ed.*, 2019, 58, 1088), nickel (Y. Dong, et al, *J. Am. Chem. Soc.*, 2020, 142, 10996), and palladium-based (D. L. J. Broere, et al, *J. Am. Chem. Soc.*, 2014, 136, 11574; D. L. J. Broere, et al, *Inorg. Chem.*, 2016, 55, 8603) catalysts have been extensively investigated. However, among the catalytic systems reported, the catalyst loadings remain high and use towards natural products synthesis has been lacking in general.

Accordingly, there remains a need for improved methods for achieving intramolecular $C(sp^3)$-H bonds of alkyl azides that require lower catalyst loadings, are applicable to a broad scope of substrates, and which are useful for producing natural product derivatives and late-stage functionalization of active pharmaceutical ingredients.

Therefore, it is an object of the present invention to provide such improved methods of catalyzed C—H bond amination.

It is a further object of the present invention to provide methods that function at lower catalyst loadings.

It is still a further object of the present invention to apply such methods towards the syntheses of natural product derivatives and late-stage functionalization of active pharmaceutical ingredients.

SUMMARY OF THE INVENTION

Methods of C—H amination are disclosed herein. The methods include the steps of:

(a) forming a reaction mixture comprising an alkyl azide, an iron(II)-phthalocyanine catalyst, and one or more solvents in a reaction vessel; and (b) heating the reaction mixture to a temperature of at least about 100° C. sufficient to induce a direct intramolecular C—H bond amination of the alkyl azide.

The product of the direct intramolecular C—H bond amination of the alkyl azide is considered a ring-closure amination product of the alkyl azide. It is believed that the methods described involve transition-metal catalyzed direct C—H bond amination proceeding via a nitrene transfer reaction to produce C—N bonds.

In some instances, the iron(II)-phthalocyanine catalyst has a chemical structure according to any one of Formulae A-D, shown below:

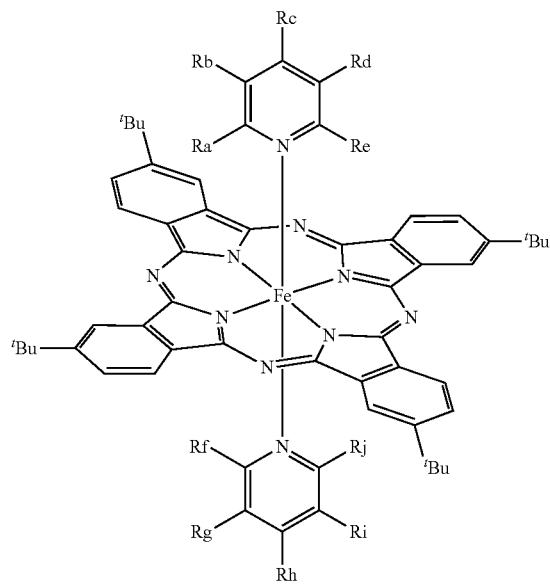

Formula A

Formula B

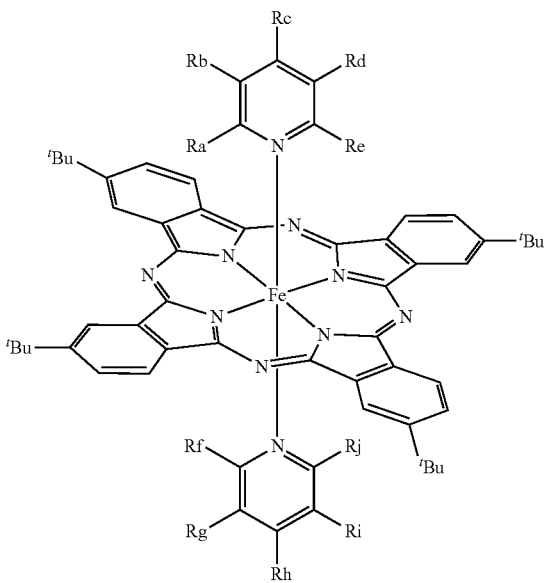

Formula D

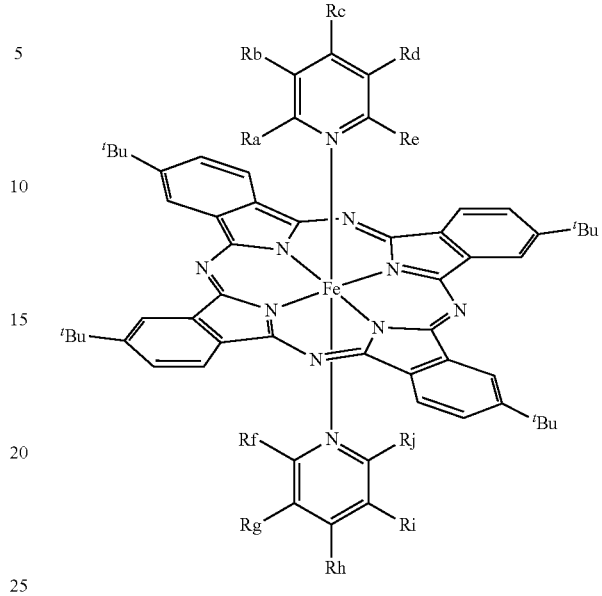

wherein Ra, Rb, Rc, Rd, Re, Rf, Rg, Rh, Ri, and Rj in each of Formulae A-D are each independently selected from the group consisting of a hydrogen; halogen group (i.e., —F, —Cl, —Br, —I); a $C_2$-$C_5$ alkyl group (linear or branched), such as a methyl, ethyl, propyl, butyl, or pentyl group; alkenyl group; alkynyl group; cycloalkyl group; cycloalkenyl group; cycloalkynyl group; a hydroxyl group; an alkoxy group, such as methoxy, ethoxy, propoxy, or butoxy; an aryl group (i.e., a phenyl group); a heteroaryl group; a benzyl group; an acyl group; an ester group; a carbonyl group; a carboxylate group; an amino group (primary, secondary, or tertiary); an amide group; and a nitro group. In some instances, the Ra, Rb, Rd, Re, Rf, Rg, Ri, and Rj are hydrogens and Rc and Rh are substituted, preferably with the same substituent. In some instances, Ra and Rb, Rb and Rc, Rc and Rd, or Rd and Re can together form a saturated, unsaturated, or aromatic, optionally substituted ring having a total of from 5 to 10 carbon atoms. In some instances, Rf and Rg, Rg and Rh, Rh and Ri, or Ri and Rj can together form a saturated, unsaturated, or aromatic, optionally substituted ring having a total of from 5 to 10 carbon atoms. In some instances, at least one of Ra, Rb, Rc, Rd, Re and at least one of Rf, Rg, Rh, Ri, and Rj are substituted.

In some instances, the iron(II)-phthalocyanine catalyst of Formula A is preferably:

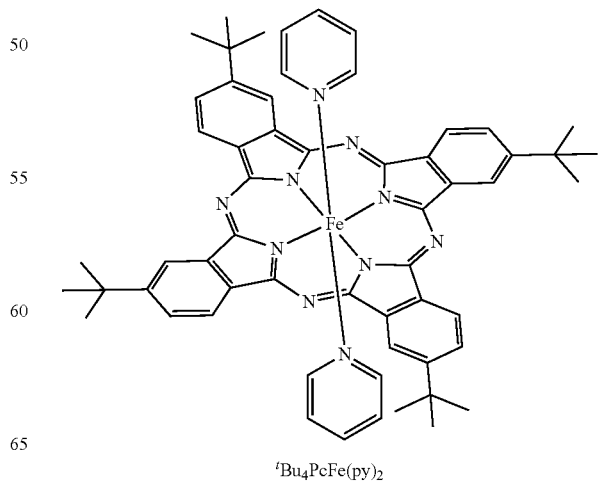

$^tBu_4PcFe(py)_2$

Formula C

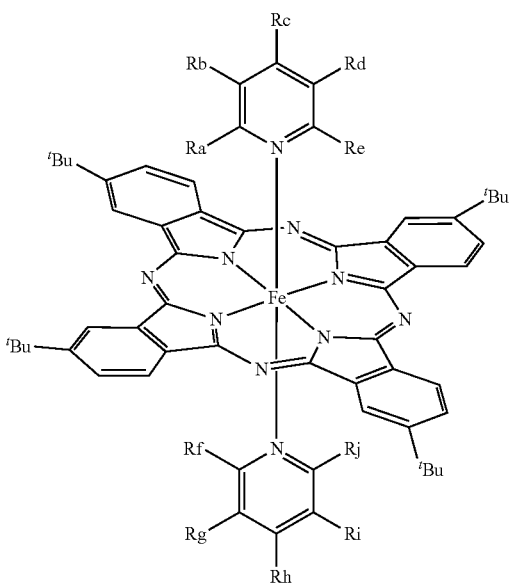

In step (b), the reaction mixture is heated to a temperature of at least about 100° C. sufficient to induce a direct intramolecular C—H bond amination of the alkyl azide. In some instances, the temperature of the reaction mixture is selected to be sufficient to cause reflux of the one or more solvents selected. In some cases, the reaction mixture is heated to a temperature of about 105° C., 110° C., 115° C., 120° C., 125° C., or 130° C. In some other cases, the reaction mixture is heated to a temperature in a range of between about 105° C. to about 130° C. The heating in step (b) can be performed for period of time ranging from between about 0.1 hour to 72 hours, 0.1 hour to 48 hours, or 0.1 hour to 24 hours. In some instances, the heating of step (b) can be performed for period of time of at least about 10, 15, 20, 25, 30, 35, 40, 45, or 50 hours.

In some instances, the alkyl azide used in the method preferably contains a benzylic, tertiary, secondary, or primary C—H bond. In some other instances, the alkyl azide has a chemical structure of Formula I, as follows:

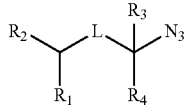

Formula I wherein $R_1$, $R_2$, $R_3$, and $R_4$ are each independently selected from the group consisting of hydrogen; halogen group (i.e., —F, —Cl, —Br, —I); a $C_2$-$C_5$ alkyl group (linear or branched), such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group (i.e., a phenyl group); a heteroaryl group; a benzyl group; an oxo (=O) group; an acyl group; an ester group; a carbonyl group; a carboxylate group; an amino group; an amide group; and a nitro group; and wherein L is a substituted or unsubstituted alkyl radical chain having 3, 4, 5, 6, 7, or 8 carbons, the chain optionally interrupted by at least one heteroatom; and, when substituted, substituents on each of the carbons present are independently selected from the group consisting of hydrogen; halogen group (i.e., —F, —Cl, —Br, —I); a $C_2$-$C_5$ alkyl group (linear or branched), such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group (i.e., a phenyl group); a heteroaryl group; an oxo (=O) group; an acyl group; an ester group; a carbonyl group; a carboxylate group; an amino group; an amide group; and a nitro group.

In certain other instances, the alkyl azide has a chemical structure of Formula II, as follows:

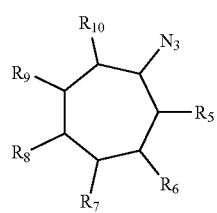

Formula II wherein $R_1$, $R_2$, $R_3$, $R_4$, $R_5$, $R_6$, $R_7$, $R_8$, $R_9$, and $R_{10}$ are each independently selected from the group consisting of hydrogen; halogen group (i.e., —F, —Cl, —Br, —I); a $C_2$-$C_5$ alkyl group (linear or branched), such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group (i.e., a phenyl group); a heteroaryl group; a benzyl group; an oxo (=O) group; an acyl group; an ester group; a carbonyl group; a carboxylate group; an amino group; an amide group; and a nitro group.

In some cases, the ring-closure amination product of the methods disclosed has a chemical structure, as shown below:

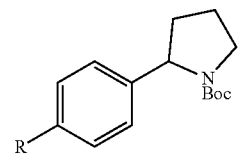

wherein R is H, Me, OMe, Cl, Br, F, $NO_2$, or N,N-dimethyl;

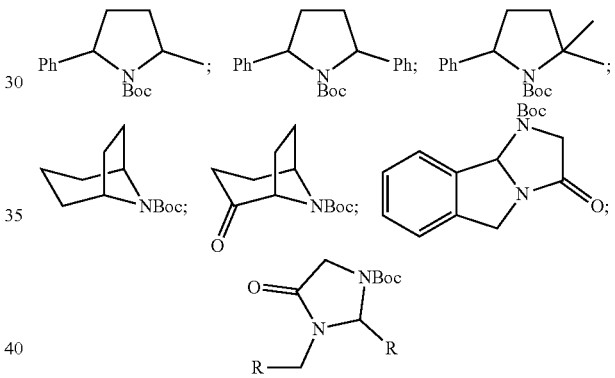

wherein each R is 4-OMeC$_6$H$_4$;

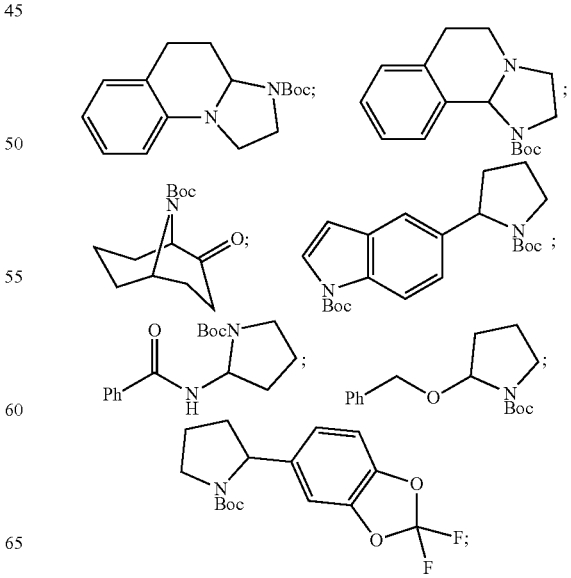

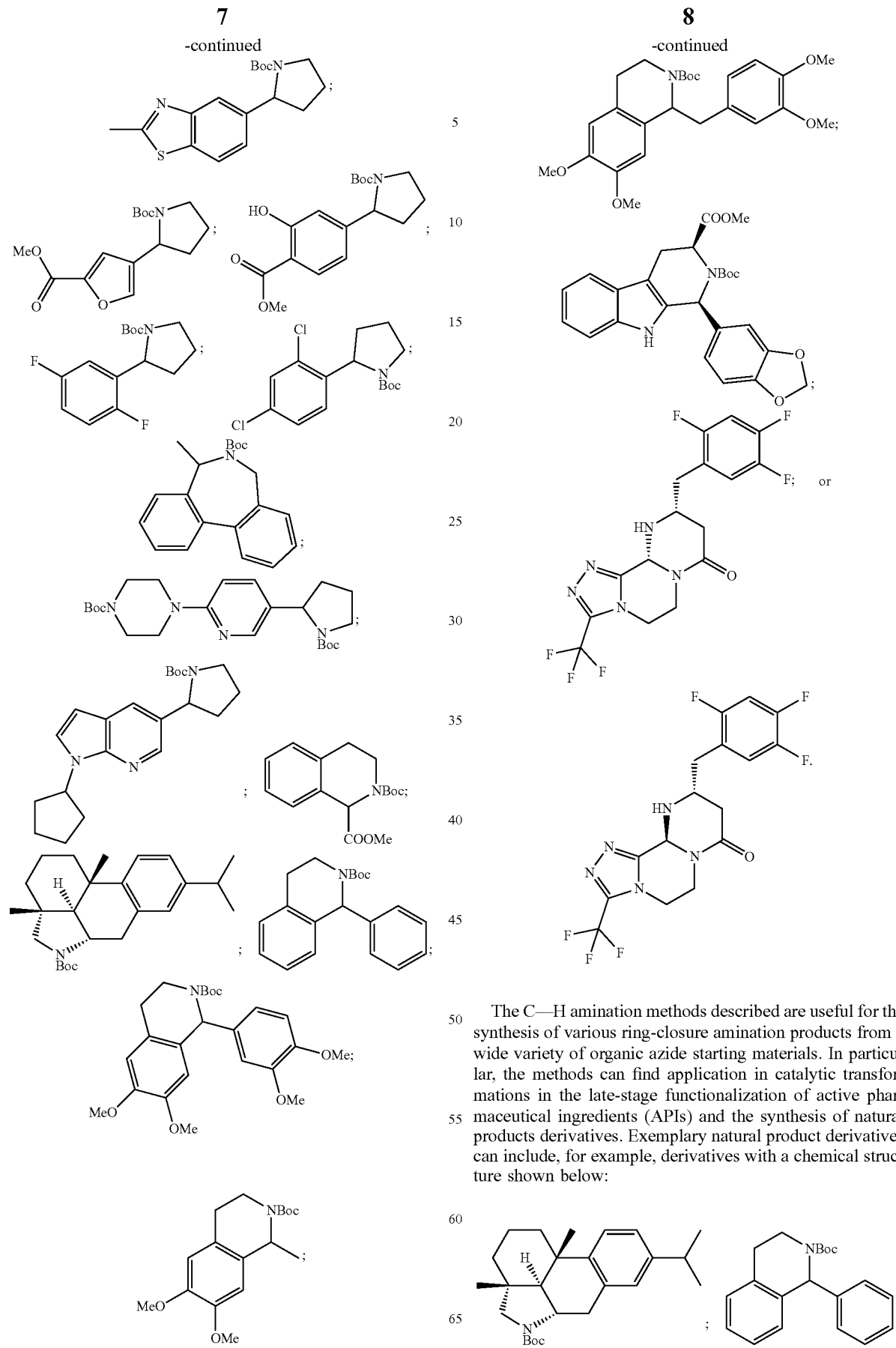

The C—H amination methods described are useful for the synthesis of various ring-closure amination products from a wide variety of organic azide starting materials. In particular, the methods can find application in catalytic transformations in the late-stage functionalization of active pharmaceutical ingredients (APIs) and the synthesis of natural products derivatives. Exemplary natural product derivatives can include, for example, derivatives with a chemical structure shown below:

-continued

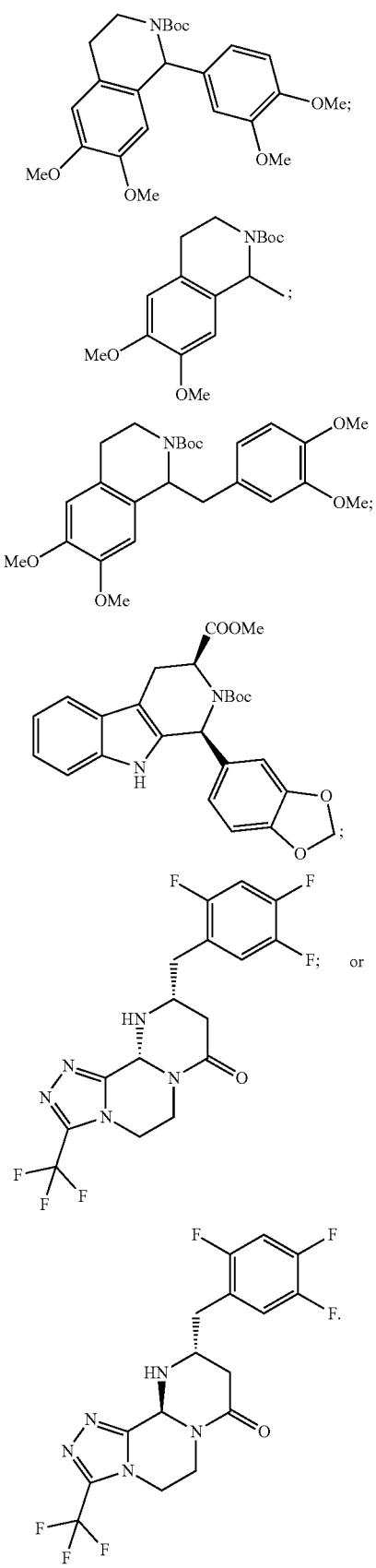

BRIEF DESCRIPTION OF THE DRAWINGS

FIG. 1 shows the x-ray crystallographic structures of sitagliptin derivatives 38b and 38b' prepared according to the C—H bond amination described in Example 4.

DETAILED DESCRIPTION OF THE INVENTION

I. Definitions

An "aryl radical" or "aryl group" is understood to mean a radical containing a structure made up of 6 to 30 carbon atoms, 6 to 18 carbon atoms, which is formed from one aromatic ring or a plurality of fused aromatic rings. Exemplary aryl radicals are, without limitation, phenyl, naphthyl, anthracenyl, or phenanthrenyl. Aryl radicals may be unsubstituted, where all carbon atoms which are substitutable bear hydrogen atoms. Alternatively, they may be substituted at one, greater than one, or at all substitutable positions therein. Suitable exemplary substituents include, without limitation, alkyl radicals, such as alkyl radicals having 1 to 8 carbon atoms, which may be selected from methyl, ethyl, i-propyl or t-butyl, aryl radicals (such as $C_6$-aryl radicals, which may be substituted or unsubstituted), heteroaryl radicals (which may comprise at least one nitrogen atom, such as pyridyl radicals), alkenyl radicals (which may comprise one double bond and 1 to 8 carbon atoms), or groups with electron donating or electron accepting ability. Groups with electron donating ability are understood to mean groups which have a positive inductive (+I) and/or positive mesomeric (+M) effect, and groups with electron accepting ability are understood to mean groups which have a negative inductive (−I) and/or negative mesomeric (−M) effect. Suitable groups with donor or acceptor action are halogen radicals, such as F, Cl, Br, alkoxy radicals, aryloxy radicals, carbonyl radicals, ester radicals, amine radicals, amide radicals, $CH_2F$ groups, $CHF_2$ groups, $CF_3$ groups, CN groups, thio groups, or SCN groups.

A "heteroaryl radical" or "heteroaryl group" is understood to mean radicals which differ from the aryl radicals described above in that at least one carbon atom in the structure making up the aryl radical is otherwise replaced by at least one heteroatom. Heteroatoms may have hydrogen substituents and/or any permissible substituents of organic compounds in order to satisfy the valences of the heteroatoms. Exemplary heteroatoms include N, O, and S. In most instances, one or two carbon atoms of the structure of the aryl radicals are replaced by heteroatoms. Exemplary heteroaryls include, without limitation, pyridyl, pyrimidyl, pyrazyl, triazyl, and five-membered heteroaromatics, such as pyrrole, furan, thiophene, pyrazole, imidazole, triazole, oxazole, thiazole. Heteroaryls may be substituted at none (unsubstituted), one, more than one, or at all substitutable positions. Suitable substituents are as defined above for the aryl radicals.

An "alkyl radical" or "alkyl group" is understood to mean a radical having 1 to 20 carbon atoms, 1 to 10 carbon atoms, or 1 to 8 carbon atoms. The alkyl radical may be branched or unbranched and the carbon chain may optionally be interrupted by one or more heteroatoms, such as N, O, or S. Heteroatoms may have hydrogen substituents and/or any permissible substituents of organic compounds in order to satisfy the valences of the heteroatoms. The alkyl radical may optionally be substituted by one or more of the substituents mentioned for the aryl radicals above. It is also possible that the alkyl radical contain one or more aryl groups thereon, where suitable aryl groups are described above. Exemplary alkyl radicals include, without limitation, methyl, ethyl, i-propyl, n-propyl, i-butyl, n-butyl, t-butyl, sec-butyl, i-pentyl, n-pentyl, sec-pentyl, neopentyl, n-hexyl, i-hexyl and sec-hexyl.

An "alkenyl radical" or "alkenyl group" is understood to mean a radical having 2 to 20 carbon atoms, 2 to 10 carbon atoms, or 2 to 8 carbon atoms, which may be optionally substituted and at least one carbon-carbon double bond.

An "alkynyl radical" or "alkynyl group" is understood to mean a radical having 2 to 20 carbon atoms, 2 to 10 carbon atoms, or 2 to 8 carbon atoms, which may be optionally substituted and at least one carbon-carbon triple bond.

A "cycloalkyl radical" or "cycloalkyl group" is understood to mean a cyclic radical having 3 to 20 carbon atoms, 3 to 10 carbon atoms, or 3 to 8 carbon atoms. The carbon chain of the cycloalkyl radical may optionally be interrupted by one or more heteroatoms, such as N, O, or S. Heteroatoms may have hydrogen substituents and/or any permissible substituents of organic compounds in order to satisfy the valences of the heteroatoms. The cycloalkyl radical may be unsubstituted or substituted, i.e. substituted by one or more of the substituents mentioned herein.

A "cycloalkenyl radical" or "alkenyl group" is understood to mean a cyclic radical having 4 to 20 carbon atoms, 4 to 10 carbon atoms, or 4 to 8 carbon atoms, which may be optionally substituted and at least one carbon-carbon double bond.

A "cycloalkynyl radical" or "cycloalkynyl group" is understood to mean a cyclic radical having 6 to 20 carbon atoms, 6 to 10 carbon atoms, or 6 to 8 carbon atoms, which may be optionally substituted and at least one carbon-carbon triple bond.

"Carbonyl group," as used herein, is understood to mean moieties which can be represented by the general formula:

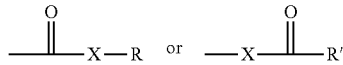

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted aryl, or substituted or unsubstituted heteroaryl, —(CH$_2$), R"; wherein R' represents a hydrogen, substituted or unsubstituted alkyl, substituted or unsubstituted alkenyl, substituted or unsubstituted alkynyl, substituted or unsubstituted cycloalkyl, substituted or unsubstituted aryl, or substituted or unsubstituted heteroaryl or —(CH$_2$)$_m$—R"; wherein R" represents a hydroxy group, substituted or unsubstituted carbonyl group, an aryl, a cycloalkyl, a heterocycle, or a polycycle; and m is zero or an integer ranging from 1 to 8. Where X is oxygen and R is defined as above, the moiety can be referred to as a "carboxyl group." When X is oxygen and R is hydrogen, the formula represents a "carboxylic acid group." Where X is oxygen and R' is hydrogen, the formula represents a "formate group." Where X is oxygen and R or R' is not hydrogen, the formula represents an "ester group." In general, where the oxygen atom of the above formula is replaced by a sulfur atom, the formula represents a "thiocarbonyl group." Where X is sulfur and R or R' is not hydrogen, the formula represents "thioester group." Where X is sulfur and R is hydrogen, the formula represents a "thiocarboxylic acid group." Where X is sulfur and R' is hydrogen, the formula represents a "thioformate group." Where X is a bond and R is not hydrogen, the above formula represents a "ketone group." Where X is a bond and R is hydrogen, the above formula represents an "aldehyde group." The term "substituted carbonyl" refers to a carbonyl, as defined above, wherein one or more hydrogen atoms in R, R' or a group to which the moiety is attached, are independently substituted with suitable substituents, as defined below.

An "amide group" or "amido" is understood to mean a moiety represented by the general formula:

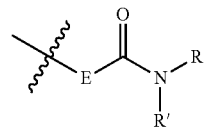

wherein, E is absent, or E is substituted or unsubstituted alkyl, substituted or unsubstituted alkenyl, substituted or unsubstituted alkynyl substituted or unsubstituted cycloalkyl, substituted or unsubstituted aryl, substituted or unsubstituted heteroaryl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R" can represent a hydroxy group, substituted or unsubstituted carbonyl group, an aryl group, a cycloalkyl group, a heterocycle, or a polycycle; and m is zero or an integer ranging from 1 to 8. When E is oxygen, a "carbamate group" is formed. The carbamate cannot be attached to another chemical species, such as to form an oxygen-oxygen bond, or other unstable bonds, as understood by one of ordinary skill in the art.

1. The term "substituted," as used herein, refers to all permissible substituents of the compounds or functional groups described above. Exemplary substituents include, but are not limited to, halogens, hydroxyl groups, or any other organic groupings containing any number of carbon atoms, preferably 1-14 carbon atoms, and optionally include one or more heteroatoms, such as oxygen, sulfur, or nitrogen grouping in linear, branched, or cyclic structural formats. Representative substituents can include alkyl, substituted alkyl (such as —CF$_3$ and —CD$_3$), alkenyl, substituted alkenyl, alkynyl, substituted alkynyl, phenyl, substituted phenyl, aryl, substituted aryl, heteroaryl, substituted heteroaryl, halo, hydroxyl, alkoxy, formyl, substituted alkoxy, phenoxy, substituted phenoxy, aroxy, substituted aroxy, thio (—SH), substituted thio, arylthio, substituted arylthio, cyano, isocyano, substituted isocyano, carbonyl, substituted carbonyl, carboxyl, substituted carboxyl, carboxylates, amino, substituted amino, amide, substituted amide, sulfonyl, substituted sulfonyl, sulfonic acid, phosphoryl, substituted phosphoryl, phosphonyl, substituted phosphonyl, polyaryl, substituted polyaryl, cyclic (such as C$_3$-C$_{20}$ cyclic), substituted cyclic (such as substituted C$_3$-C$_{20}$ cyclic), heterocyclic, substituted heterocyclic, deuterium, trihaloalkyl (trifluoromethyl), unsubstituted diarylamino, substituted diarylamino, unsubstituted dialkylamino, substituted dialkylamino, azo, carbonate ester, nitro, nitroso, phosphino, pyridyl, NRR', SR, C(O)R, COOR, C(O)NR, SOR, and SOR groups, wherein R and R are independently selected from hydrogen atom, deuterium atom, or any of the substituents named above.

Numerical ranges disclosed in the present application include, but are not limited to, ranges of carbon atoms, ranges of temperatures, ranges of concentrations, ranges of times, amongst other ranges disclosed below. The disclosed ranges, disclose individually each possible number that such a range could reasonably encompass, as well as any sub-ranges and combinations of sub-ranges encompassed therein. For example, disclosure of a range of carbon atoms is intended to disclose individually every possible value that such a range could encompass, consistent with the disclosure herein. For example, a carbon range of 1 to 10 carbons also discloses each number of carbons within the range individually (1, 2, 3, 4, 5, 6, 7, 8, 9, 10 carbons), as well as any sub-range contained therein (2 to 4 carbons or 5 to 9 carbons).

Use of the term "about" is intended to describe values either above or below the stated value, which the term "about" modifies, in a range of approx. +/−10%; in other instances the values may range in value either above or below the stated value in a range of approx. +/−5%. When the term "about" is used before a range of numbers (i.e., about 1-5) or before a series of numbers (i.e., about 1, 2, 3, 4, etc.) it is intended to modify both ends of the range of numbers and/or each of the numbers recited in the entire series, unless specified otherwise.

II. Methods of C—H Bond Amination

Methods of C—H amination are described herein. In some instances, the methods described include the following steps:
(a) forming a reaction mixture comprising an alkyl azide, an iron(II)-phthalocyanine catalyst, and one or more solvents in a reaction vessel; and
(b) heating the reaction mixture to a temperature of at least about 100° C. sufficient to induce a direct intramolecular C—H bond amination of the alkyl azide.

The product of the direct intramolecular C—H bond amination of the alkyl azide is considered a ring-closure amination product of the alkyl azide. It is believed that methods described involve transition-metal catalyzed direct C—H bond amination proceeding via a nitrene transfer reaction to produce C—N bonds.

The reaction mixture may be prepared according to standard synthetic practices known by the skilled person in any suitable reaction vessel known. The reaction mixture following step (b) can be worked up and purified using any standard synthetic workup and purification procedures known to the skilled person to obtain isolated product(s) of the direct intramolecular C—H bond amination of the alkyl azide. In some cases, steps (a) and/or (b) are performed under an inert atmosphere where the inert atmosphere can be selected from argon, nitrogen, or a combination thereof. The product of the direct intramolecular C—H bond amination of the alkyl azide can be characterized by the skilled person using any known synthetic characterization techniques (including, but not limited to, NMR, UV/Vis, mass spectrometry, elemental analysis, etc.).

The concentration of the alkyl azide present in the reaction mixture can be at any suitable concentration. In some instances, the concentration of the alkyl azide present in the reaction mixture is in a range of about 0.01 to 5M, 0.01 to 4M, 0.01 to 3M, 0.01 to 2M, or 0.01 to 1M, as well as sub-ranges within. The amount of the iron(II)-phthalocyanine catalyst present in the reaction mixture can be at an amount of about 0.1 to 5 mol % of the amount of the alkyl azide present. In some other instances, the amount of the catalyst is at least about 1, 2, 3, 4, or 5 mol % of the amount of the alkyl azide present.

In some instances, the iron(II)-phthalocyanine catalyst is diamagnetic or paramagnetic. In certain cases, the catalyst is preferably diamagnetic. In certain other cases, the catalyst is paramagnetic.

In some instances, the iron(II)-phthalocyanine catalyst has a chemical structure according to any one of Formulae A-D, shown below:

Formula A

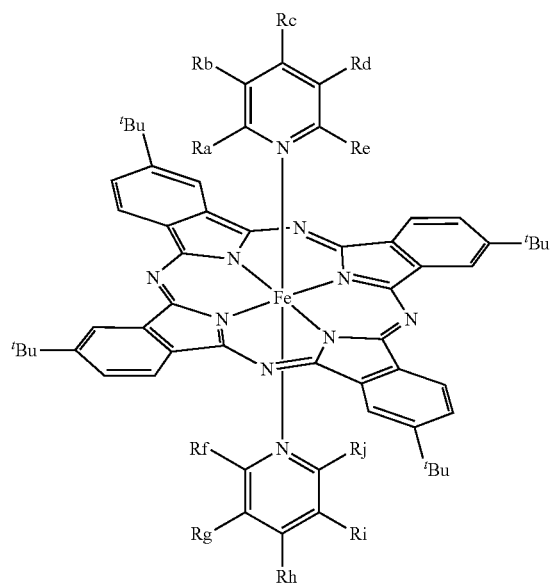

Formula B

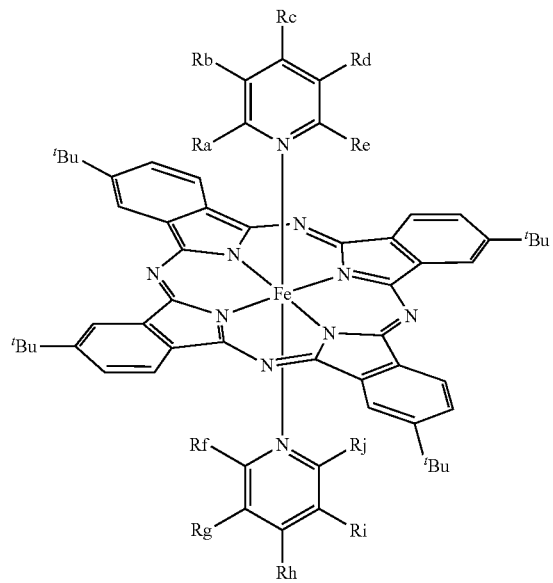

Formula C

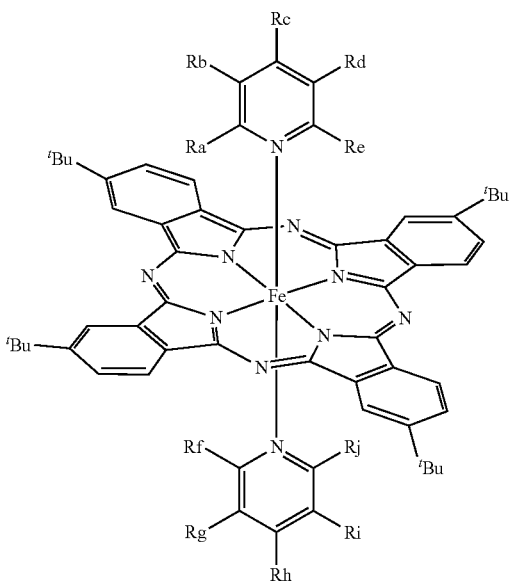

Formula D

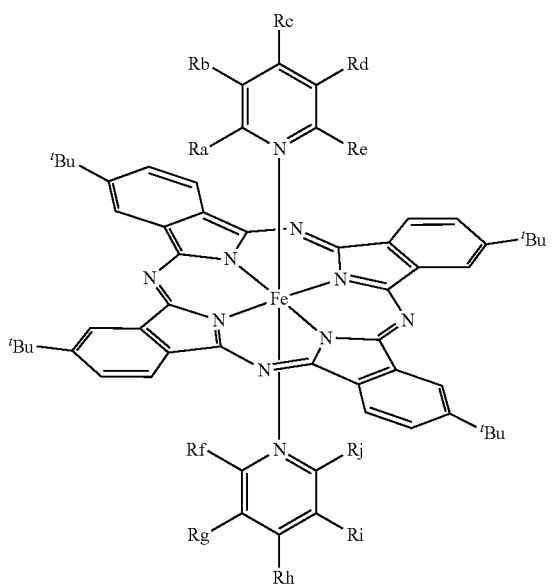

wherein Ra, Rb, Rc, Rd, Re, Rf, Rg, Rh, Ri, and Rj in each of Formulae A-D are each independently selected from the group consisting of a hydrogen; halogen group (i.e., —F, —Cl, —Br, —I); a $C_2$-$C_5$ alkyl group (linear or branched), such as a methyl, ethyl, propyl, butyl, or pentyl group; alkenyl group; alkynyl group; cycloalkyl group; cycloalkenyl group; cycloalkynyl group; a hydroxyl group; an alkoxy group, such as methoxy, ethoxy, propoxy, or butoxy; an aryl group (i.e., a phenyl group); a heteroaryl group; a benzyl group; an acyl group; an ester group; a carbonyl group; a carboxylate group; an amino group (primary, secondary, or tertiary); an amide group; and a nitro group. In some instances, the Ra, Rb, Rd, Re, Rf, Rg, Ri, and Rj are hydrogens and Rc and Rh are substituted, preferably with the same substituent. In some other instances, Ra and Rb, Rb and Rc, Rc and Rd, or Rd and Re can together form a saturated, unsaturated, or aromatic, optionally substituted ring having a total of from 5 to 10 carbon atoms. In still other instances, Rf and Rg, Rg and Rh, Rh and Ri, or Ri and Rj can together form a saturated, unsaturated, or aromatic, optionally substituted ring having a total of from 5 to 10 carbon atoms. In some instances, at least one of Ra, Rb, Rc, Rd, Re and at least one of Rf, Rg, Rh, Ri, and Rj are substituted.

The iron(II)-phthalocyanine catalyst used in the methods described includes a catalyst of any one of Formulae A-D above. In some instances, the catalyst used contains a mixture of two or more catalyst compounds of Formulae A-D. The skilled person understands that such mixtures of catalysts, such as those of Formulae A-D, and which can be considered isomers can be used in the methods. Methods of synthesizing catalysts according to any one of Formulae A-D are known in the art.

In some instances, the iron(II)-phthalocyanine catalyst of Formula A has a chemical structure as follows:

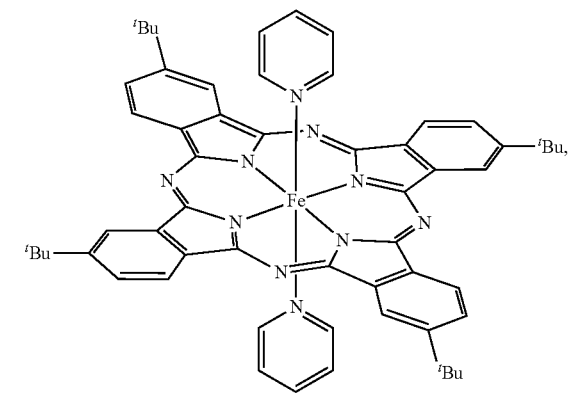

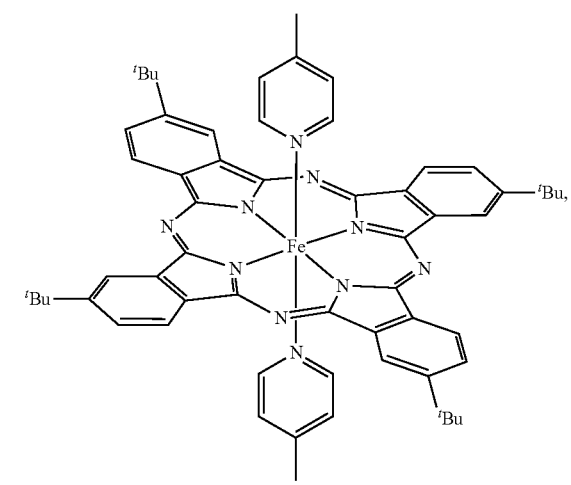

17
-continued
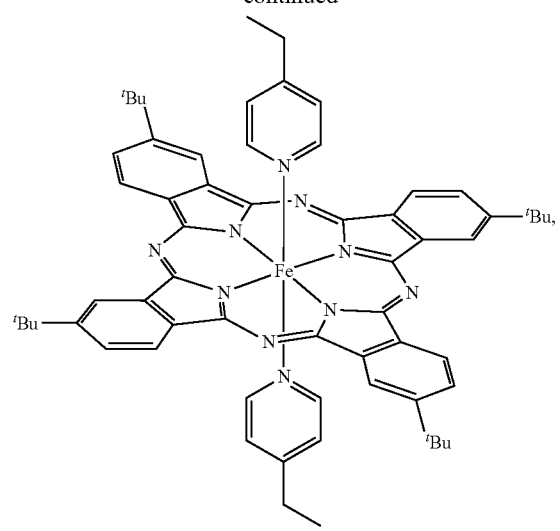
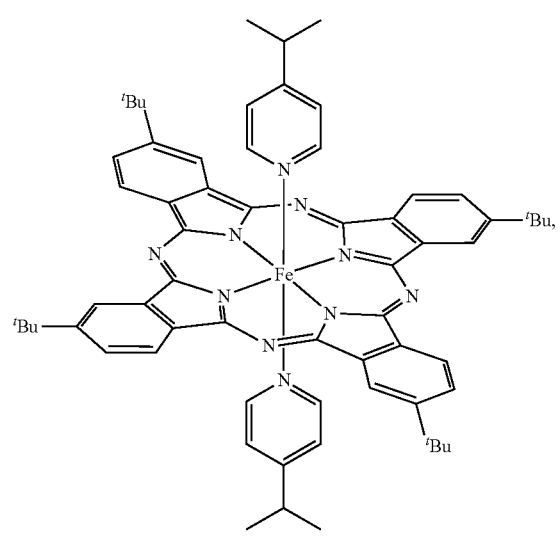
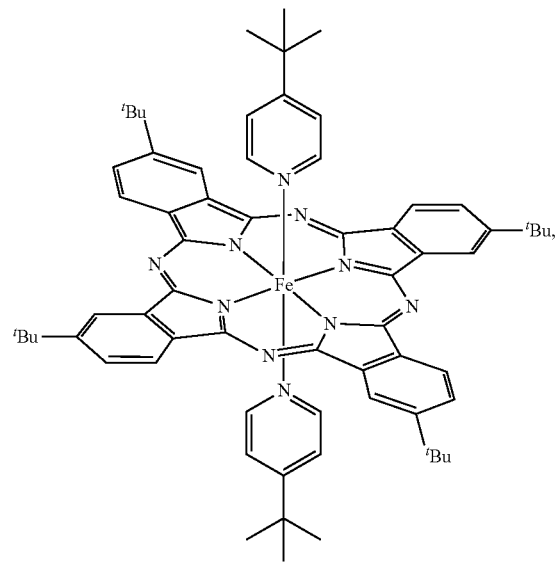
18
-continued
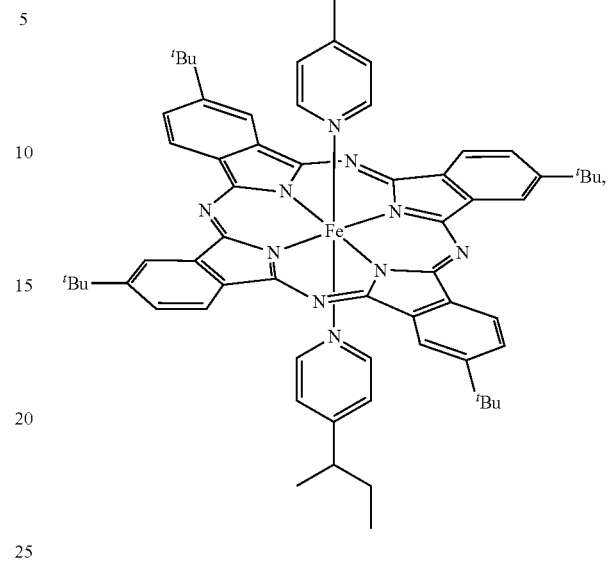
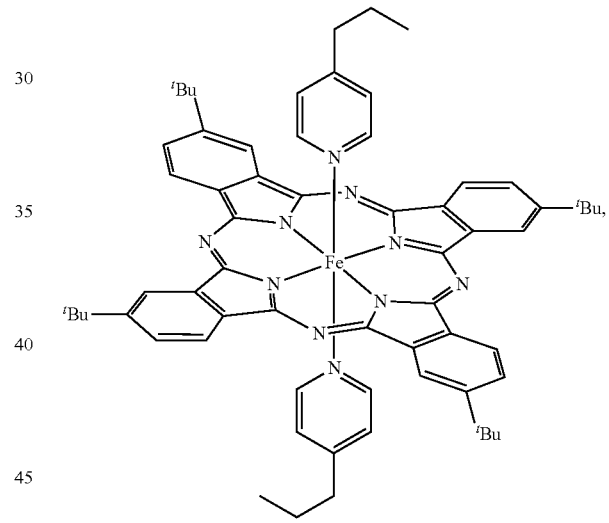
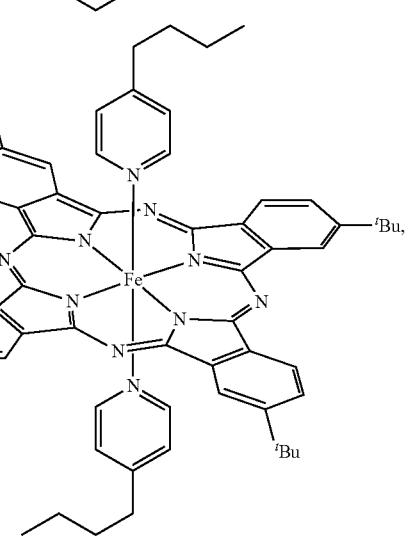

-continued
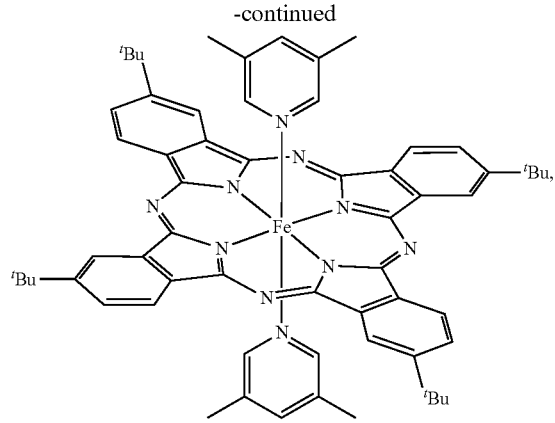
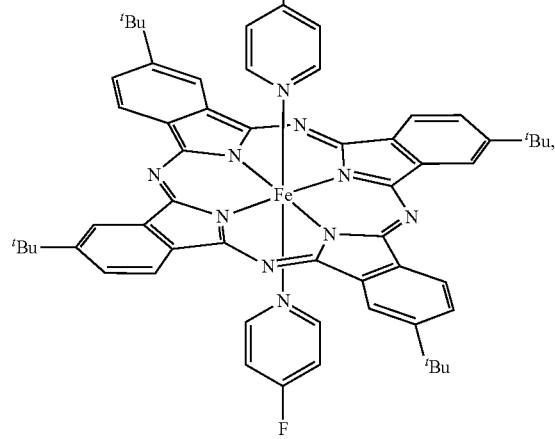
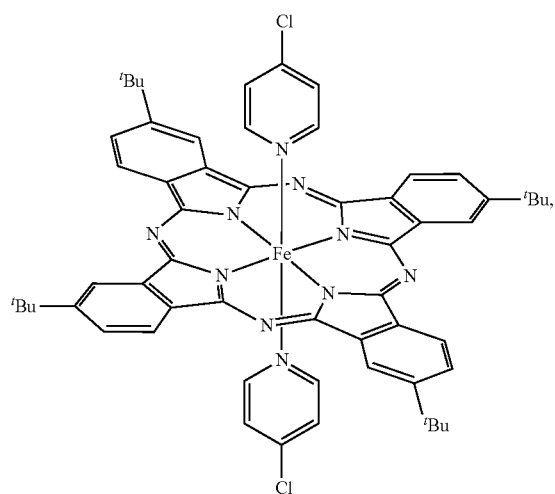
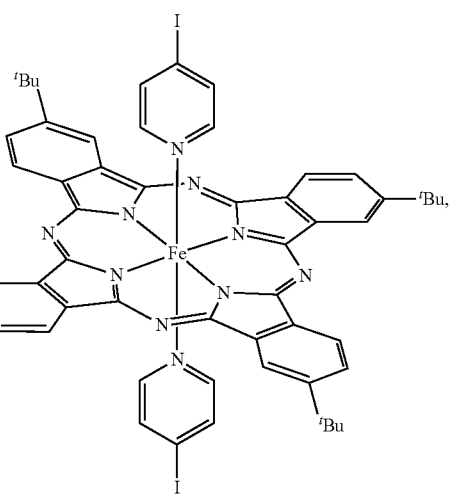
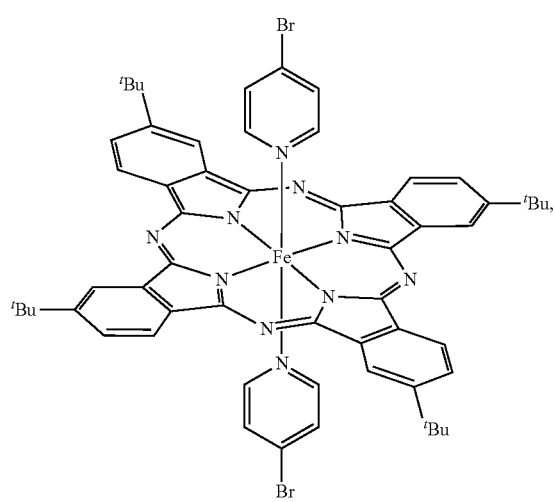
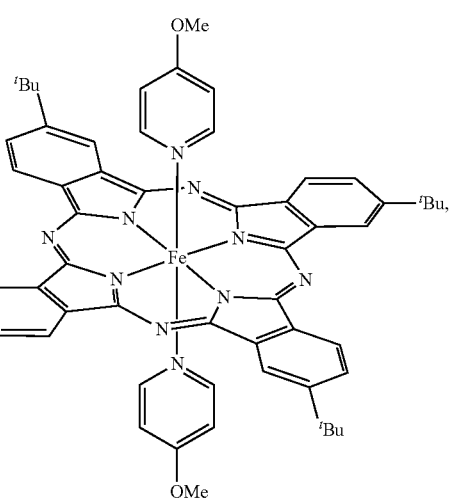

21
-continued
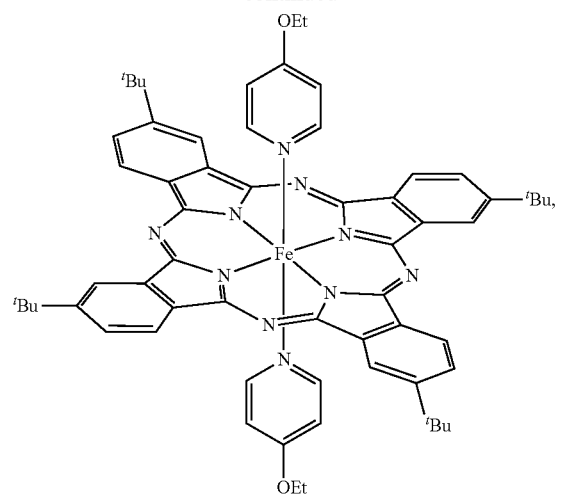
22
-continued
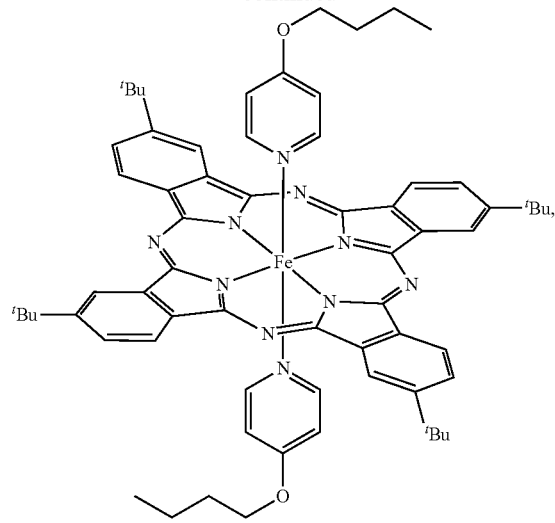
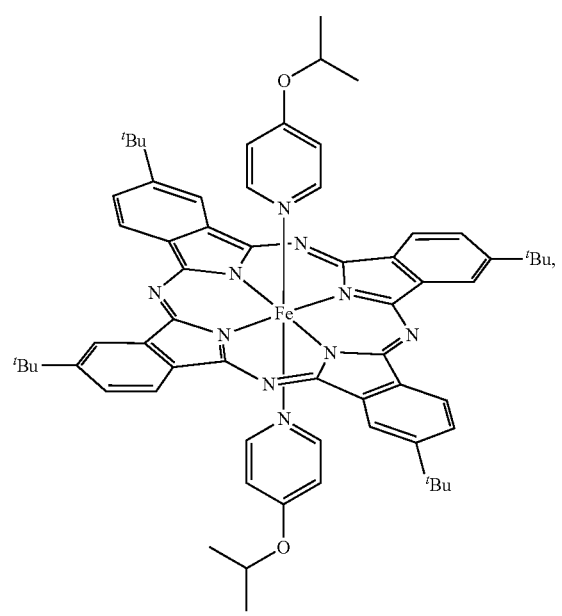
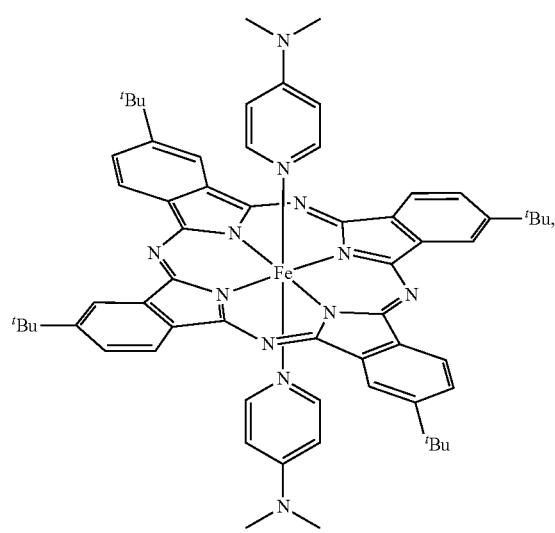
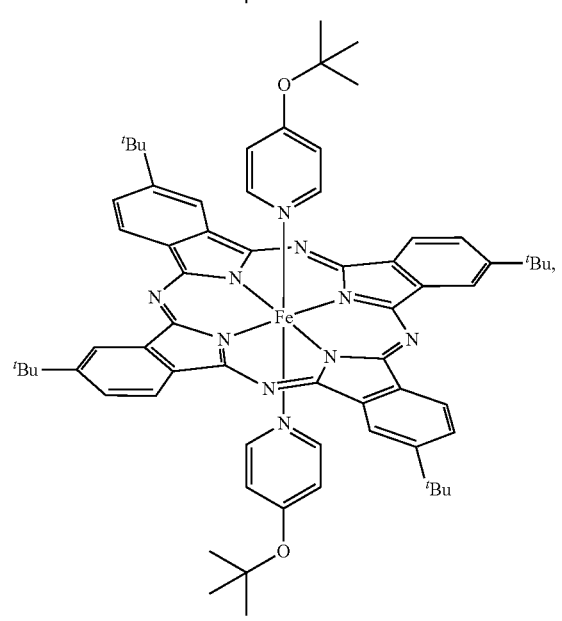
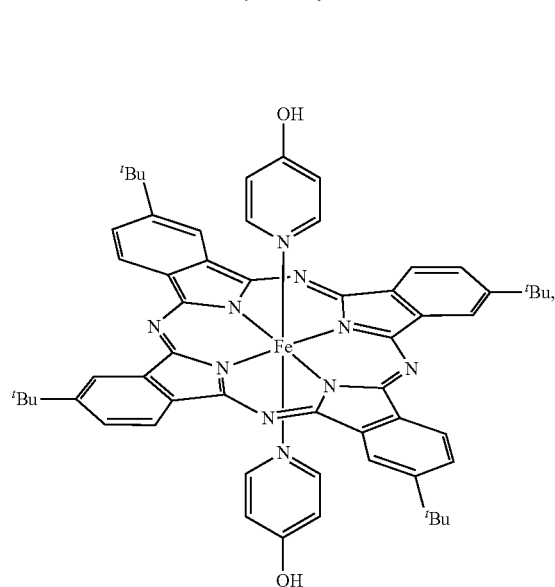

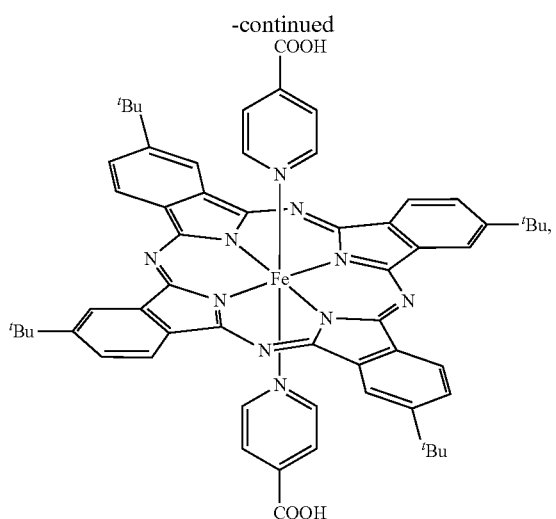

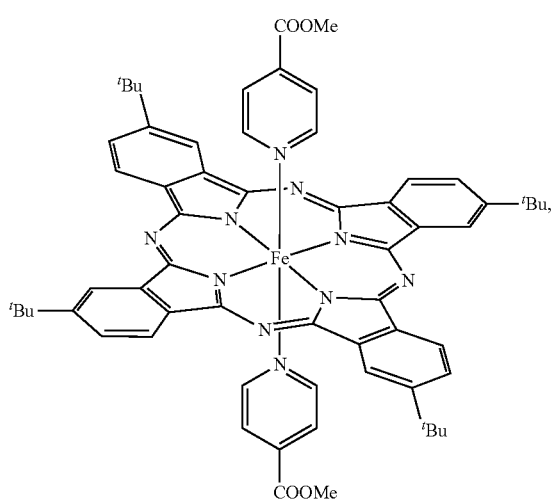

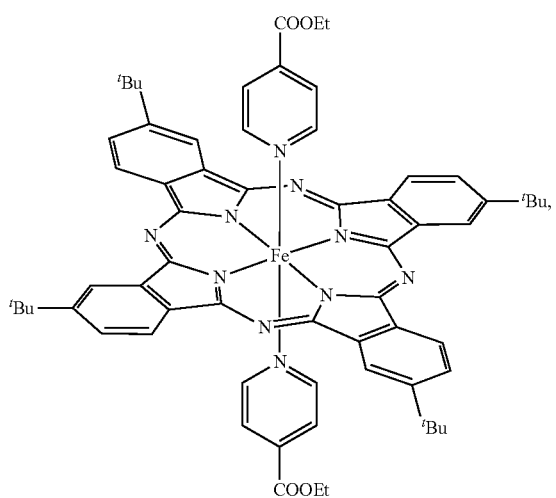

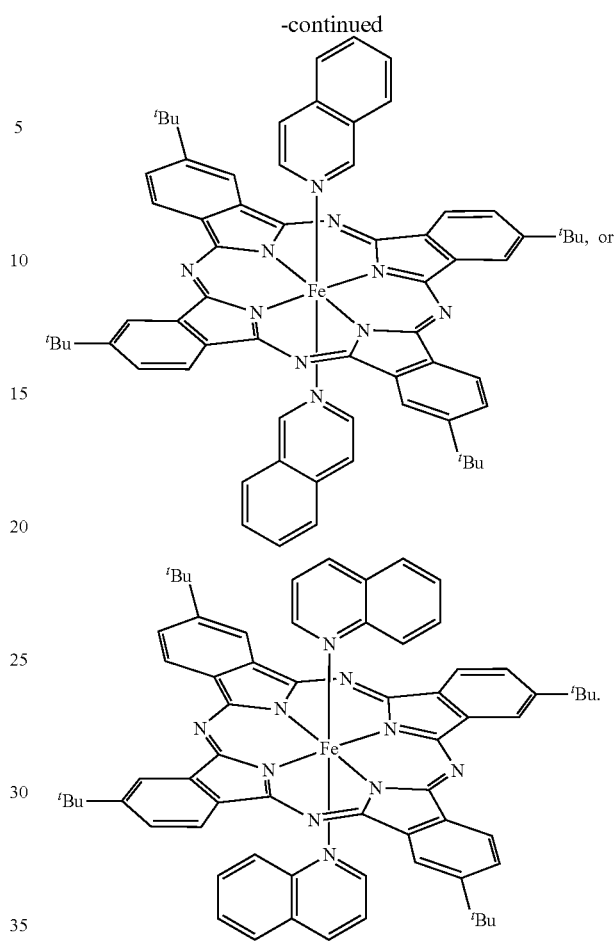

The positions of the tert-butyl groups on the phthalocyanine in the above compounds are those shown for Formula A above. The equivalent isomeric structures having the tert-butyl groups on the phthalocyanine, as shown in Formulae B-D above, are also described and disclosed, as would be recognized and understood by the person of ordinary skill in the art.

In some instances, the iron(II)-phthalocyanine catalyst of Formula A is preferably:

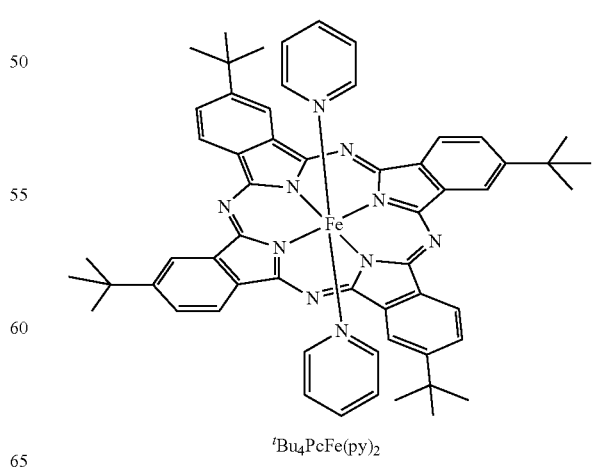

The catalyst $^tBu_4PcFe(py)_2$ is diamagnetic.

In still other instances, the iron(II)-phthalocyanine catalyst can have one of the following chemical structures:

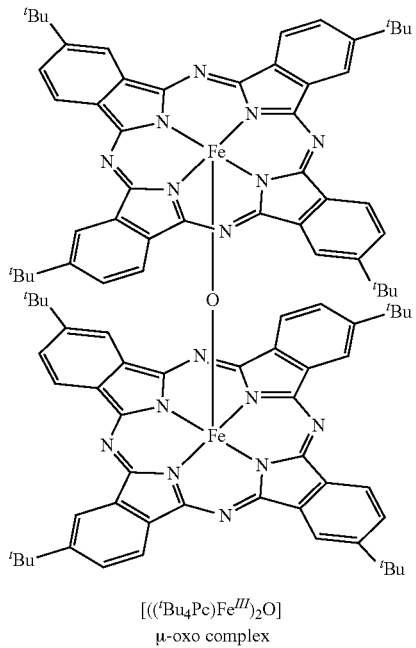

[(($^t$Bu$_4$Pc)Fe$^{III}$)$_2$O]
μ-oxo complex

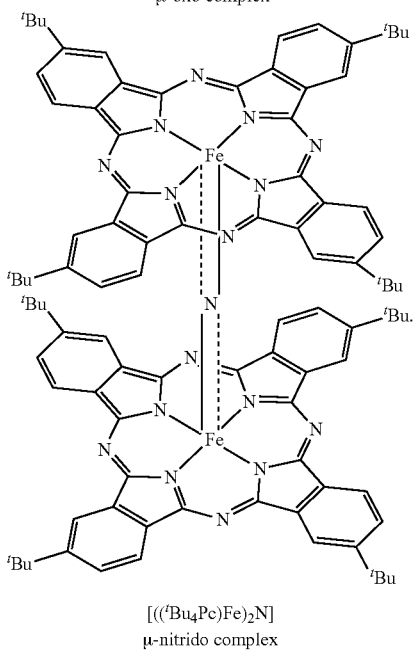

[(($^t$Bu$_4$Pc)Fe)$_2$N]
μ-nitrido complex

In some cases, the reaction mixture further contains at least one reagent for protecting amine groups. Suitable amine protecting groups are known in the art. In such instances, the reagent for protecting amine groups is present in an amount of about 1 to 3 equivalents of the molar amount of the alkyl azide present in the reaction mixture. In some instances, the reagent for protecting amine groups is fluorenylmethoxycarbonyl (Fmoc) or preferably di-tert-butyl dicarbonate (Boc$_2$O). Standard procedures for removal of protecting amine groups are known to the person of ordinary skill in the art and may be performed following the formation of direct intramolecular C—H bond amination products of the alkyl azide.

The one or more solvents in the reaction mixture can be selected from any suitable solvent(s). The volume(s) of the one or more solvents in the reaction mixture may be any suitable amount and the volume of solvent(s) needed may be readily determined by the skilled person. In some instances, the one or more solvents are organic solvents selected from the group consisting of toluene, benzene, chlorobenzene, 1,2-dichlorobenzene, 1,2-dichloroethane. Preferably the one or more solvents are used dry.

In step (b), the reaction mixture is heated to a temperature of at least about 100° C. sufficient to induce a direct intramolecular C—H bond amination of the alkyl azide. In some instances, the temperature of the reaction mixture is selected to be sufficient to cause reflux of the one or more solvents selected. In some cases, the reaction mixture is heated to a temperature of about 105° C., 110° C., 115° C., 120° C., 125° C., or 130° C. In some other cases, the reaction mixture is heated to a temperature in a range of between about 105° C. to about 130° C. The heating in step (b) can be performed for period of time ranging from between about 0.1 hour to 72 hours, 0.1 hour to 48 hours, or 0.1 hour to 24 hours. In some instances, the heating of step (b) can be performed for period of time of at least about 10, 15, 20, 25, 30, 35, 40, 45, or 50 hours.

In some instances, the alkyl azide used in the method preferably contains a benzylic, tertiary, secondary, or primary C—H bond. In some other instances, the alkyl azide has a chemical structure of Formula I, as follows:

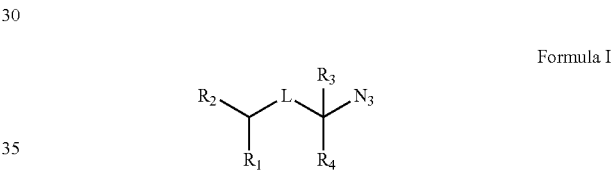

Formula I wherein $R_1$, $R_2$, $R_3$, and $R_4$ are each independently selected from the group consisting of hydrogen; halogen group (i.e., —F, —Cl, —Br, —I); a $C_2$-$C_5$ alkyl group (linear or branched), such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group (i.e., a phenyl group); a heteroaryl group; a benzyl group; an oxo (═O) group; an acyl group; an ester group; a carbonyl group; a carboxylate group; an amino group; an amide group; and a nitro group; and wherein L is a substituted or unsubstituted alkyl radical chain having 3, 4, 5, 6, 7, or 8 carbons, the chain optionally interrupted by at least one heteroatom; and, when substituted, substituents on each of the carbons present are independently selected from the group consisting of hydrogen; halogen group (i.e., —F, —Cl, —Br, —I); a $C_2$-$C_5$ alkyl group (linear or branched), such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group (i.e., a phenyl group); a heteroaryl group; an oxo (═O) group; an acyl group; an ester group; a carbonyl group; a carboxylate group; an amino group; an amide group; and a nitro group.

In some instances, the at least one heteroatom on L, when present, can be selected from an oxygen, sulfur, nitrogen atom, or combination thereof with the proviso that valency requirements of the heteroatom(s) are satisfied.

In some instances, adjacent or close carbons (i.e., separated by one or two atoms) of the substituted or unsubstituted alkyl radical chain L can together form a saturated, unsaturated, or aromatic, optionally substituted ring having a total of 5 to 10 carbon atoms.

In some instances, any one of $R_1$, $R_2$, $R_3$, and $R_4$ and a carbon of the substituted or unsubstituted alkyl radical chain L can independently together form a saturated, unsaturated, or aromatic, optionally substituted ring having a total of from 5 to 10 carbon atoms.

In some instances, $R_1$ and $R_2$ can together form a saturated, unsaturated, or aromatic, optionally substituted ring having a total of from 5 to 10 carbon atoms. In some instances, $R_3$ and $R_4$ can together form a saturated, unsaturated, or aromatic, optionally substituted ring having a total of from 5 to 10 carbon atoms. In still other instances, $R_1$ and $R_3$ or $R_4$ can be linked together by a saturated, unsaturated, optionally substituted alkyl chain having a total of from 3 to 10 carbon atoms. In yet other instances, $R_2$ and $R_3$ or $R_4$ can be linked together by a saturated, unsaturated, optionally substituted alkyl chain having a total of from 3 to 10 carbon atoms. In some instances, $R_3$ and $R_1$ or $R_2$ can be linked together by a saturated, unsaturated, optionally substituted alkyl chain having a total of from 3 to 10 carbon atoms. In still other instances, $R_4$ and $R_1$ or $R_2$ can be linked together by a saturated, unsaturated, optionally substituted alkyl chain having a total of from 3 to 10 carbon atoms.

In certain other instances, the alkyl azide has a chemical structure of Formula II, as follows:

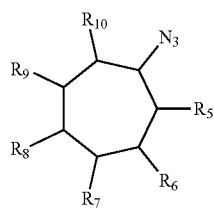

Formula II wherein $R_1$, $R_2$, $R_3$, $R_4$, $R_5$, $R_6$, $R_7$, $R_8$, $R_9$, and $R_{10}$ are each independently selected from the group consisting of hydrogen; halogen group (i.e., —F, —Cl, —Br, —I); a $C_2$-$C_5$ alkyl group (linear or branched), such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group (i.e., a phenyl group); a heteroaryl group; a benzyl group; an oxo (=O) group; an acyl group; an ester group; a carbonyl group; a carboxylate group; an amino group; an amide group; and a nitro group.

In some instances, wherein each of $R_5$ and $R_6$, $R_6$ and $R_7$, $R_7$ and $R_8$, $R_8$ and $R_9$, or $R_9$ and $R_{10}$ can optionally form a saturated, unsaturated, or aromatic, optionally substituted ring, optionally interrupted by a heteroatom, and having a total of from 5 to 18 carbon atoms and heteroatoms.

In some cases, the ring-closure amination product of the above method has a chemical structure, as shown below:

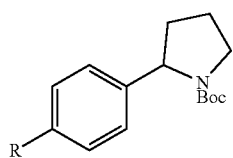

wherein R is H, Me, OMe, Cl, Br, F, $NO_2$, or N,N-dimethyl;

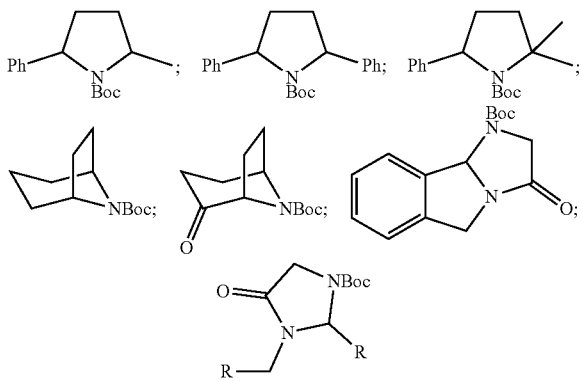

wherein each R is 4-$OMeC_6H_4$;

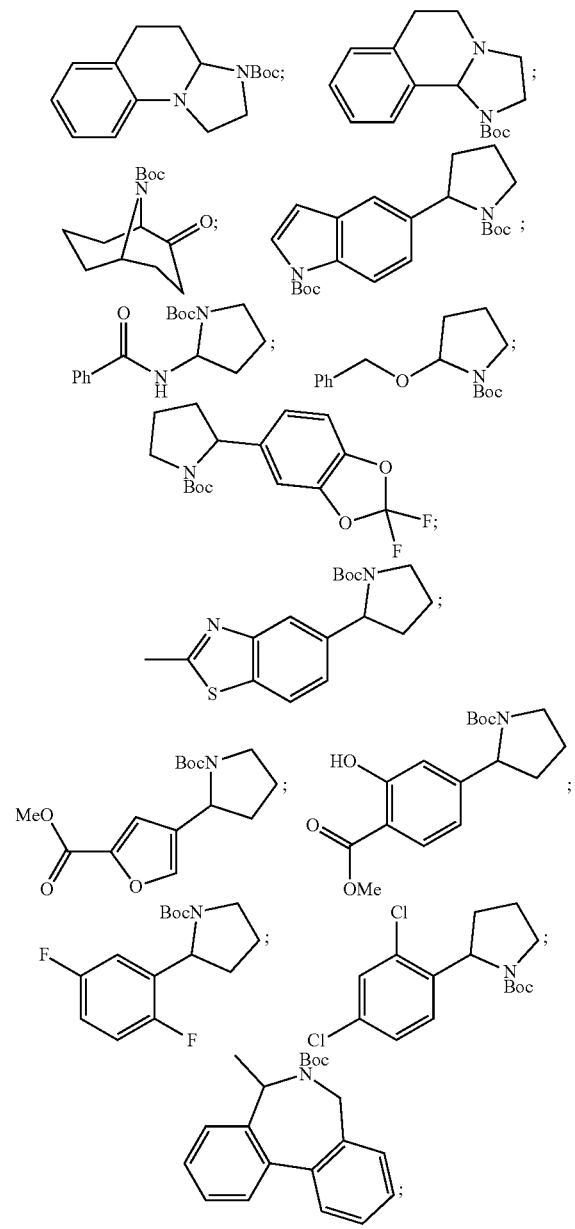

29

-continued

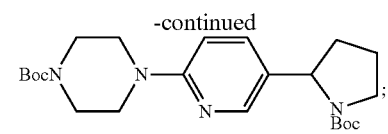

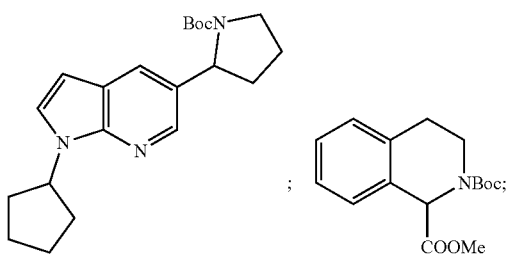

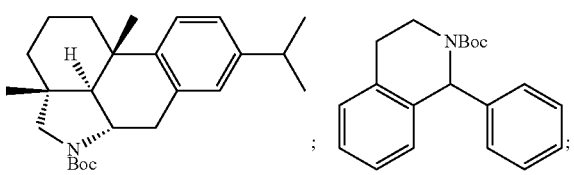

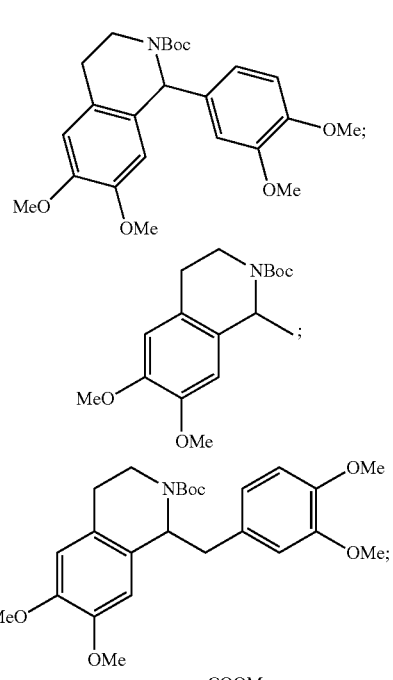

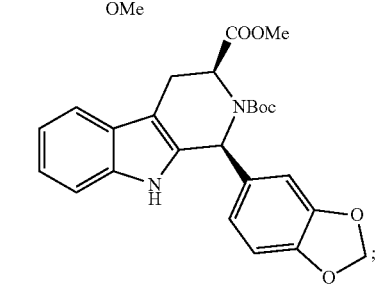

30

-continued

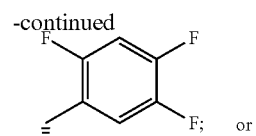

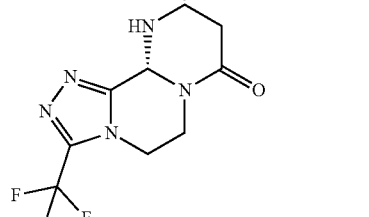

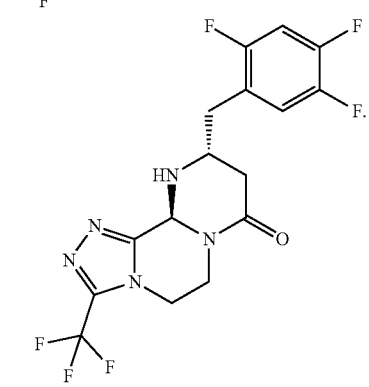

The skilled person understands that the ring-closure amination products formed according to the methods and described above may have one or more chiral centers and thus exist as one or more stereoisomers. Such stereoisomers can exist as a single enantiomer, a mixture of diastereomers or a racemic mixture are encompassed by the present disclosure. As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

III. Uses for the C—H Bond Amination Methods and Products Thereof

The C—H amination methods described above are useful for the synthesis of various ring-closure amination products from a wide variety of organic azide starting materials. In particular, the methods can find application in catalytic transformations in the late-stage functionalization of active pharmaceutical ingredients (APIs) and the synthesis of natural products derivatives. Exemplary natural product derivatives can include, for example, derivatives with a chemical structure shown below:

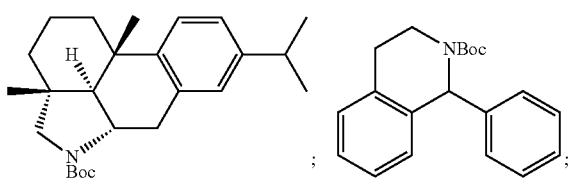

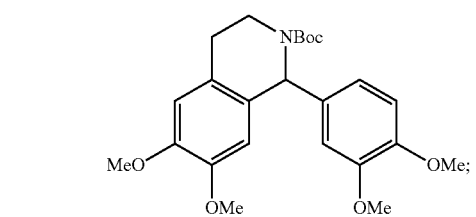

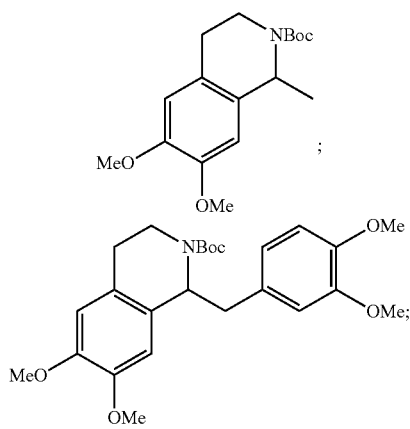

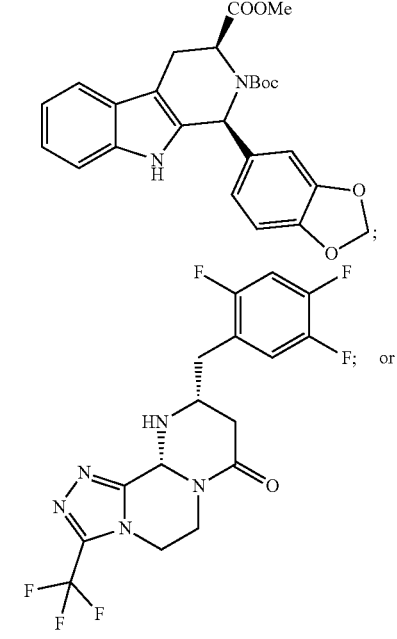

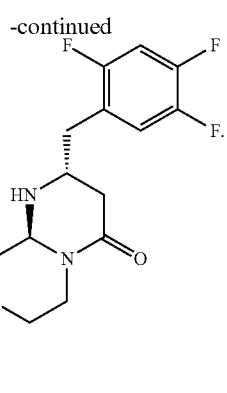

The aforementioned are useful in the manufacture of pharmaceutical products. The disclosed methods can be further understood through the following numbered paragraphs.

Paragraph 1. A method of C—H bond amination comprising the steps of:
(a) forming a reaction mixture comprising an alkyl azide, an iron(II)-phthalocyanine catalyst, and one or more solvents in a reaction vessel; and
(b) heating the reaction mixture to a temperature of at least about 100° C. sufficient to induce a direct intramolecular C—H bond amination of the alkyl azide.

Paragraph 2. The method of paragraph 1, wherein the iron(II)-phthalocyanine catalyst is defined according to any one of Formulae A, B, C, or D:

Formula A

-continued

Formula B

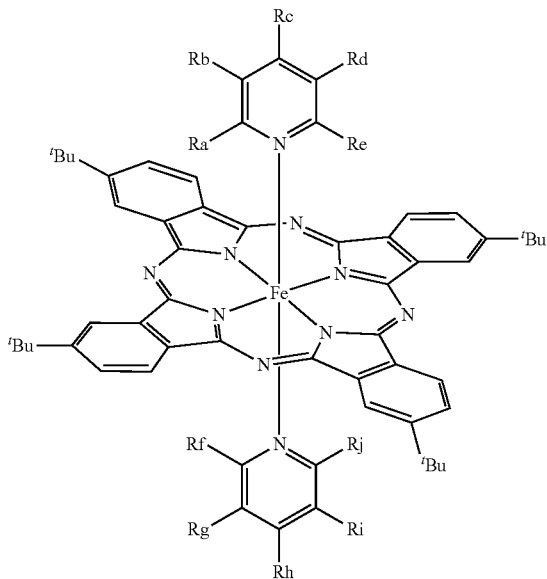

Formula C

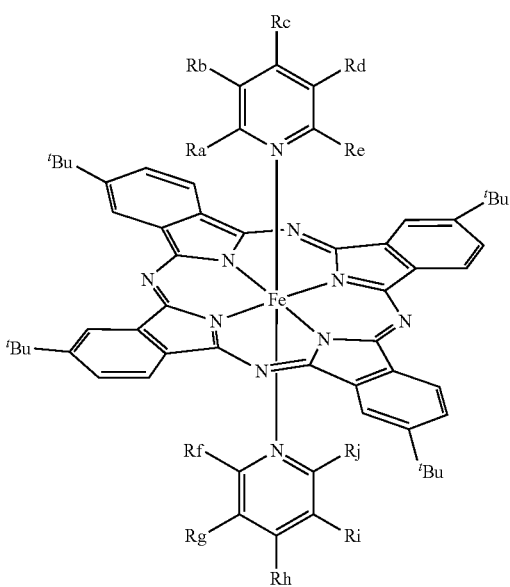

-continued

Formula D

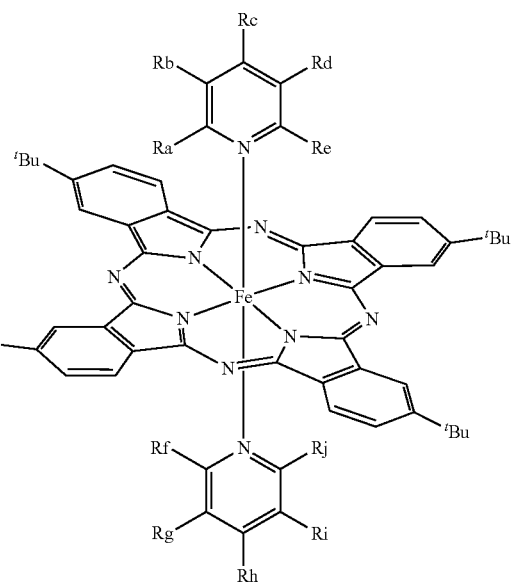

wherein Ra, Rb, Rc, Rd, Re, Rf, Rg, Rh, Ri, and Rj in each of Formulae A-D are each independently selected from the group consisting of a hydrogen; halogen group; a $C_2$-$C_5$ linear or branched alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group, such as methoxy, ethoxy, propoxy, or butoxy; an aryl group; a heteroaryl group; a benzyl group; an acyl group; an ester group; a carbonyl group; a carboxylate group; an amino group; an amide group; and a nitro group.

Paragraph 3. The method of paragraph 2, wherein Ra and Rb, Rb and Rc, Rc and Rd, or Rd and Re can together form a saturated, unsaturated, or aromatic, optionally substituted ring having a total of from 5 to 10 carbon atoms; and/or Rf and Rg, Rg and Rh, Rh and Ri, or Ri and Rj can together form a saturated, unsaturated, or aromatic, optionally substituted ring having a total of from 5 to 10 carbon atoms.

Paragraph 4. The method of any one of paragraphs 2-3, wherein the iron(II)-phthalocyanine catalyst of Formula A has one of the following chemical structures:

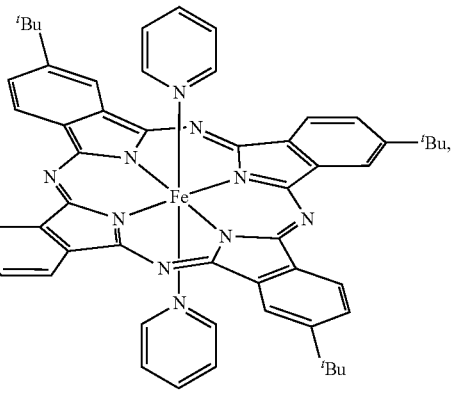

35
-continued
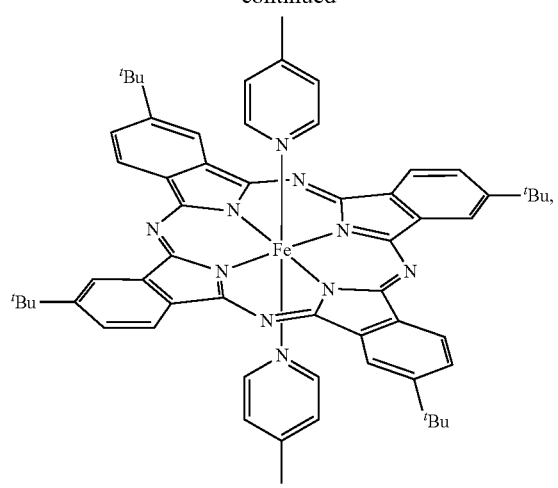
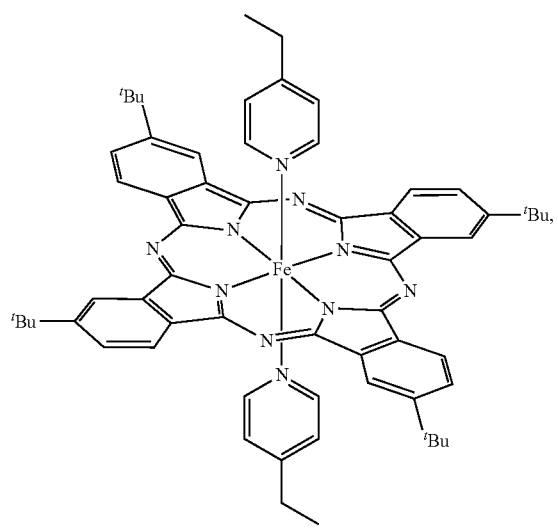
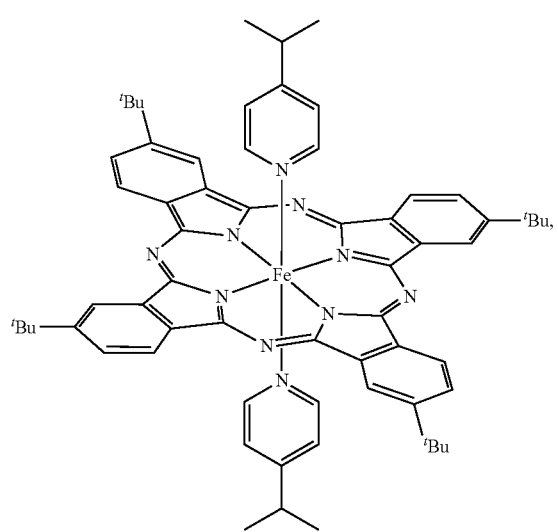
36
-continued
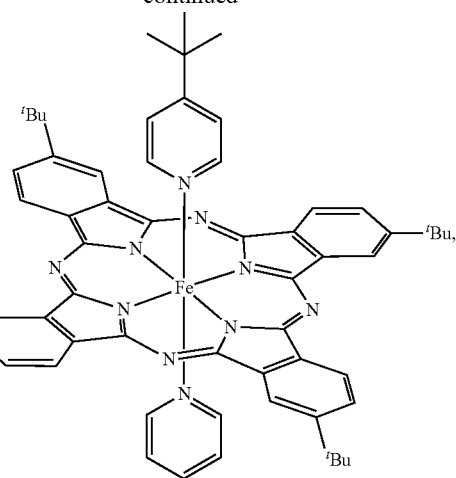
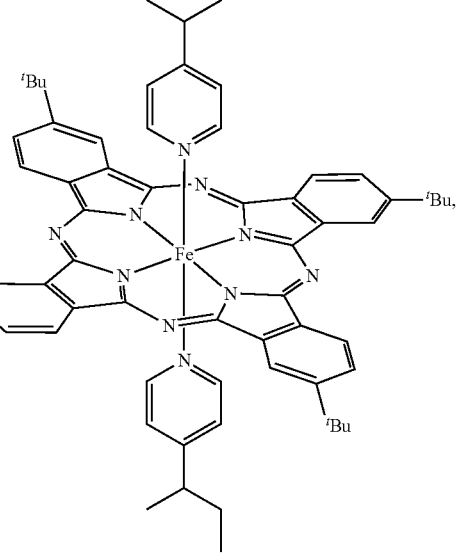
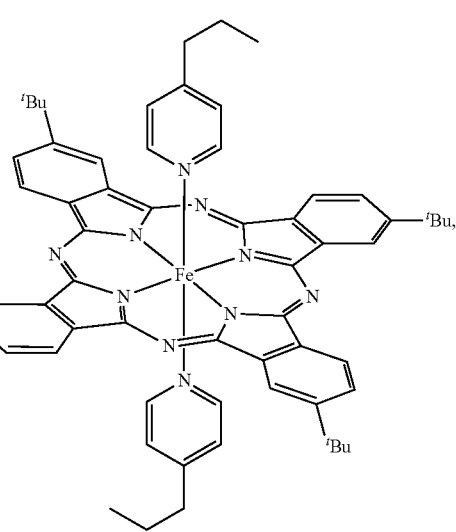

37
-continued
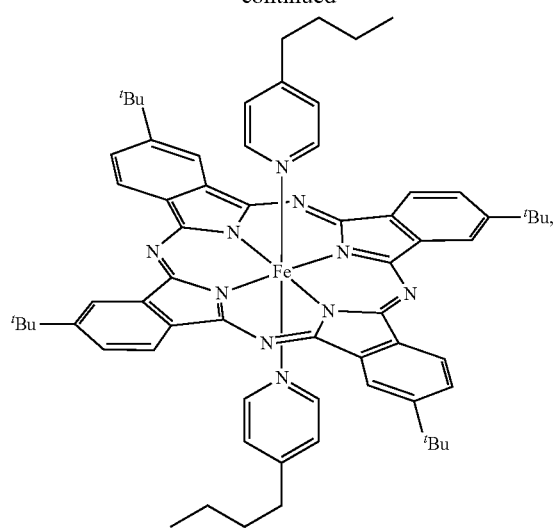
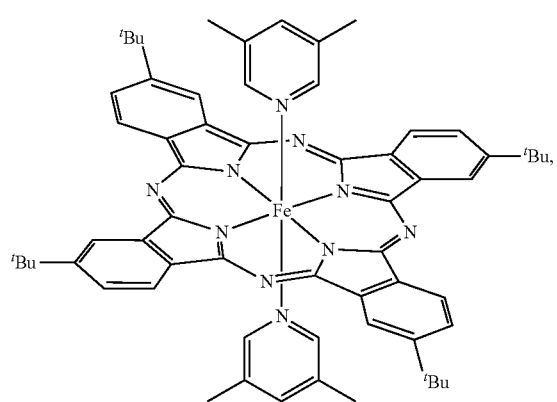
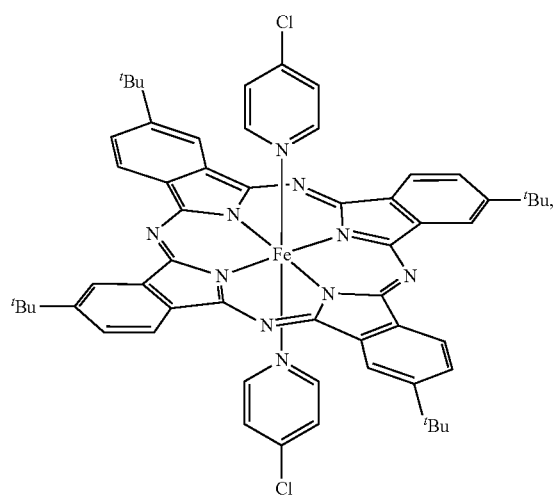
38
-continued
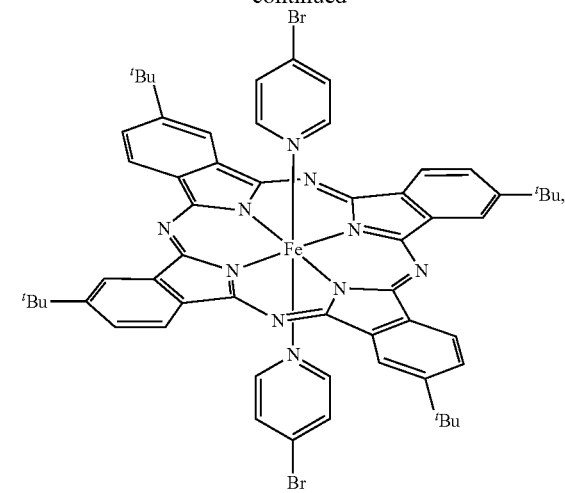
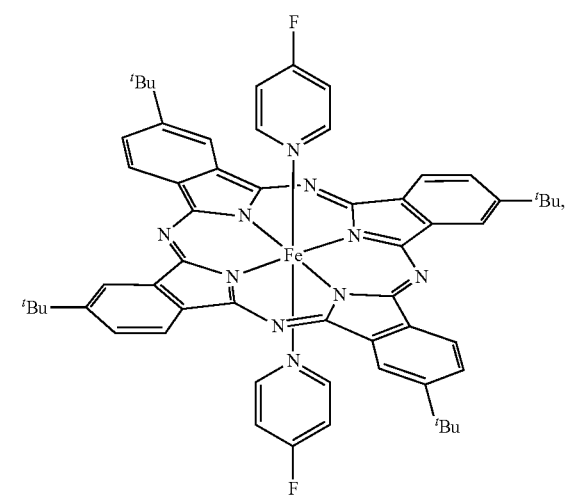
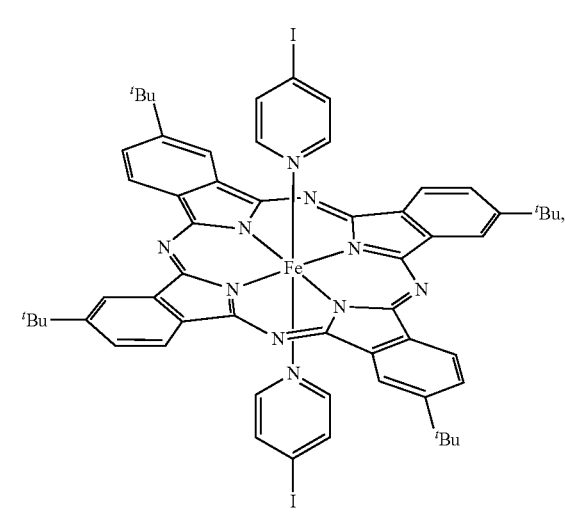

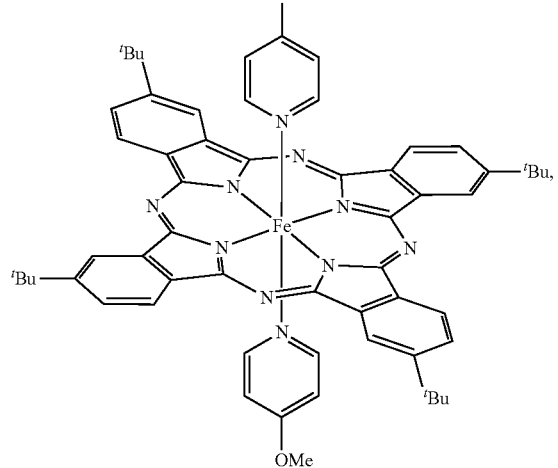
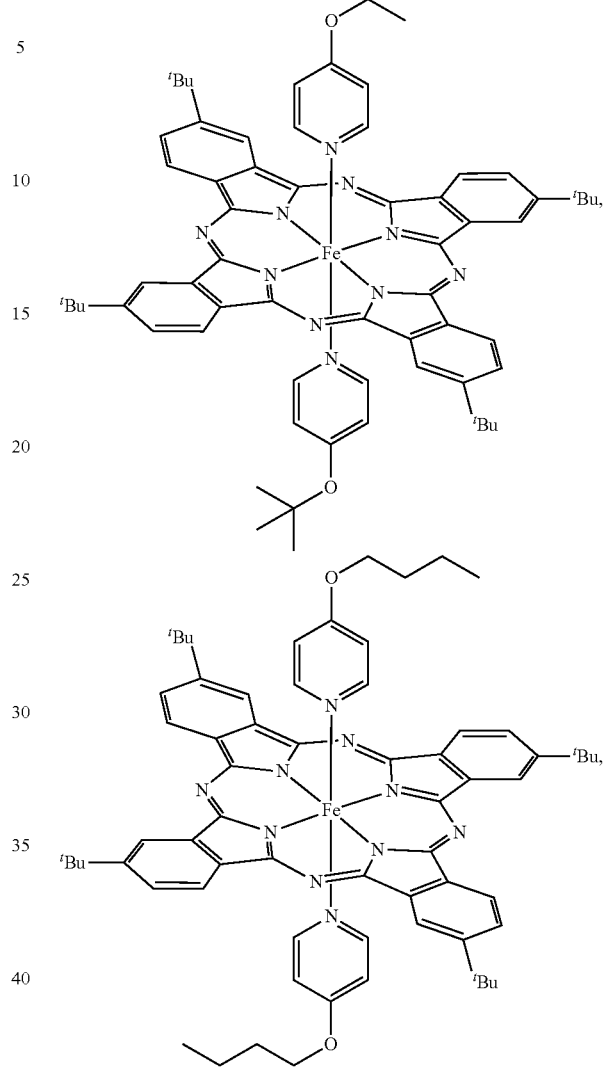
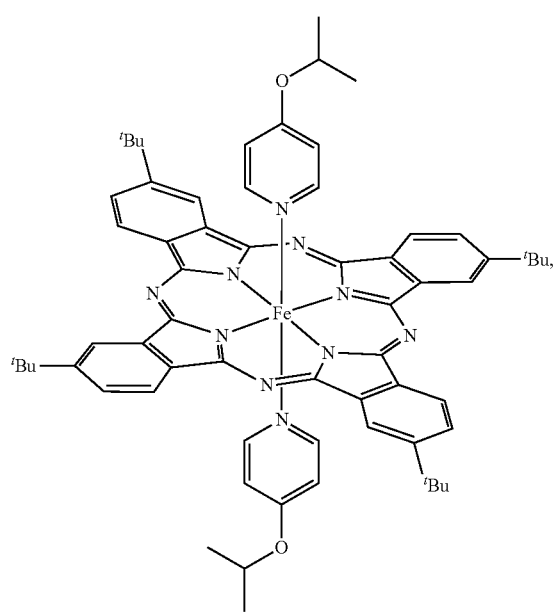
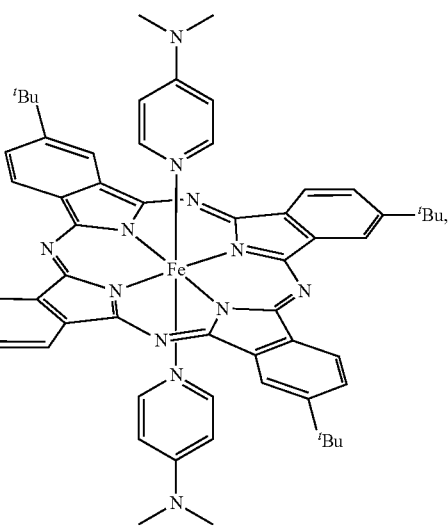

-continued
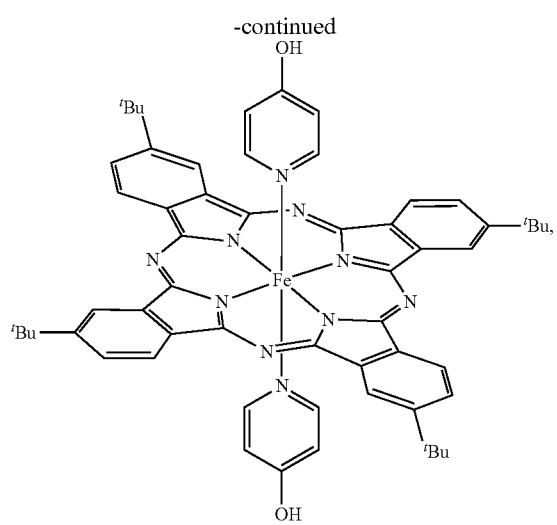
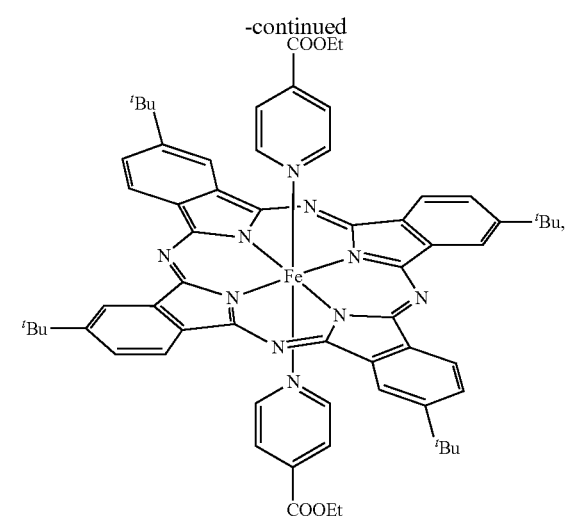
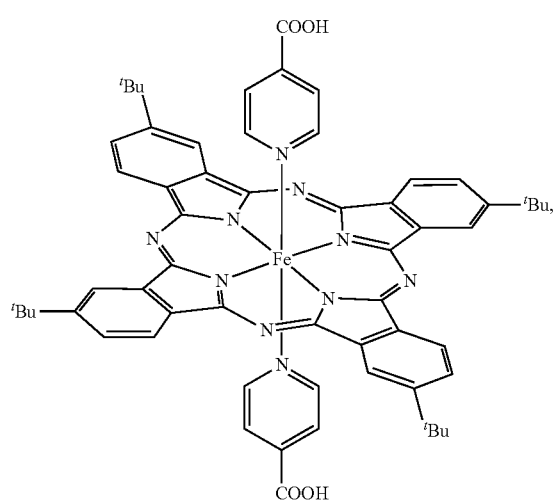
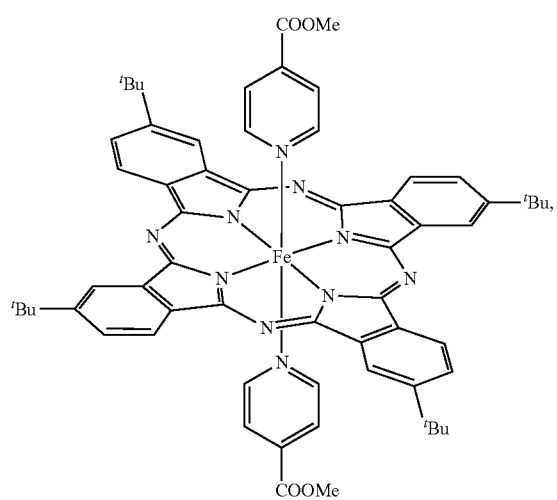
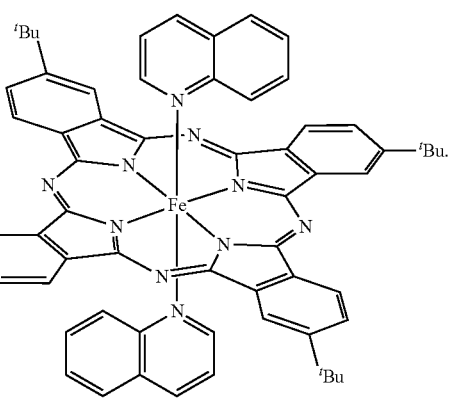
Paragraph 5. The method of any one of paragraphs 1-4, wherein the iron(II)-phthalocyanine catalyst is:

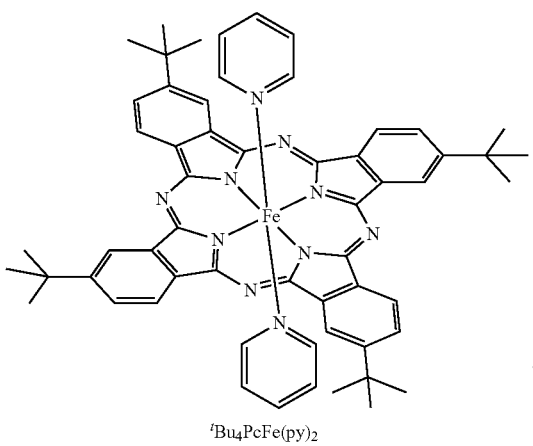

$^tBu_4PcFe(py)_2$

Paragraph 6. The method of any one of paragraphs 1-5, wherein the iron(II)-phthalocyanine catalyst is present in the reaction mixture at an amount of about 0.1 to 5 mol % of the amount of the alkyl azide present; or at an amount of at least about 1, 2, 3, 4, or 5 mol % of the amount of the alkyl azide present.

Paragraph 7. The method of any one of paragraphs 1-6, wherein the reaction mixture is heated to a temperature of about 105° C., 110° C., 115° C., 120° C., 125° C., or 130° C.

Paragraph 8. The method of any one of paragraphs 1-6, wherein the reaction mixture is heated to a temperature in a range of between about 105° C. to about 130° C.

Paragraph 9. The method of any one of paragraphs 1-8, wherein the one or more solvents are organic solvents.

Paragraph 10. The method of paragraph 6, wherein the organic solvents are selected from the group consisting of toluene, benzene, chlorobenzene, 1,2-dichlorobenzene, 1,2-dichloroethane.

Paragraph 11. The method of any one of paragraphs 1-10, wherein the steps (a) and/or (b) are performed under an inert atmosphere.

Paragraph 12. The method of paragraph 11, wherein the inert atmosphere is selected from argon, nitrogen, or a combination thereof.

Paragraph 13. The method of any one of paragraphs 1-12, wherein the heating of step (b) is performed for period of time ranging from between about 0.1 hour to 72 hours, 0.1 hour to 48 hours, or 0.1 hour to 24 hours.

Paragraph 14. The method of any one of paragraphs 1-12, wherein the heating of step (b) is performed for period of time of at least about 10, 15, 20, 25, 30, 35, 40, 45, or 50 hours.

Paragraph 15. The method of any one of paragraphs 1-14, wherein the reaction mixture further comprises at least one reagent for protecting amine groups.

Paragraph 16. The method of paragraph 15, wherein the at least one reagent for protecting amine groups is present in an amount of about 1 to 3 equivalents of the molar amount of the alkyl azide.

Paragraph 17. The method of any one of paragraphs 15-16, wherein the at least one reagent for protecting amine groups is fluorenylmethoxycarbonyl (Fmoc) or di-tert-butyl dicarbonate (Boc$_2$O).

Paragraph 18. The method of any one of paragraphs 1-17, wherein the alkyl azide comprises a benzylic, tertiary, secondary, or primary C—H bond.

Paragraph 19. The method of any one of paragraphs 1-17, wherein the alkyl azide has a chemical structure of Formula I, as follows:

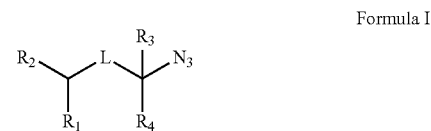

Formula I wherein $R_1$, $R_2$, $R_3$, and $R_4$ are each independently selected from the group consisting of hydrogen; halogen group; a $C_2$-$C_5$ alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group; a heteroaryl group; a benzyl group; an oxo (=O) group; an acyl group; an ester group; a carbonyl group; a carboxylate group; an amino group; an amide group; and a nitro group; and wherein L is a substituted or unsubstituted alkyl radical chain having 3, 4, 5, 6, 7, or 8 carbons, the chain optionally interrupted by at least one heteroatom; and, when substituted, substituents on each of the carbons present are independently selected from the group consisting of hydrogen; halogen group; a $C_2$-$C_5$ alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group; a heteroaryl group; a benzyl group; an oxo (=O) group; an acyl group; an ester group; a carbonyl group; a carboxylate group; an amino group; an amide group; and a nitro group.

Paragraph 20. The method of paragraph 19, wherein the at least one heteroatom, when present, is an oxygen, sulfur, or nitrogen atom.

Paragraph 21. The method of any one of paragraphs 19-20, wherein any two adjacent carbons of the substituted or unsubstituted alkyl radical chain together form a saturated, unsaturated, or aromatic, optionally substituted ring having a total of 5 to 10 carbon atoms.

Paragraph 22. The method of any one of paragraphs 19-21, wherein any one of $R_1$, $R_2$, $R_3$, and $R_4$ and a carbon of the substituted or unsubstituted alkyl radical chain independently together form a saturated, unsaturated, or aromatic, optionally substituted ring having a total of from 5 to 10 carbon atoms.

Paragraph 23. The method of any one of paragraphs 19-22, wherein Ri and $R_2$ together form a saturated, unsaturated, or aromatic, optionally substituted ring having a total of from 5 to 10 carbon atoms.

Paragraph 24. The method of any one of paragraphs 19-23, wherein $R_3$ and $R_4$ together form a saturated, unsaturated, or aromatic, optionally substituted ring having a total of from 5 to 10 carbon atoms.

Paragraph 25. The method of any one of paragraphs 19-22, wherein Ri and $R_3$ or $R_4$ are linked by a saturated, unsaturated, optionally substituted alkyl chain having a total of from 3 to 10 carbon atoms.

Paragraph 26. The method of any one of paragraphs 19-22, wherein $R_2$ and $R_3$ or $R_4$ are linked by a saturated, unsaturated, optionally substituted alkyl chain having a total of from 3 to 10 carbon atoms.

Paragraph 27. The method of any one of paragraphs 1-17, wherein the alkyl azide has a chemical structure of Formula II, as follows:

Formula II

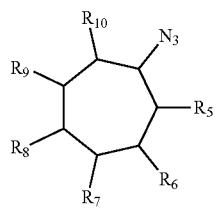

wherein $R_1$, $R_2$, $R_3$, $R_4$, $R_5$, $R_6$, $R_7$, $R_8$, $R_9$, and $R_{10}$ are each independently selected from the group consisting of hydrogen; halogen group; a $C_2$-$C_5$ alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group; a heteroaryl group; a phenyl group; a benzyl group; an oxo (=O) group; an acyl group; an ester group; a carbonyl group; a carboxylate group; an amino group; an amide group; and a nitro group.

Paragraph 28. The method of any one of paragraphs 1-27, wherein the direct intramolecular C—H bond amination of the alkyl azide affords a ring-closure amination product of the alkyl azide.

Paragraph 29. The method of paragraph 28, wherein the ring-closure amination product has a chemical structure shown below:

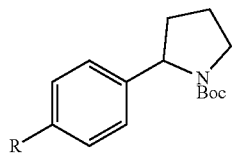

wherein R is H, Me, OMe, Cl, Br, F, $NO_2$, or N,N-dimethyl;

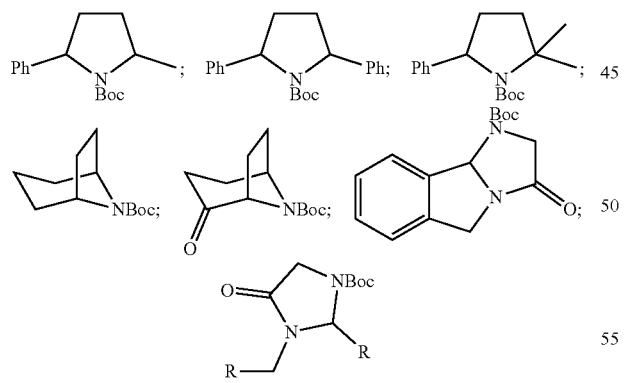

wherein each R is 4-OMe$C_6H_4$;

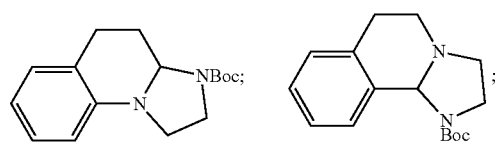

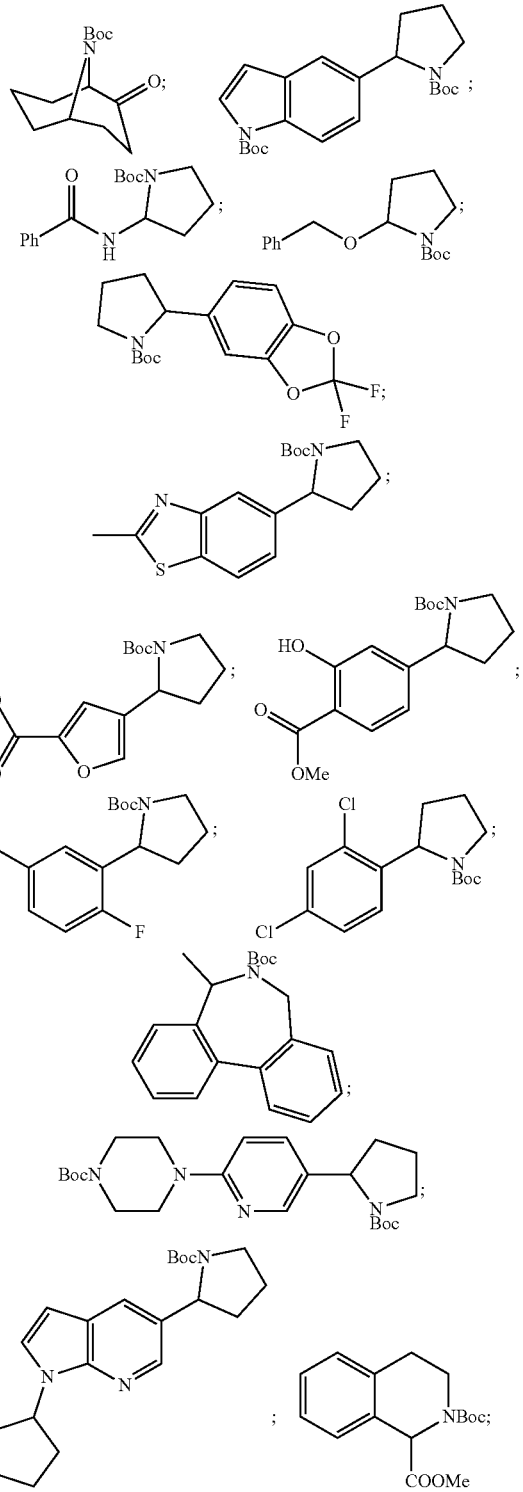

-continued
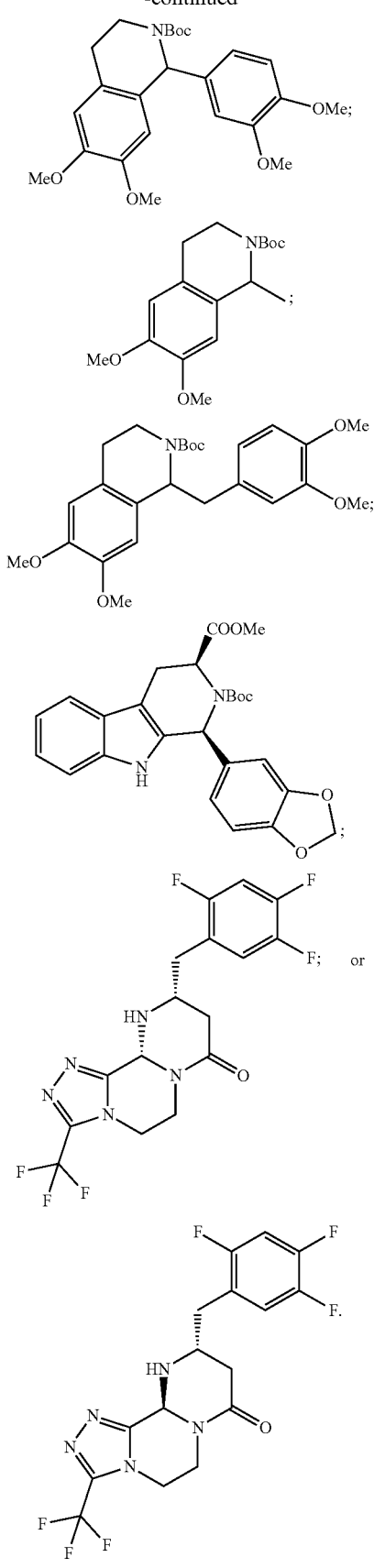
Paragraph 30. A natural product derivative prepared using the method of any one of paragraphs 1-28, wherein the natural product derivative has a chemical structure shown below:
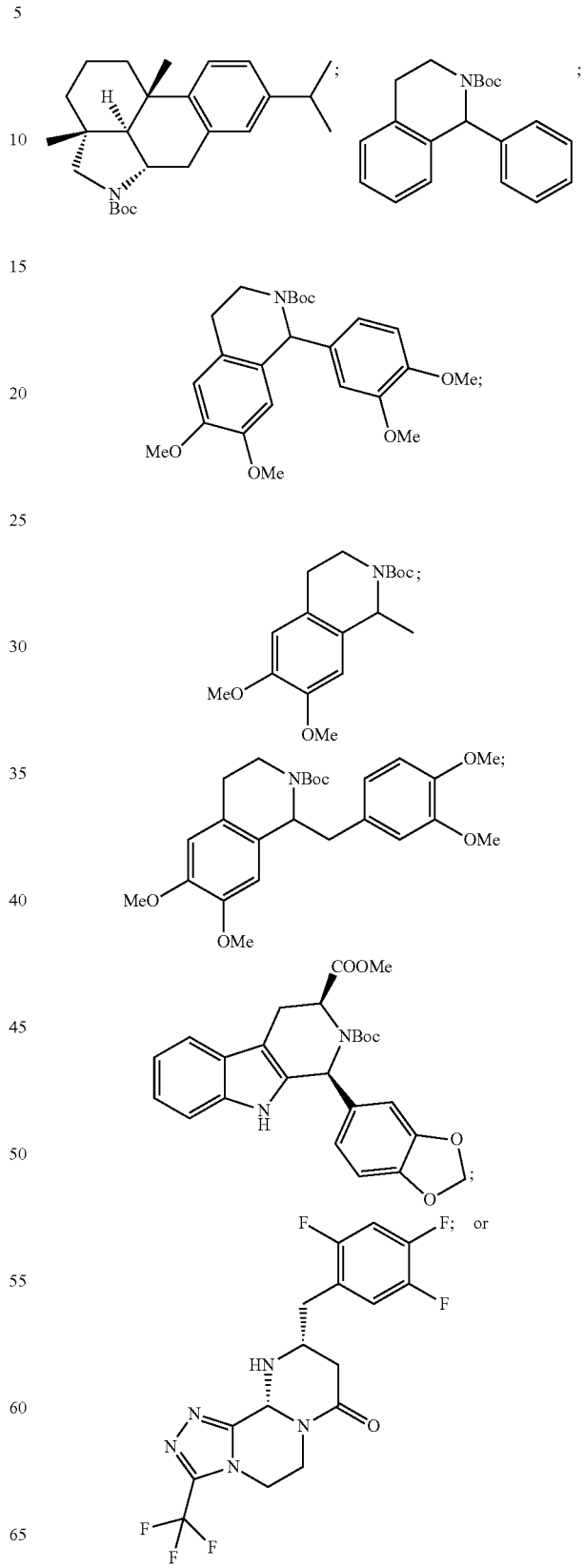

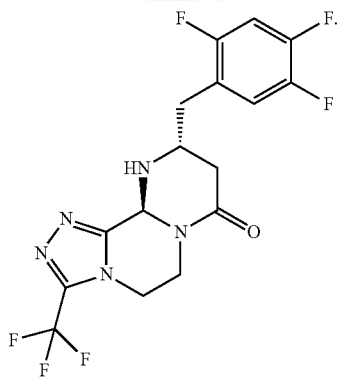

Paragraph 31. An iron(II)-phthalocyanine catalyst defined according to any one of Formulae A, B, C, or D:

Formula A

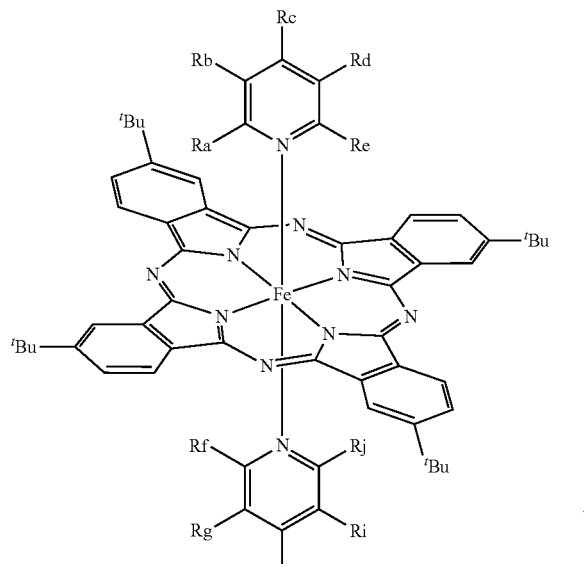

Formula B

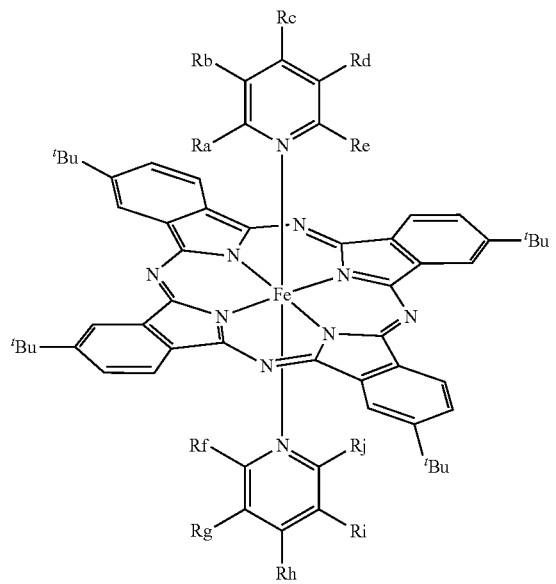

Formula C

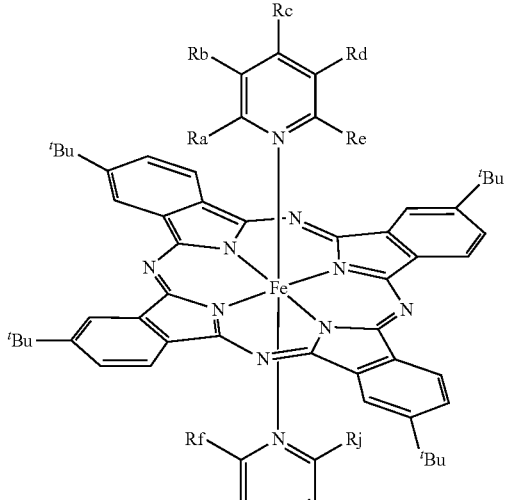

Formula D wherein Ra, Rb, Rc, Rd, Re, Rf, Rg, Rh, Ri, and Rj in each of Formulae A-D are each independently selected from the group consisting of a hydrogen; halogen group; a $C_2$-$C_5$ linear or branched alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group, such as methoxy, ethoxy, propoxy, or butoxy; an aryl group; a heteroaryl group; a benzyl group; an acyl group; an ester group; a carbonyl group; a carboxylate group; an amino group; an amide group; and a nitro group.

Paragraph 32. The iron(II)-phthalocyanine catalyst of paragraph 31, wherein Ra and Rb, Rb and Rc, Rc and Rd, or Rd and Re can together form a saturated, unsaturated, or aromatic, optionally substituted ring having a total of from 5 to 10 carbon atoms; and/or Rf and Rg, Rg and Rh, Rh and Ri, or Ri and Rj can together form a saturated, unsaturated, or aromatic, optionally substituted ring having a total of from 5 to 10 carbon atoms.

Paragraph 33. The iron(II)-phthalocyanine catalyst of any one of paragraphs 31-32, wherein the iron(II)-phthalocyanine catalyst has one of the following chemical structures:
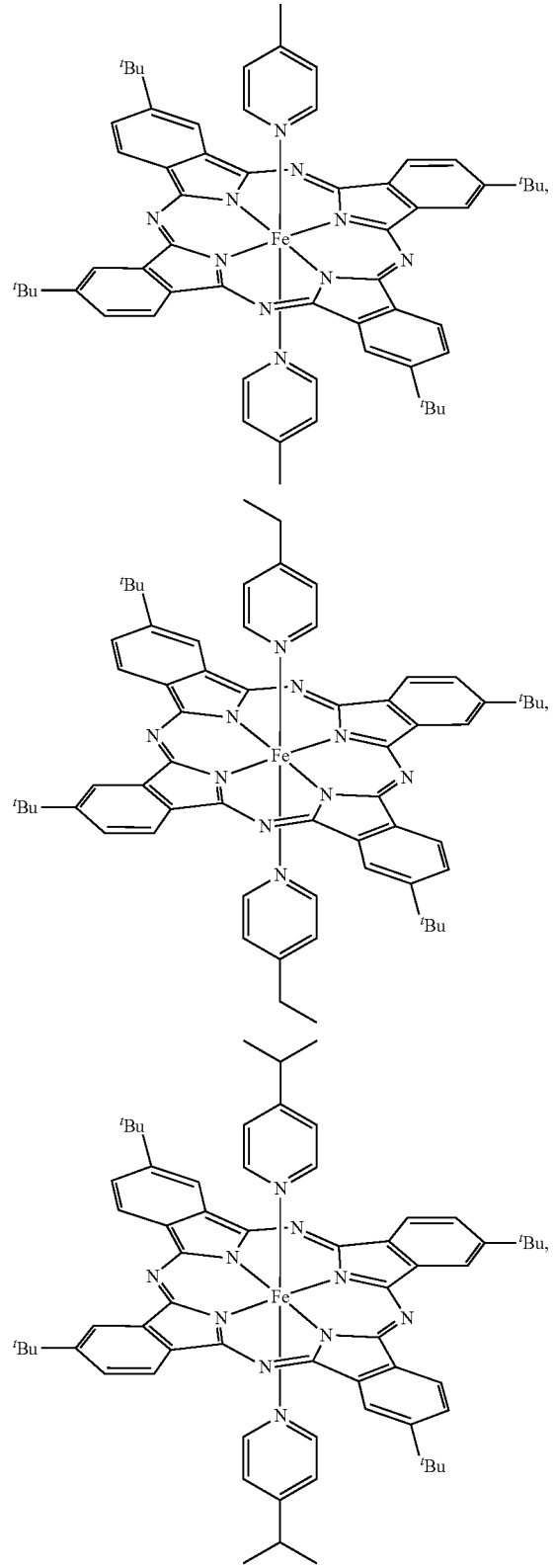
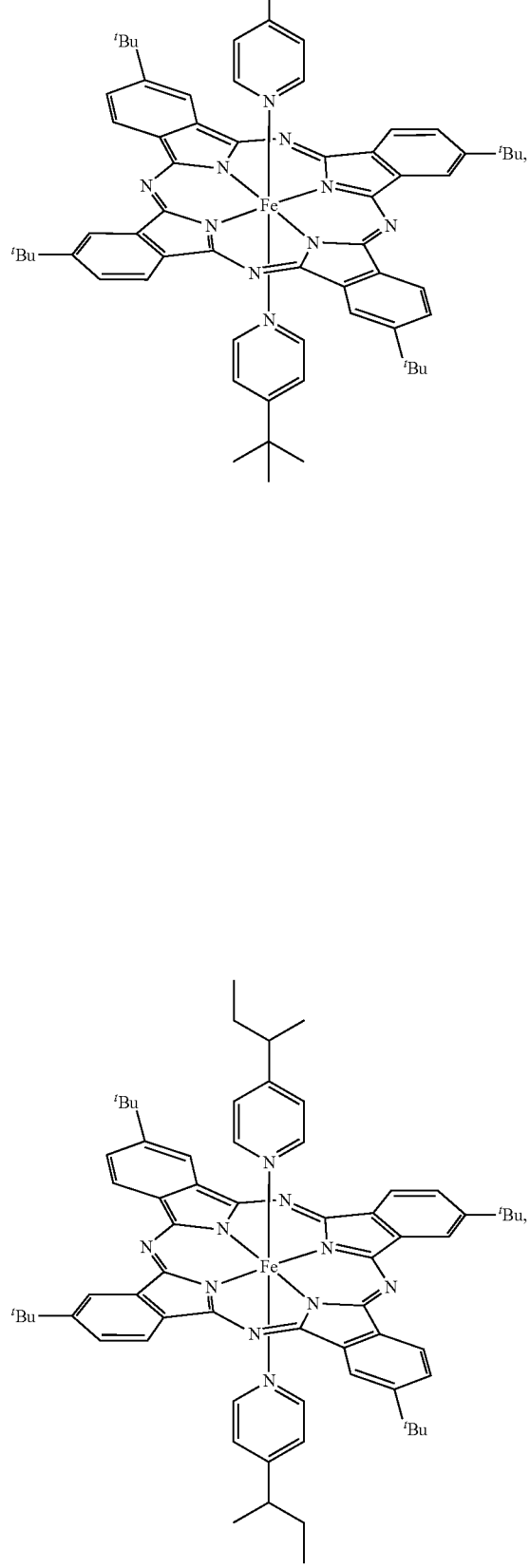

53
-continued
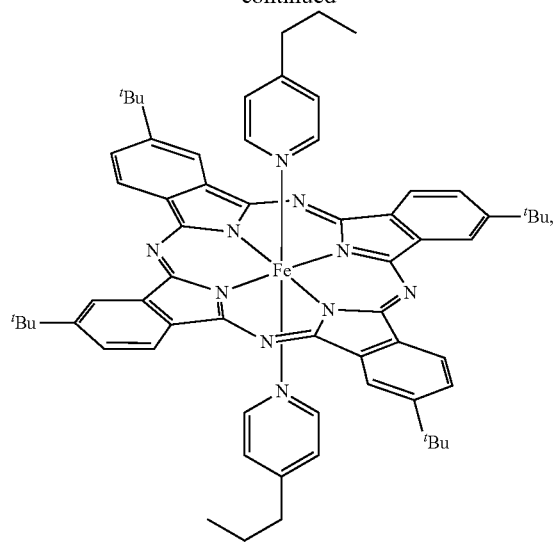
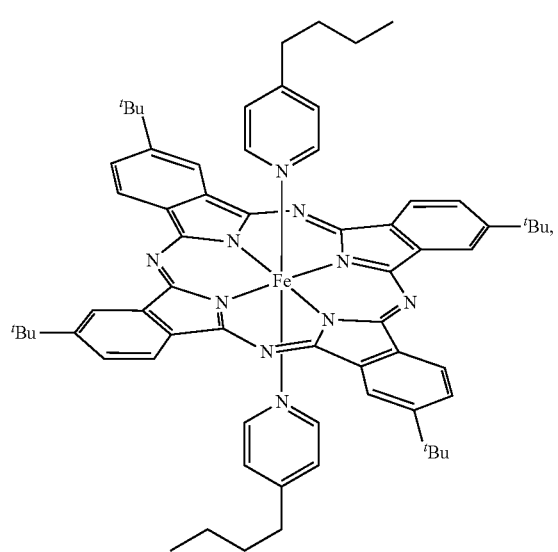
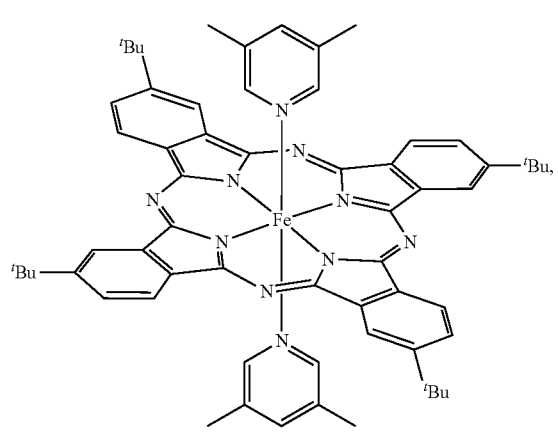
54
-continued
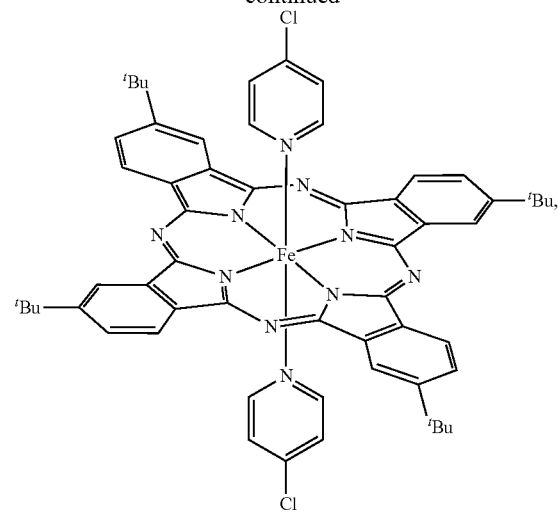
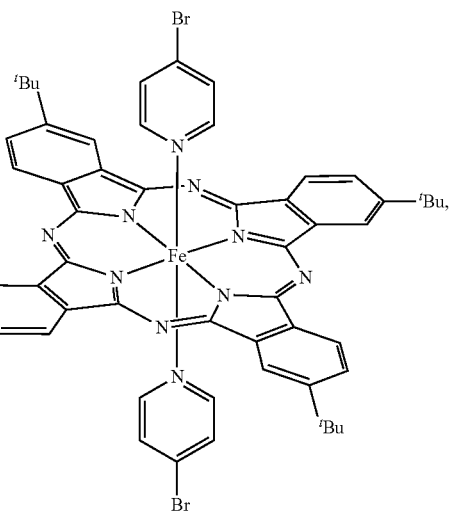
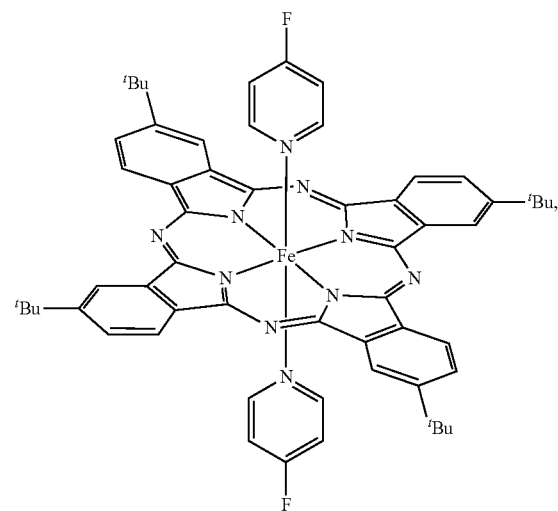

55
-continued
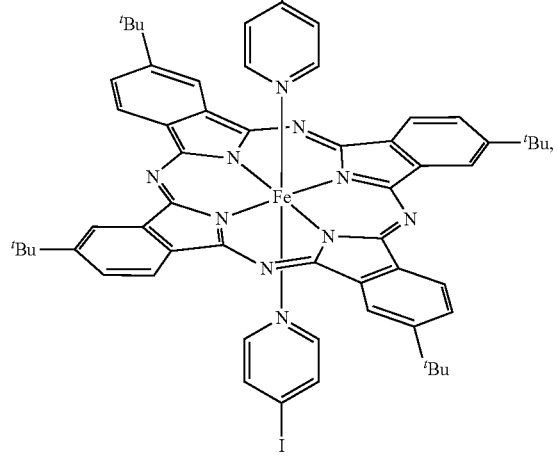
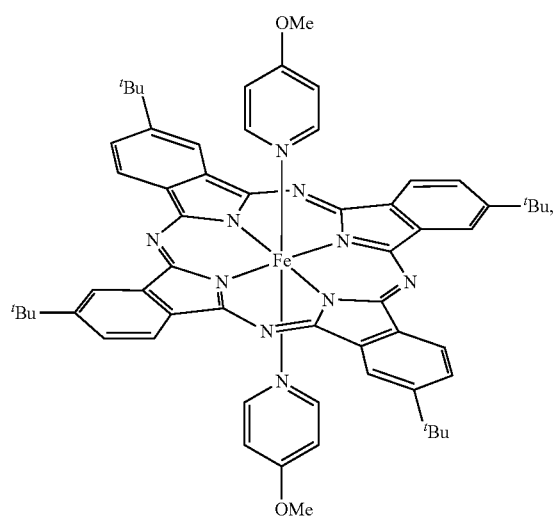
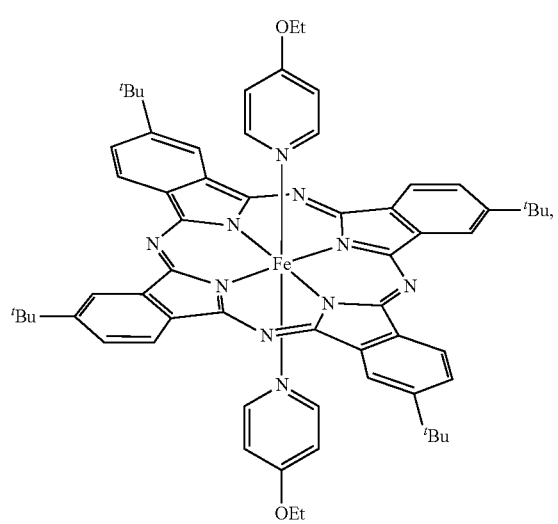
56
-continued
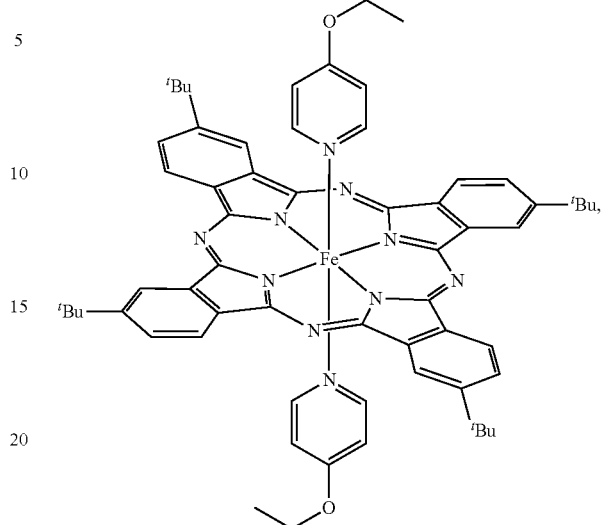
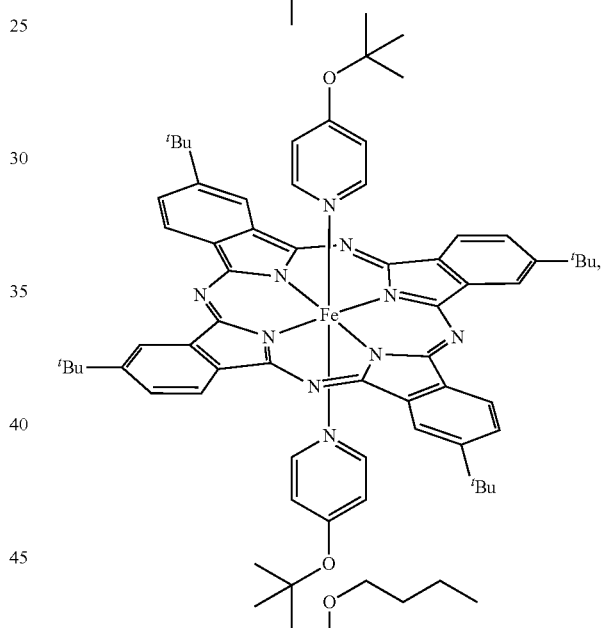
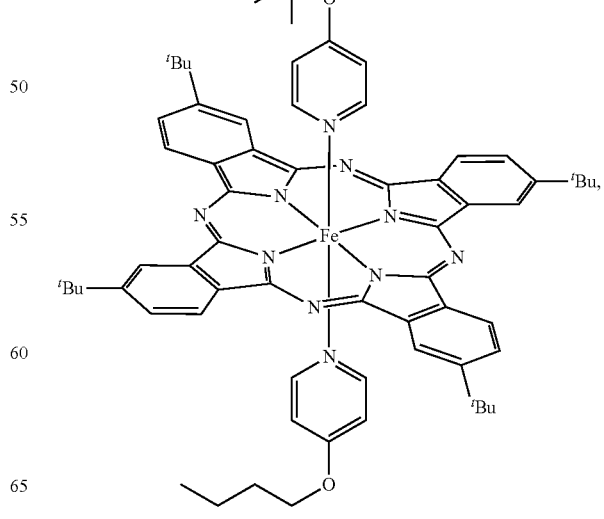

57
-continued
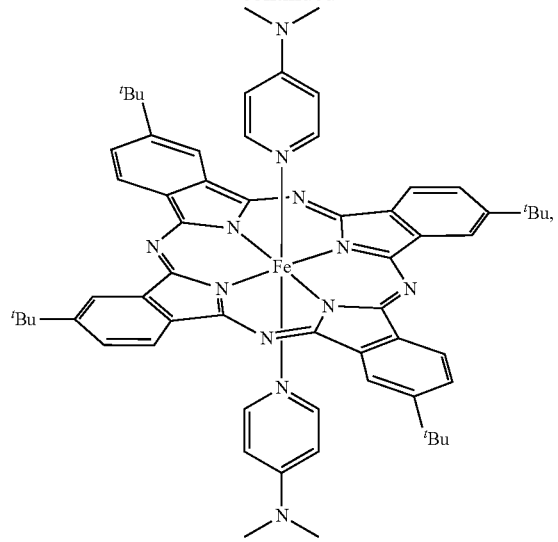
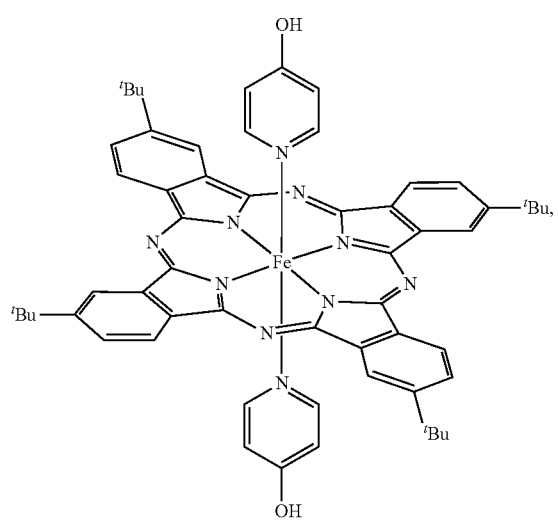
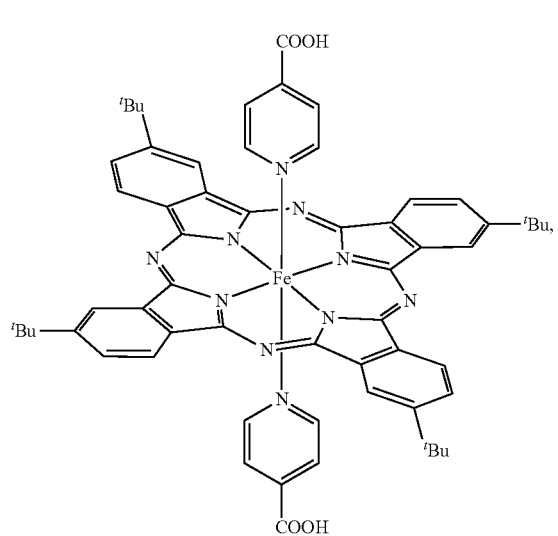
58
-continued
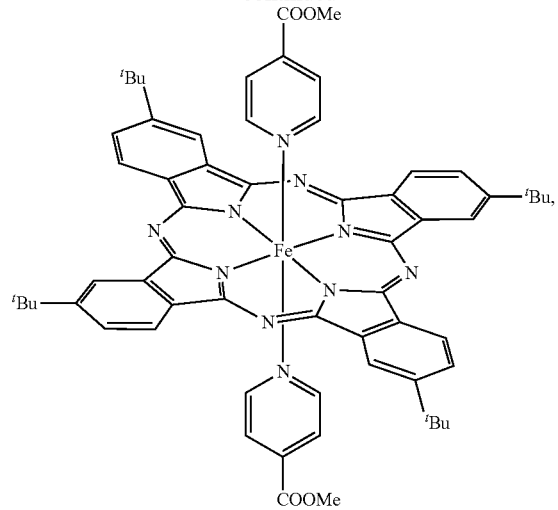
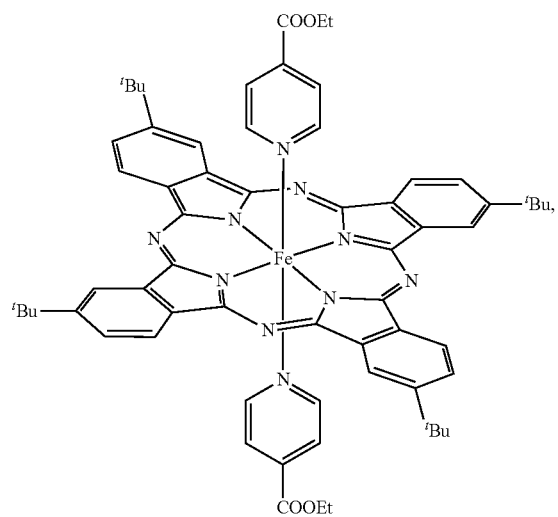
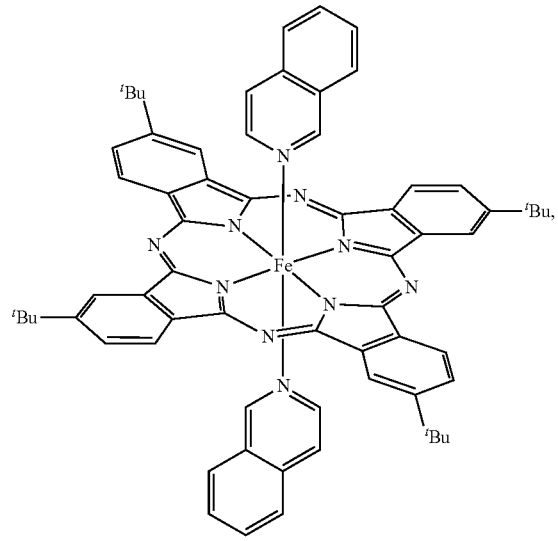

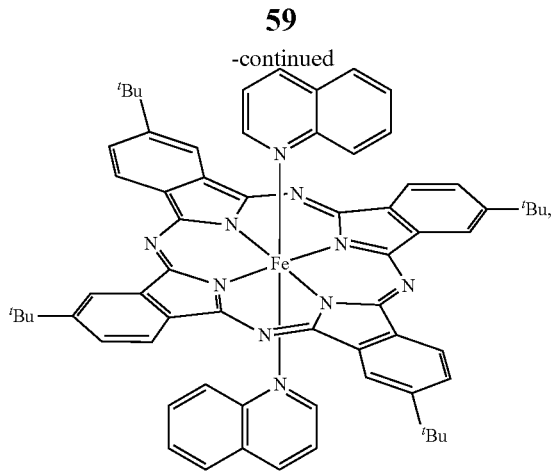

and isomers thereof.

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of disclosed forms. Theoretical aspects are presented with the understanding that Applicants do not seek to be bound by the theory presented.

EXAMPLES

Materials:

The chemical reagents used for syntheses described were purchased from commercial including Sigma-Aldrich, Acros Organics, J&K Scientific. They were directly used without further process unless otherwise specified. The solvents used for syntheses described were purchased from Acros Organics, RCI Labscan, Scharlab and J&K Scientific. They were directly used without further process unless otherwise specified.

Catalyst $^tBu_4PcFe(py)_2$ is a known compound and was prepared according to a previous literature report (*Inorg. Chem.* 1984, 23, 1065). Catalyst $^tBu_4PcFe(py)$ was characterized by ESI mass spectrometry, UV/Vis, and $^1H$ NMR spectroscopy. $^1H$ NMR (400 MHz, Benzene-$d_6$) δ 9.90-9.84 (m, 4H), 9.67 (dd, J=8.0, 2.9 Hz, 4H), 8.00-7.93 (m, 4H), 4.60 (t, J=7.5 Hz, 2H), 3.81 (t, J=7.0 Hz, 4H), 2.43 (d, J=5.4 Hz, 4H), 1.61-1.49 (m, 36H).

$^1H$ NMR spectra were recorded on either a Bruker DPX-500 or DPX-400 NMR spectrometer. The chemical shift of proton signals were calibrated by the corresponding solvent residual signals. ESI mass spectrometry was recorded on Q Exactive mass spectrometer (Thermo Fisher Scientific, USA) spectrometer. UV/Vis spectroscopy was recorded on an Agilent Cary 8454 spectrometer. X-ray crystallography structures were recorded on a Bruker APEX-II CCD diffractometer.

Example 1: Intramolecular C—H Amination of (4-azidobutyl)benzene

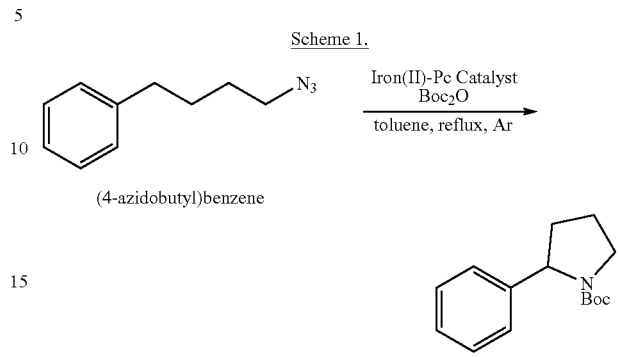

Procedures for this catalysis reaction: an oven-dried Schlenk tube was charged with (4-azidobutyl)benzene (0.2 mmol, 1.0 equiv.), $Boc_2O$ (2.0 equiv), iron(II)-Pc catalyst $^tBu_4PcFe(py)_2$ (1 mol %), and dry toluene (2.0 mL) under argon. The mixture was refluxed violently (130° C.) until full completion, as revealed by TLC (usually completion within 6 h). The reaction mixture was cooled to room temperature and concentrated, and the residue was purified by silica gel column chromatography to give the corresponding product. This product was verified by NMR by comparing to the reported characterization data (*Science*, 2013, 340, 591).

The same reaction using the μ-oxo complex [(($^tBu_4Pc$)Fe$^{III}$)$_2$O] or μ-nitrido complex [(($^tBu_4Pc$)Fe)$_2$N] as catalysts using the same procedure as described above. [(($^tBu_4Pc$)Fe$^{III}$)$_2$O] and [(($^tBu_4Pc$)Fe)$_2$N] are known compounds and were synthesized according to literature references (C. Ercolani, et al., *J. Porphyrins Phthalocyanines*, 2001, 05, 668; H. M. Neu, et al., *Adv. Synth. Catal.*, 2009, 351, 3168; A. B. Sorokin, et al., *Chem. Commun.*, 2008, 2562, respectively). The catalysts were found to be less efficient than $^tBu_4PcFe(py)_2$. It was also observed that temperatures of about 100° C. or less inhibited the C—H amination reaction, which suggested that higher temperatures were needed to afford satisfactory product yields.

Example 2: C—H Amination of Alkyl Azides Using Iron(II) Catalyst

Different alkyl azide starting reagents are used below to undergo C—H amination. It is noted that organic azides are potentially explosive and should be handled with care. While no problems were encountered during their synthesis, proper precautions should be taken during the whole process of handling such compounds. Once isolated, azides were stored in a −20° C. freezer.

Alkyl azides reported in previous literatures discussed in the Examples were as listed in Table 1 below. Detailed synthetic procedures and characterizations for other unknown azides are shown, as described below.

TABLE 1

| Reported azides in the literature | |
|---|---|
| Azides | References |
| Ph~~~N₃ | E. T. Hennessy |

TABLE 1-continued

| Azides | References |
|---|---|
| 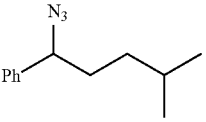 | and T. A. Betley, *Science*, 2013, 340, 591 |
| 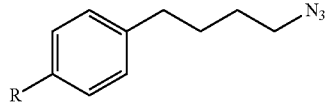<br>R = Me; R = OMe<br>R = N,N-dimethyl; R = F<br>R = Cl | J. Qin, Z. Zhou, T. Cui, M. Hemming and E. Meggers, *Chem. Sci.*, 2019, 10, 3202 |
| 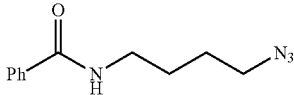 [SMILES: [N-]=[N+]=NCCCCNC(=O)c1ccccc1] | Y. Xia, L. Wang and A. Studer, *Angew. Chem. Int. Ed.*, 2018, 57, 12940 |
| 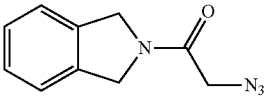<br>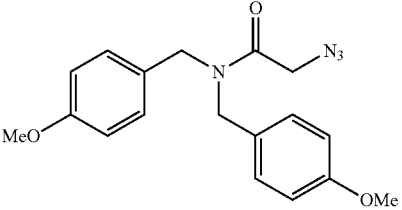 [SMILES: COc1ccc(CN(Cc2ccc(OC)cc2)C(=O)CN=[N+]=[N-])cc1] | Z. Zhou, S. Chen, J. Qin, X. Nie, X. Zheng, K. Harms, R. Riedel, K. N. Houk and E. Meggers, *Angew. Chem. Int. Ed.*, 2019, 58, 1088 |
| 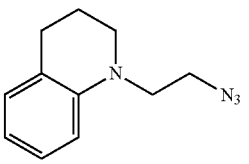 [SMILES: [N-]=[N+]=NCCN1CCCc2ccccc21]<br>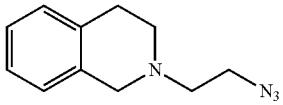 [SMILES: [N-]=[N+]=NCCN1CCc2ccccc2C1] | Y.-D. Du, C.-Y. Zhou, W.-P. To, H.-X. Wang and C.-M. Che, *Chem. Sci.*, 2020, 11, 4680 |
| 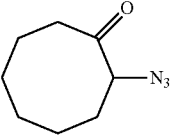 [SMILES: [N-]=[N+]=NC1CCCCCCC1=O] | |
| 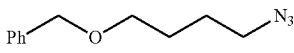 [SMILES: [N-]=[N+]=NCCCCOCc1ccccc1] | Y. Chen, Z. Li, Y. Liu, T. Lin, H. Sun, D. Yang and C. Jiang, *Bioorg. Chem.*, 2018, 81, 278 |

TABLE 1-continued

Reported azides in the literature

| Azides | References |
|---|---|
| | D. A. Iovan, M. J. T. Wilding, Y. Baek, E. T. Hennessy and T. A. Betley, *Angew. Chem. Int. Ed.*, 2017, 56, 15599 |
| | K.-P. Shing, Y. Liu, B. Cao, X.-Y. Chang, T. You and C.-M. Che, *Angew. Chem. Int. Ed.*, 2018, 57, 11947 |
| | G. Meng, T. Guo, T. Ma, J. Zhang, Y. Shen, K. B. Sharpless and J. Dong, *Nature*, 2019, 574, 86 |

Syntheses of Alkyl Azides and their Precursors:
General Procedure A: Synthesis of Alkyl Azides from Alkyl Alcohols (Two Steps)

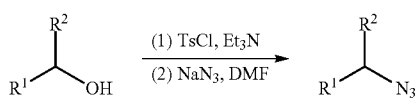

Step 1: To a stirring solution of primary or secondary alcohol (1 equiv., 0.5 M) in anhydrous dichloromethane, triethylamine (1.5 equiv.) and 4-dimethylaminopyridine (0.1 equiv.) were added. 4-Toluenesulfonyl chloride (1.2 equiv.) was added at 0° C. The reaction was allowed to warm up to room temperature and stirred overnight, then the mixture was quenched with water once completion. The aqueous phase was extracted three times with dichloromethane. The combined organic phases were washed with sat. aq. NaHCO$_3$ and brine, dried over Na$_2$SO$_4$, filtered and concentrated under reduced pressure. The residue was either purified by silica column chromatography or used without further purification.

Step 2: To a stirring solution of the above (purified or crude) tosylate (1 equiv., 0.5 M) (or alkyl chloride, in few cases alkyl chloride instead of tosylate was obtained) in DMF was added sodium azide (1.5 equiv.), and the reaction was heated at 80° C. overnight. After completion of the reaction water was added and the mixture was extracted with Et$_2$O three times. The combined organic phases were washed twice with water and brine, and dried over Na$_2$SO$_4$. After removal of the solvent under reduced pressure the residue was purified by silica column chromatography to give the desired azide.

General Procedure B: Synthesis of Saturated Alkyl Alcohols from the Reduction of Unsaturated Precursors To a solution of unsaturated substrate containing double bond or triple bond (5 mmol, 0.1M) in MeOH was added 10% Pd/C (100 mg). Then the mixture was stirred vigorously under $H_2$ atmosphere (1 atm) for overnight. Upon completion, the reaction mixture was filtered through celite and washed with dichloromethane and ethyl acetate. Usually after removal of the solvent the residue can be obtained with enough purity for the next step directly and in few cases further purification is needed before next step.

General Procedure C: Synthesis of Alkyl Alcohols from the Reduction of Alkyl Carboxylic Acid or Ester To a solution of the desired carboxylic acid or ester (5 mmol, 1 equiv., 0.5M) in THF was added $LiAlH_4$ (379.5 mg, 10 mmol, 2 equiv.) portionwise at 0° C. under argon atmosphere. Then the solution was stirred at rt for overnight. After completion, the reaction was quenched by adding a solution of NaOH aqueous (10% in water) until a solid precipitated. After filtration over $MgSO_4$ and evaporation of the solvent the crude alcohol was directly used for the next step without further purification.

General Procedure D: Cross Coupling of Aryl Iodides with but-3-yn-1-ol (K. R. Roesch and R. C. Larock, *J. Org. Chem.*, 2002, 67, 86)

To a solution of aryl iodide (1.0 equiv), $PdCl_2(PPh_3)_2$ (0.05-0.1 equiv.), CuI (0.15-0.3 equiv.) in $Et_3N$ (0.25M) was added but-3-yn-1-ol (1.3 equiv) and the mixture was stirred at room temperature under argon atmosphere. After completion, the resulting mixture was concentrated under reduced pressure and subjected to column chromatography on silica gel to give the desired coupling product.

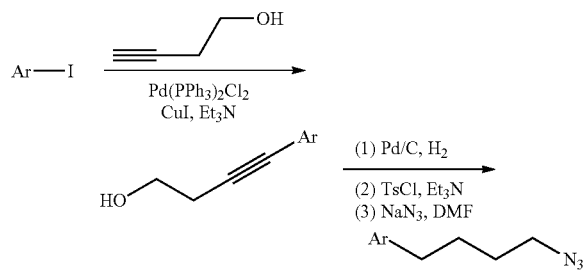

Alkyl Halide Characterization Data:

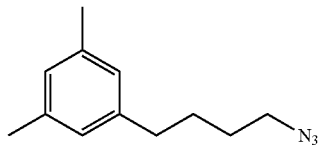

1-(4-azidobutyl)-3,5-dimethylbenzene: Synthesized following the general procedures D, B and A from 1-iodo-3,5-dimethylbenzene and obtained as a colorless oil (46% over four steps). $^1$H NMR (400 MHz, $CDCl_3$) δ 6.90 (s, 1H), 6.86 (s, 2H), 3.33 (t, J=6.6 Hz, 2H), 2.63 (t, J=7.3 Hz, 2H), 2.36 (s, 6H), 1.79-1.65 (m, 4H). $^{13}$C NMR (100 MHz, $CDCl_3$) δ 141.8, 137.9, 127.6, 126.3, 51.4, 35.3, 28.5, 21.3. HRMS (ESI) m/z: $[M-N_2+H]^+$ calcd. for $[C_{12}H_{18}N]^+$: 176.1434, found: 176.1434.

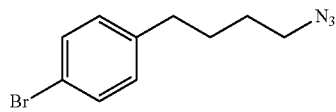

1-(4-azidobutyl)-4-bromobenzene: Synthesized following the general procedure A from 4-(4-bromophenyl)butan-1-ol and obtained as a colorless oil (78% over two steps). $^1$H NMR (500 MHz, $CDCl_3$) δ 7.40 (d, J=8.3 Hz, 2H), 7.05 (d, J=8.4 Hz, 2H), 3.28 (t, J=6.6 Hz, 2H), 2.59 (t, J=7.4 Hz, 2H), 1.71-1.58 (m, 4H). $^{13}$C NMR (125 MHz, $CDCl_3$) δ 140.8, 131.4, 130.1, 119.7, 51.3, 34.8, 28.4, 28.3. HRMS (ESI) m/z: $[M-N_2+H]^+$ calcd. for $[C_{10}H_{13}NBr]^+$: 226.0226, found 226.0222.

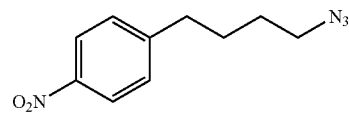 [SMILES: [N-]=[N+]=NCCCCc1ccc([N+](=O)[O-])cc1]

1-(4-azidobutyl)-4-nitrobenzene: Synthesized following the general procedure A from 4-(4-nitrophenyl)butan-1-ol and obtained as a light yellow oil (77% over two steps). $^1$H NMR (400 MHz, $CDCl_3$) δ 8.15 (d, J=8.7 Hz, 2H), 7.34 (d, J=8.6 Hz, 2H), 3.32 (t, J=6.6 Hz, 2H), 2.76 (t, J=7.6 Hz, 2H), 1.80-1.60 (m, 4H). $^{13}$C NMR (125 MHz, $CDCl_3$) δ 149.7, 146.4, 129.2, 86123.7, 51.2, 35.3, 28.4, 28.0. HRMS (ESI) m/z: $[M-N_2+H]^+$ calcd. for $[C_{10}H_{13}O_2N_2]^+$: 193.0972, found 193.0971.

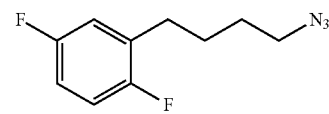 [SMILES: [N-]=[N+]=NCCCCc1cc(F)ccc1F]

2-(4-azidobutyl)-1,4-difluorobenzene: Synthesized following the general procedures D, B and A from 1,4-difluoro-2-iodobenzene and obtained as a colorless oil (30% over four steps). $^1$H NMR (400 MHz, $CDCl_3$) δ 6.96 (td, J=9.0, 4.6 Hz, 1H), 6.91-6.81 (m, 2H), 3.30 (t, J=6.5 Hz, 2H), 2.65 (t, J=7.0 Hz, 2H), 1.75-1.59 (m, 4H). $^{13}$C NMR (100 MHz, $CDCl_3$) δ 159.0 (dd, J=159.2, 2.4 Hz), 156.6 (dd, J=157.8, 2.4 Hz), 130.3 (dd, J=18.8, 7.6 Hz), 116.7 (dd, J=23.6, 5.4 Hz), 116.1 (dd, J=25.4, 8.8 Hz), 113.9 (dd, J=24.0, 8.5 Hz), 51.2, 28.5, 28.4, 27.0. $^{19}$F NMR (376 MHz, $CDCl_3$) δ −119.62 (d, J=17.6 Hz), −125.03 (d, J=17.6 Hz).

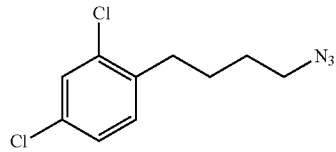 [SMILES: [N-]=[N+]=NCCCCc1ccc(Cl)cc1Cl]

1-(4-azidobutyl)-2,4-dichlorobenzene: Synthesized following the general procedures D, B and A from 2,4-dichloro-1-iodobenzene and obtained as a colorless oil (45% over four steps). $^1$H NMR (400 MHz, $CDCl_3$) δ 7.37 (d, J=2.0 Hz, 1H), 7.18 (dd, J=8.2, 2.0 Hz, 1H), 7.14 (d, J=8.2 Hz, 1H), 3.32 (t, J=6.4 Hz, 2H), 2.73 (t, J=7.3 Hz, 2H), 1.74-1.62 (m, 4H). $^{13}$C NMR (100 MHz, $CDCl_3$) δ 138.1, 134.5, 132.3, 131.1, 129.2, 127.1, 51.2, 32.5, 28.5, 26.8. HRMS (ESI) m/z: [M−N$_2$+H]$^+$ calcd. for [C$_{10}$H$_{12}$Cl$_2$N]$^+$ 216.0341, found: 216.0342.

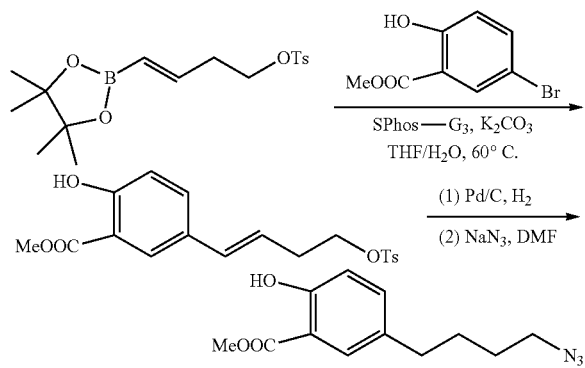

methyl (E)-2-hydroxy-5-(4-(tosyloxy)but-1-en-1-yl)benzoate: Synthesized following the reported general procedure for the Suzuki-Miyaura coupling reactions (X.-J. Dai, et al., *Angew. Chem. Int. Ed.*, 2019, 58, 3407) to provide the desired compound as a colorless oil (77%). $^1$H NMR (400 MHz, CDCl$_3$) δ 10.72 (s, 1H), 7.78 (d, J=8.3 Hz, 2H), 7.73 (d, J=2.1 Hz, 1H), 7.39 (dd, J=8.6, 2.2 Hz, 1H), 7.30 (d, J=8.4 Hz, 2H), 6.91 (d, J=8.6 Hz, 1H), 6.30 (d, J=15.9 Hz, 1H), 5.89 (dt, J=15.8, 7.0 Hz, 1H), 4.12 (t, J=6.5 Hz, 2H), 3.95 (s, 3H), 2.53 (q, J=6.5 Hz, 2H), 2.41 (s, 3H). $^{13}$C NMR (100 MHz, CDCl$_3$) δ 170.4, 160.9, 144.8, 133.1, 133.0, 131.8, 129.8, 128.5, 127.9, 127.5, 122.7, 117.8, 112.2, 69.7, 52.4, 32.4, 21.6.

methyl 5-(4-azidobutyl)-2-hydroxybenzoate: Synthesized following the general procedures B and A, and obtained as a colorless oil (28% over two steps). $^1$H NMR (400 MHz, CDCl$_3$) δ 10.60 (s, 1H), 7.62 (d, J=2.2 Hz, 1H), 7.25 (dd, J=8.5, 2.3 Hz, 1H), 6.89 (d, J=8.5 Hz, 1H), 3.92 (s, 3H), 3.26 (t, J=6.5 Hz, 2H), 2.55 (t, J=7.3 Hz, 2H), 1.71-1.55 (m, 4H). $^{13}$C NMR (100 MHz, CDCl$_3$) δ 170.5, 159.9, 135.9, 132.5, 129.1, 117.5, 112.0, 52.2, 51.3, 34.3, 28.5, 28.3. HRMS (ESI) m/z: [M−N$_2$+H]$^+$ calcd. for [C$_{12}$H$_{16}$NO$_3$]$^+$: 222.1125, found 222.1123.

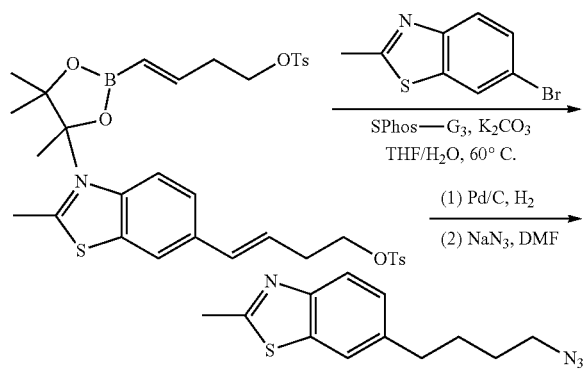

(E)-4-(2-methylbenzo[d]thiazol-6-yl)but-3-en-1-yl 4-methylbenzenesulfonate: Synthesized following the reported general procedure for the Suzuki-Miyaura coupling reactions (X.-J. Dai, et al., *Angew. Chem. Int. Ed.*, 2019, 58, 3407) using 6-bromo-2-methylbenzo[d]thiazole (600 mg, 2.6 mmol, 1.0 equiv.), (E)-4-(4,4,5,5-tetramethyl-1,3,2-dioxaborolan-2-yl)but-3-en-1-yl 4-methylbenzenesulfonate (C.-B. Yi, et al., *Org. Lett.*, 2018, 20, 668) (1.21 g, 3.45 mmol, 1.3 equiv.), SPhos-G3 (99 mg, 0.132 mmol, 0.05 equiv.), and K$_2$CO$_3$ (1.09 g, 7.89 mmol, 3.0 equiv.) in THF/H$_2$O=3:1 (0.3 M) at 60° C. for 6 h. The crude residue was purified by column chromatography to provide the desired compound as a colorless oil (600 mg, 61%). $^1$H NMR (400 MHz, Chloroform-d) δ 7.79 (dd, J=8.4, 3.3 Hz, 1H), 7.76-7.70 (m, 2H), 7.61 (d, J=2.7 Hz, 1H), 7.33-7.27 (m, 1H), 7.25-7.19 (m, 2H), 6.40 (d, J=15.8 Hz, 1H), 6.05-5.91 (m, 1H), 4.11 (t, J=6.4 Hz, 2H), 2.76 (s, 3H), 2.57-2.47 (m, 2H), 2.33 (s, 3H). $^{13}$C NMR (100 MHz, CDCl$_3$) δ 167.2, 152.6, 144.8, 136.1, 133.9, 132.9, 132.6, 129.8, 127.9, 124.5, 124.2, 122.1, 118.9, 69.6, 32.5, 21.6, 20.1. HRMS (ESI) m/z: [M+H]$^+$ calcd. for [C$_{19}$H$_{20}$NO$_3$S$_2$]$^+$: 374.0879, found 374.0876.

6-(4-azidobutyl)-2-methylbenzo[d]thiazole: Synthesized following the general procedures B and A, and obtained as a colorless oil (97% over two steps). $^1$H NMR (400 MHz, CDCl$_3$) δ 7.78 (d, J=8.3 Hz, 1H), 7.49 (s, 1H), 7.14 (dd, J=8.3, 1.4 Hz, 1H), 3.15 (t, J=6.7 Hz, 2H), 2.69 (s, 3H), 2.62 (t, J=7.5 Hz, 2H), 1.68-1.56 (m, 2H), 1.55-1.46 (m, 2H). $^{13}$C NMR (100 MHz, CDCl$_3$) δ 166.0, 151.8, 138.7, 135.9, 126.6, 122.0, 120.6, 51.2, 35.2, 28.6, 28.4, 20.0. HRMS (ESI) m/z: [M+H]$^+$ calcd. for [C$_{12}$H$_{15}$N$_4$S]$^+$: 247.1012, found 247.1009.

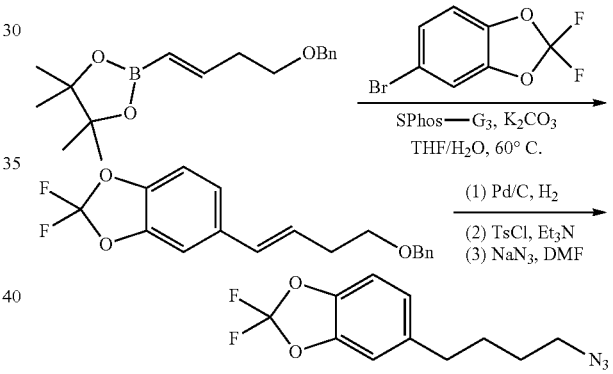

(E)-5-(4-(benzyloxy)but-1-en-1-yl)-2,2-difluorobenzo[d][1,3]dioxole: Synthesized following the reported general procedure for the Suzuki-Miyaura coupling reactions (X.-J. Dai, et al., *Angew. Chem. Int. Ed.*, 2019, 58, 3407) using 5-bromo-2,2-difluorobenzo[d][1,3]dioxol (600 mg, 2.53 mmol, 1.0 equiv.), (E)-2-(4-(benzyloxy)but-1-en-1-yl)-4,4,5,5-tetramethyl-1,3,2-dioxaborolane (C.-B. Yi, et al., *Org. Lett.*, 2018, 20, 668) (947 mg, 3.29 mmol, 1.3 equiv.), SPhos-G3 (94.8 mg, 0.126 mmol, 0.05 equiv.) and K$_2$CO$_3$ (1.047 g, 7.59 mmol, 3.0 equiv.) in THF/H$_2$O=3:1 (0.3 M) at 60° C. for 6 h. The crude residue was purified by column chromatography to provide the desired compound (668 mg, 83%) as a colorless oil. $^1$H NMR (400 MHz, CDCl$_3$) δ 7.43-7.28 (m, 5H), 7.09 (d, J=1.5 Hz, 1H), 7.00 (dd, J=8.3, 1.5 Hz, 1H), 6.97 (d, J=8.2 Hz, 1H), 6.42 (d, J=15.9 Hz, 1H), 6.17 (dt, J=15.9, 6.9 Hz, 1H), 4.57 (s, 2H), 3.62 (t, J=6.6 Hz, 2H), 2.55 (qd, J=6.7, 1.3 Hz, 2H). $^{13}$C NMR (100 MHz, CDCl$_3$) δ 144.3, 142.9, 138.5, 134.4, 131.8 (t, J=254.8 Hz), 130.5, 128.6, 127.9, 127.8, 127.8, 122.0, 109.4, 106.6, 73.2, 69.7, 33.5. $^{19}$F NMR (376 MHz, CDCl$_3$) δ −50.24.

5-(4-azidobutyl)-2,2-difluorobenzo[d][1,3]dioxole: Synthesized following the general procedures B and A, and obtained as a colorless oil (21% over three steps). $^1$H NMR (400 MHz, CDCl$_3$) δ 6.95 (d, J=8.1 Hz, 1H), 6.91-6.84 (m, 2H), 3.29 (t, J=6.6 Hz, 2H), 2.64 (t, J=7.4 Hz, 2H), 1.75-1.56 (m, 4H). $^{13}$C NMR (100 MHz, CDCl$_3$) δ 143.8, 142.0, 138.1, 131.7 (t, J=254.1 Hz), 123.2, 109.5, 109.1, 51.2, 35.1, 28.6, 28.3. $^{19}$F NMR (376 MHz, CDCl$_3$) δ −50.12. HRMS (ESI) m/z: [M−N$_2$+H]$^+$ calcd. for [C$_{11}$H$_{12}$F$_2$NO$_2$]$^+$: 228.0831, found 228.0829.

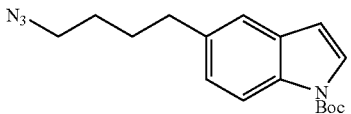 [SMILES: CC(C)(C)OC(=O)n1ccc2cc(CCCCN=[N+]=[N-])ccc21]

tert-butyl 5-(4-azidobutyl)-1H-indole-1-carboxylate: Synthesized following the general procedures D, B and A from tert-butyl 5-iodo-1H-indole-1-carboxylate (J. E. Jakobsson, et al., *Chem. Commun.*, 2017, 53, 12906) and obtained as a colorless oil (68% over four steps). $^1$H NMR (400 MHz, CDCl$_3$) δ 8.04 (d, J=8.1 Hz, 1H), 7.56 (d, J=3.4 Hz, 1H), 7.34 (s, 1H), 7.12 (d, J=8.4 Hz, 1H), 6.50 (d, J=3.6 Hz, 1H), 3.27 (t, J=6.8 Hz, 2H), 2.73 (t, J=7.4 Hz, 2H), 1.83-1.56 (m, 4H+9H). $^{13}$C NMR (100 MHz, CDCl$_3$) δ 149.9, 136.3, 133.8, 130.9, 126.2, 125.0, 120.4, 115.1, 107.2, 83.6, 51.5, 35.3, 29.0, 28.5, 28.3. HRMS (ESI) m/z: [M−N$_2$+H]$^+$ calcd. for [C$_{17}$H$_{23}$N$_2$O$_2$]$^+$: 287.1754, found 287.1752.

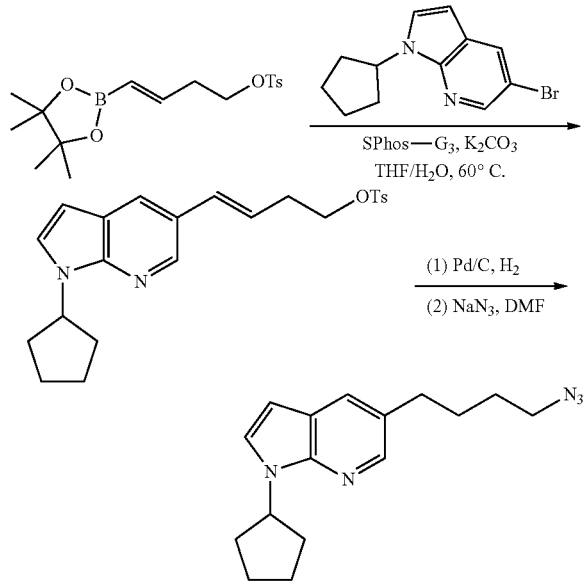

(E)-4-(1-cyclopentyl-1H-pyrrolo[2,3-b]pyridin-5-yl)but-3-en-1-yl 4-methylbenzenesulfonate: Synthesized following the reported general procedure for the Suzuki-Miyaura coupling reactions (X.-J. Dai, et al., *Angew. Chem. Int. Ed.*, 2019, 58, 3407) from 5-bromo-1-cyclopentyl-1H-pyrrolo[2,3-b]pyridine (M. Chen, S. Ichikawa and S. L. Buchwald, *Angew. Chem. Int. Ed.*, 2015, 54, 263) to provide the desired compound as a colorless oil (46%). $^1$H NMR (400 MHz, CDCl$_3$) δ 8.22 (d, J=2.0 Hz, 1H), 7.82-7.74 (m, 3H), 7.29-7.26 (m, 2H), 7.25 (s, 1H), 6.47 (d, J=15.9 Hz, 1H), 6.41 (d, J=3.6 Hz, 1H), 5.95 (dt, J=15.9, 7.0 Hz, 1H), 5.38-5.17 (m, 1H), 4.15 (t, J=6.6 Hz, 2H), 2.65-2.50 (m, 2H), 2.35 (s, 3H), 2.27-2.17 (m, 2H), 1.96-1.67 (m, 6H). $^{13}$C NMR (100 MHz, CDCl$_3$) δ 147.3, 144.8, 141.8, 133.1, 131.3, 129.8, 127.9, 125.7, 125.3, 125.1, 122.3, 120.6, 99.7, 69.9, 55.0, 32.9, 32.6, 24.1, 21.6.

5-(4-azidobutyl)-1-cyclopentyl-1H-pyrrolo[2,3-b]pyridine: Synthesized following the general procedure B and A, and obtained as a colorless oil (69% over two steps). $^1$H NMR (400 MHz, CDCl$_3$) δ 8.15 (d, J=1.9 Hz, 1H), 7.66 (d, J=1.9 Hz, 1H), 7.24 (d, J=3.5 Hz, 1H), 6.37 (d, J=3.5 Hz, 1H), 5.35-5.18 (m, 1H), 3.23 (t, J=6.7 Hz, 2H), 2.69 (t, J=7.4 Hz, 2H), 2.28-2.13 (m, 2H), 1.89-1.79 (m, 4H), 1.78-1.65 (m, 4H), 1.64-1.56 (m, 2H). $^{13}$C NMR (100 MHz, CDCl$_3$) δ 146.7, 143.1, 128.6, 128.0, 125.1, 120.6, 99.0, 54.9, 51.3, 32.9, 32.6, 29.1, 28.3, 24.1. HRMS (ESI) m/z: [M+H]$^+$ calcd. for [C$_{16}$H$_{22}$N$_5$]$^+$: 284.1870, found 284.1867.

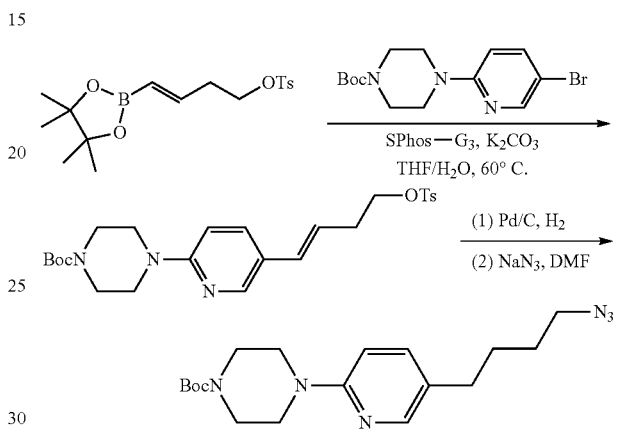

tert-butyl (E)-4-(5-(4-(tosyloxy)but-1-en-1-yl)pyridin-2-yl)piperazine-1-carboxylate: Synthesized following the reported general procedure for the Suzuki-Miyaura coupling reactions (X.-J. Dai, et al., *Angew. Chem. Int. Ed.*, 2019, 58, 3407) to provide the desired compound as a colorless oil (39%). $^1$H NMR (400 MHz, CDCl$_3$) δ 8.04 (d, J=2.2 Hz, 1H), 7.78 (d, J=8.3 Hz, 2H), 7.48 (dd, J=8.8, 2.4 Hz, 1H), 7.31 (d, J=8.1 Hz, 2H), 6.60 (d, J=8.8 Hz, 1H), 6.27 (d, J=15.9 Hz, 1H), 5.83 (dt, J=15.8, 7.0 Hz, 1H), 4.12 (t, J=6.6 Hz, 2H), 3.53 (s, 8H), 2.53 (q, J=6.3 Hz, 2H), 2.43 (s, 3H), 1.49 (s, 9H). $^{13}$C NMR (100 MHz, CDCl$_3$) δ 158.5, 154.8, 146.6, 144.8, 134.4, 133.1, 129.8, 129.8, 127.9, 122.9, 121.5, 107.0, 80.0, 69.8, 45.1, 45.1, 32.6, 28.4, 21.7. HRMS (ESI) m/z: [M+H]$^+$ calcd. for [C$_{25}$H$_{34}$N$_3$O$_5$S]$^+$: 488.2214, found 488.2214.

tert-butyl 4-(5-(4-azidobutyl)pyridin-2-yl)piperazine-1-carboxylate: Synthesized following the general procedure B and A, and obtained as a colorless oil (40% over two steps). $^1$H NMR (400 MHz, CDCl$_3$) δ 8.01 (d, J=1.8 Hz, 1H), 7.33 (dd, J=8.5, 2.2 Hz, 1H), 6.61 (d, J=8.6 Hz, 1H), 3.57-3.51 (m, 4H), 3.50-3.44 (m, 4H), 3.27 (t, J=6.3 Hz, 2H), 2.52 (t, J=6.9 Hz, 2H), 1.68-1.57 (m, 4H), 1.48 (s, 9H). $^{13}$C NMR (100 MHz, CDCl$_3$) δ 158.1, 154.8, 147.4, 137.7 126.6, 107.2, 79.8, 51.2, 45.4, 31.4, 28.4, 28.4, 28.2. HRMS (ESI) m/z: [M+H]$^+$ calcd. for [C$_{18}$H$_{29}$N$_6$O$_2$]$^+$: 361.2347, found 361.2343.

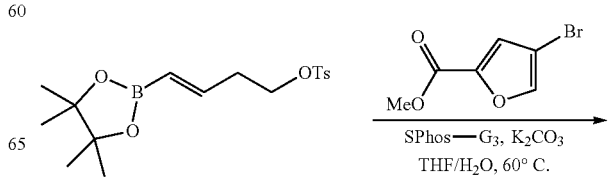

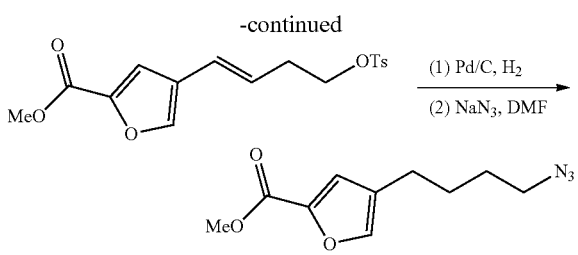

methyl (E)-4-(4-(tosyloxy)but-1-en-1-yl)furan-2-carboxylate: Synthesized following the reported general procedure for the Suzuki-Miyaura coupling reactions (X.-J. Dai, et al., *Angew. Chem. Int. Ed.*, 2019, 58, 3407) to provide the desired compound as a colorless oil (44%). $^1$H NMR (400 MHz, CDCl$_3$) δ 7.78 (d, J=8.3 Hz, 2H), 7.46 (s, 1H), 7.33 (d, J=8.0 Hz, 2H), 7.17 (s, 1H), 6.21 (d, J=15.9 Hz, 1H), 5.80 (dt, J=15.8, 7.0 Hz, 1H), 4.11 (t, J=6.4 Hz, 2H), 3.90 (s, 3H), 2.51 (q, J=6.4 Hz, 2H), 2.44 (s, 3H). $^{13}$C NMR (100 MHz, CDCl$_3$) δ 159.0, 144.9, 144.9, 143.1, 133.0, 129.9, 127.9, 125.7, 121.7, 115.3, 69.3, 52.0, 32.3, 21.6. HRMS (ESI) m/z: [M+H]$^+$ calcd. for [C$_{17}$H$_{19}$O$_6$S]$^+$: 351.0897, found 351.0894.

methyl 4-(4-azidobutyl)furan-2-carboxylate: Synthesized following the general procedure B and A, and obtained as a colorless oil (53% over two steps). $^1$H NMR (400 MHz, CDCl$_3$) δ 7.29 (s, 1H), 6.98 (s, 1H), 3.79 (s, 3H), 3.21 (t, J=6.1 Hz, 2H), 2.39 (t, J=6.8 Hz, 2H), 1.60-1.50 (m, 4H). $^{13}$C NMR (100 MHz, CDCl$_3$) δ 159.1, 144.5, 142.9, 126.9, 118.8, 51.7, 51.1, 28.2, 26.8, 24.0. HRMS (ESI) m/z: [M–N$_2$+H]$^+$ calcd. for [C$_{10}$H$_{14}$NO$_3$]$^+$: 196.0968, found 196.0968.

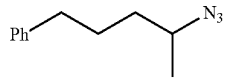

(4-azidopentyl)benzene: Synthesized following the general procedure A from 5-phenylpentan-2-ol (H. Ito, et al., *Org. Lett.*, 2012, 14, 890) and obtained as a colorless oil (58% over two steps). $^1$H NMR (400 MHz, CDCl$_3$) δ 7.31-7.14 (m, 5H), 3.50-3.38 (m, 1H), 2.62 (t, J=7.6 Hz, 2H), 1.82-1.62 (m, 2H), 1.59-1.45 (m, 2H), 1.24 (d, J=6.5 Hz, 3H). $^{13}$C NMR (100 MHz, CDCl$_3$) δ 142.0, 128.4, 125.9, 57.9, 35.8, 35.6, 27.9, 19.5. HRMS (ESI) m/z: [M–N$_2$+H]$^+$ calcd. for [C$_{11}$H$_{16}$N]$^+$: 162.1277, found 162.1277.

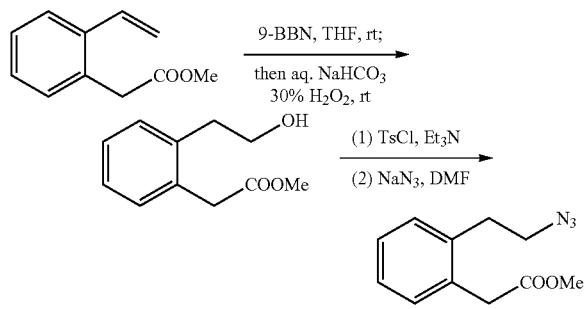

methyl 2-(2-(2-hydroxyethyl)phenyl)acetate: Synthesized following the reported procedure (H. Fuwa, et al., *Heterocycles*, 2008, 76, 521). To a flask containing methyl 2-(2-vinylphenyl)acetate (N. Su, et al., *Angew. Chem. Int. Ed.*, 2015, 54, 12942) (1.19 g, 6.75 mmol) was added 9-BBN (0.5 M solution in THF, 27 mL, 13.5 mmol), and the solution was stirred at rt for several hours until TLC completion. The resultant mixture was cooled to 0° C. and treated with saturated aqueous NaHCO$_3$ (27 mL) and 30% H$_2$O$_2$ (10 mL). After being stirred at rt overnight, the resultant mixture was extracted with EtOAc, washed with saturated aqueous Na$_2$SO$_3$ and brine, dried over Na$_2$SO$_4$, filtered, and concentrated under reduced pressure. Purification of the residue by silica gel flash chromatography gave alcohol (824 mg, 63%) as a colorless oil. $^1$H NMR (400 MHz, CDCl$_3$) δ 7.25-7.17 (m, 4H), 3.81 (t, J=6.7 Hz, 2H), 3.71 (s, 2H), 3.68 (s, 3H), 2.90 (t, J=6.7 Hz, 2H), 2.13 (br s, 1H).

methyl 2-(2-(2-azidoethyl)phenyl)acetate: Synthesized following the general procedure A from methyl methyl 2-(2-(2-hydroxyethyl)phenyl)acetate and obtained as a colorless oil (86% over two steps). $^1$H NMR (500 MHz, CDCl$_3$) δ 7.29-7.19 (m, 4H), 3.70 (s, 3H), 3.69 (s, 2H), 3.50 (t, J=7.4 Hz, 2H), 2.94 (t, J=7.4 Hz, 2H). $^{13}$C NMR (125 MHz, CDCl$_3$) δ 171.9, 136.6, 132.7, 131.0, 129.9, 127.8, 127.3, 52.2, 51.9, 38.6, 32.3. HRMS (ESI) m/z: [M+Na]$^+$ calcd. for [C$_{11}$H$_{13}$N$_3$NaO$_2$]$^+$: 242.0900, found 242.0901.

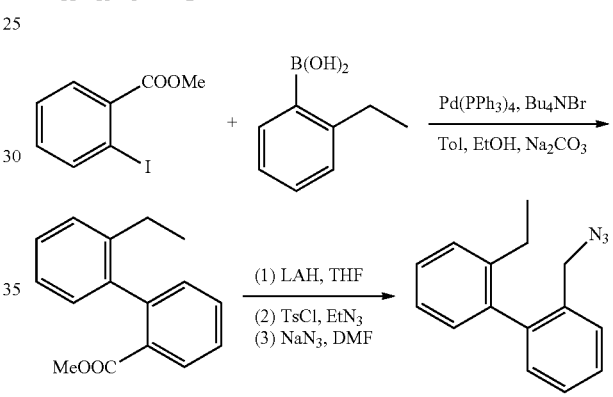

methyl 2'-ethyl-[1,1'-biphenyl]-2-carboxylate: A mixture of methyl 2-iodobenzoate (524 mg, 2 mmol), (2-ethylphenyl)boronic acid (450 mg, 3 mmol, 1.5 equiv.), toluene (15 mL), ethanol (6 mL) and 2 M Na$_2$CO$_3$ (2 mL, 4 mmol, 2 equiv.) was degassed, then Pd(PPh$_3$)$_4$ (115.5 mg, 0.1 mmol, 0.05 equiv.) and Bu$_4$NBr (32 mg, 0.1 mmol, 0.05 equiv.) were added under Ar. The mixture was heated at 95° C. for 3-4 h, then stirred overnight at room temperature. The reaction was diluted with water and extracted with ethyl acetate. The combined extracts were washed with brine, dried over anhydrous Na$_2$SO$_4$, filtered and evaporated. The product was purified by silica gel chromatography to provide the desired product as a colorless oil (388 mg, 81%). $^1$H NMR (500 MHz, CDCl$_3$) δ 7.96 (dd, J=7.8, 1.4 Hz, 1H), 7.56-7.49 (m, 1H), 7.42 (td, J=7.6, 1.3 Hz, 1H), 7.36-7.24 (m, 3H), 7.19 (td, J=7.1, 2.1 Hz, 1H), 7.05 (d, J=8.0 Hz, 1H), 3.59 (s, 3H), 2.49-2.31 (m, 2H), 1.03 (t, J=7.5 Hz, 3H). $^{13}$C NMR (125 MHz, CDCl$_3$) δ 167.8, 142.8, 141.2, 140.9, 131.4, 131.2, 130.0, 128.7, 127.8, 127.5, 127.1, 125.1, 51.8, 26.2, 14.9. HRMS (ESI) m/z: [M+H]$^+$ calcd. for [C$_{16}$H$_{17}$O$_2$]$^+$: 241.1223, found 241.1221.

2-(azidomethyl)-2'-ethyl-1,1'-biphenyl: Synthesized following the general procedures C and A, and obtained as a colorless oil (56% over three steps). $^1$H NMR (500 MHz, CDCl$_3$) δ 7.46 (d, J=7.4 Hz, 1H), 7.42-7.31 (m, 4H), 7.26-7.19 (m, 2H), 7.10 (d, J=7.3 Hz, 1H), 4.15-4.05 (m, 2H), 2.46-2.26 (m, 2H), 1.04 (t, J=7.6 Hz, 3H). $^{13}$C NMR (125 MHz, CDCl$_3$) δ 141.9, 141.2, 139.0, 133.5, 130.2, 129.7, 128.8, 128.4, 128.1, 127.9, 127.8, 125.6, 52.5, 26.2, 15.2. HRMS (ESI) m/z: [M−N$_2$+H]$^+$ calcd. for [C$_{15}$H$_{16}$N]$^+$: 210.1277, found 210.1277.

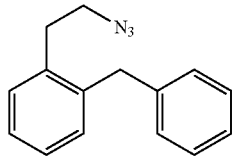 [SMILES: [N-]=[N+]=NCCc1ccccc1Cc1ccccc1]

1-(2-azidoethyl)-2-benzylbenzene: Synthesized following the general procedure A from 2-(2-benzylphenyl)ethan-1-ol (M. Yus, et al., *Tetrahedron Lett.*, 2001, 42, 5721) and obtained as a colorless oil (87% over two steps). $^1$H NMR (400 MHz, CDCl$_3$) δ 7.32-7.05 (m, 9H), 4.04 (s, 2H), 3.22 (t, J=7.6 Hz, 2H), 2.86 (t, J=7.6 Hz, 2H). $^{13}$C NMR (100 MHz, CDCl$_3$) δ 140.6, 138.8, 136.4, 131.0, 130.0, 128.6, 128.6, 127.1, 126.2, 51.8, 39.2, 32.3. HRMS (ESI) m/z: [M+H]$^+$ calcd. for [C$_{15}$H$_{16}$N$_3$]$^+$: 238.1339. found 238.1336.

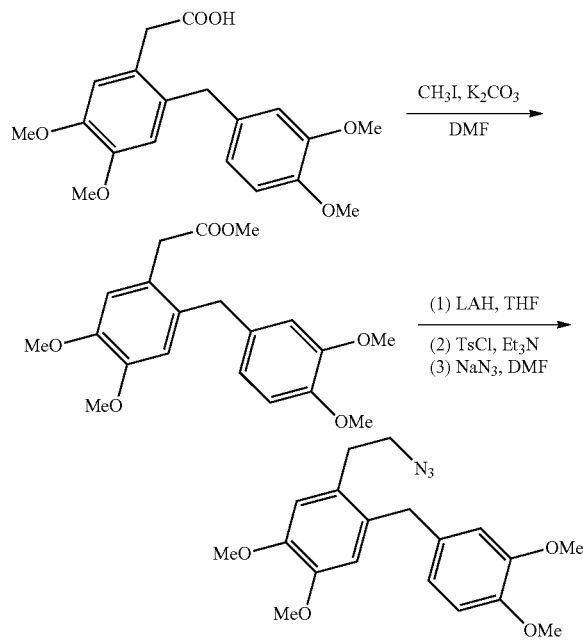

methyl 2-(2-(3,4-dimethoxybenzyl)-4,5-dimethoxyphenyl)acetate: To a stirred mixture of 2-(2-(3,4-dimethoxybenzyl)-4,5-dimethoxyphenyl)acetic acid (C. Legros, et al., *Int. J. Mol. Sci.*, 2013, 14, 8948) (2.5 g, 7.22 mmol, 1.0 equiv.) and K$_2$CO$_3$ (3 g, 21.7 mmol, 3.0 equiv.) in DMF (20 mL), methyl iodide (0.9 mL, 14.44 mmol, 2.0 equiv.) was added at room temperature, and then the reaction mixture was stirred at room temperature for 5 h. After completion the mixture was diluted by 100 mL H$_2$O. The aqueous layer was extracted three times with ethyl acetate. The combined organic layers were washed twice with brine, dried over Na$_2$SO$_4$, and evaporated to dryness, and the residue was purified by silica gel flash chromatography to give the desired compound as an off-white solid (2.4 g, 92%). $^1$H NMR (400 MHz, CDCl$_3$) δ 6.79-6.76 (m, 2H), 6.67-6.63 (m, 2H), 6.61 (d, J=8.3 Hz, 1H), 3.93 (s, 2H), 3.88 (s, 3H), 3.85 (s, 3H), 3.81 (s, 3H), 3.80 (s, 3H), 3.62 (s, 3H), 3.54 (s, 2H).

$^{13}$C NMR (100 MHz, CDCl$_3$) δ 172.2, 148.9, 148.1, 147.4, 147.3, 133.0, 131.6, 124.8, 120.5, 113.9, 113.7, 111.9, 111.2, 56.0, 55.9, 55.8, 52.0, 38.2, 38.1.

1-(2-azidoethyl)-2-(3,4-dimethoxybenzyl)-4,5-dimethoxybenzene: Synthesized following the general procedures C and A and obtained as a colorless oil (58% over three steps). $^1$H NMR (400 MHz, CDCl$_3$) δ 6.77 (d, J=8.2 Hz, 1H), 6.72 (s, 1H), 6.68 (s, 1H), 6.65 (d, J=1.8 Hz, 1H), 6.61 (dd, J=8.2, 1.8 Hz, 1H), 3.92 (s, 2H), 3.87 (s, 3H), 3.83 (s, 3H), 3.81 (s, 3H), 3.80 (s, 3H), 3.23 (t, J=7.5 Hz, 2H), 2.81 (t, J=7.5 Hz, 2H). $^{13}$C NMR (100 MHz, CDCl$_3$) δ 149.0, 147.7, 147.6, 147.4, 133.4, 131.1, 128.4, 120.4, 114.0, 113.3, 111.8, 111.3, 56.0, 55.9, 55.9, 55.8, 51.9, 38.2, 32.1. HRMS (ESI) m/z: [M+Na]$^+$ calcd. for [C$_{19}$H$_{23}$N$_3$O$_4$Na]$^+$: 380.1581, found 380.1580.

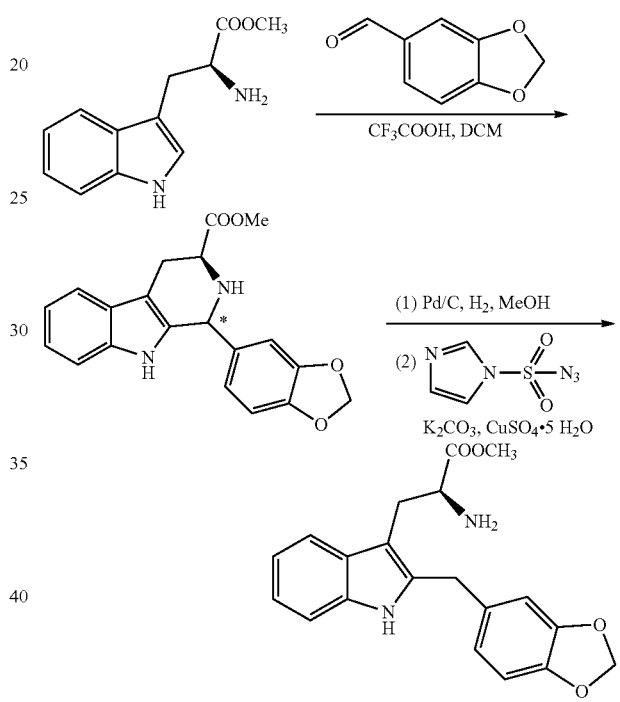

methyl (S)-1-(benzo[d][1,3]dioxol-5-yl)-2,3,4,9-tetrahydro-1H-1λ$^3$-pyrido[3,4-b]indole-3-carboxylate: Trifluoroacetic acid (1.02 g, 8.93 mmol, 1.5 equiv.) was added to a solution of (S)-tryptophan methyl ester (J. Ruchti, et al., *J. Am. Chem. Soc.*, 2014, 136, 16756) (1.3 g, 5.96 mmol, 1.0 equiv.) and benzo[d][1,3]dioxole-5-carbaldehyde (1.08 g, 7.15 mmol, 1.2 equiv.) in DCM (20 mL). The reaction mixture was stirred for 1 day at room temperature and then evaporated. The obtained residue was triturated with a 5% K$_2$CO$_3$ aqueous solution (30 mL) and extracted with DCM. The organic layer was dried over MgSO$_4$ and evaporated to dryness under reduced pressure. The crude product was purified by column chromatography to afford the desired products as isomers (76%). The isolated ratio of the two isomers is nearly 1:1. Isomer a $^1$H NMR (400 MHz, CDCl$_3$) δ 7.59-7.50 (m, 2H), 7.24-7.19 (m, 1H), 7.18-7.09 (m, 2H), 6.87 (dd, J=7.8, 1.7 Hz, 1H), 6.82 (d, J=1.7 Hz, 1H), 6.79 (d, J=7.9 Hz, 1H), 5.94 (s, 2H), 5.15 (t, J=2.1 Hz, 1H), 3.94 (dd, J=11.1, 4.2 Hz, 1H), 3.81 (s, 3H), 3.21 (ddd, J=15.0, 4.2, 1.8 Hz, 1H), 3.06-2.94 (m, 1H), 2.43 (br s, 1H). $^{13}$C NMR (100 MHz, CDCl$_3$) δ 173.3, 148.3, 148.0, 136.3, 134.9, 134.8, 127.3, 122.1, 119.8, 118.4, 111.1, 109.0, 108.9, 108.5, 101.4, 58.6, 57.0, 52.4, 25.8. HRMS (ESI) m/z: [M+H]$^+$ calcd. for [C$_{20}$H$_{19}$N$_2$O$_4$]$^+$: 351.1339, found 351.1333. Isomer b $^1$H NMR (400 MHz, CDCl$_3$) δ 7.91-7.73 (m, 1H), 7.55 (d, J=7.3 Hz, 1H), 7.22 (d, J=7.4 Hz, 1H), 7.19-7.09 (m, 2H), 6.78-6.67 (m, 3H), 5.90 (s, 2H), 5.31-5.25 (m, 1H), 3.96 (t, J=6.0 Hz, 1H), 3.71 (s, 3H), 3.25 (dd, J=15.4, 5.4 Hz, 1H), 3.10 (dd, J=15.3, 6.7 Hz, 1H), 2.37 (br s, 1H). $^{13}$C NMR (100 MHz, CDCl$_3$) δ 174.2, 148.1, 147.4, 136.2, 136.1, 133.3, 127.0, 122.0, 121.7, 119.5, 118.3, 111.0, 108.7, 108.3, 108.1, 101.2, 54.7, 52.5, 52.1, 24.7. HRMS (ESI) m/z: [M+H]$^+$ calcd. for [C$_{20}$H$_{19}$N$_2$O$_4$]$^+$: 351.1339, found 351.1331.

methyl (S)-2-azido-3-(2-(benzo[d][1,3]dioxol-5-ylmethyl)-1H-indol yl)propanoate: Step 1. To a solution of the above isomers (600 mg, 1.72 mmol) in MeOH (50 mL) was added 10% Pd/C (60 mg). The resulting solution was stirred at 50° C. under atmospheric pressure of hydrogen for 3 days. The solution was concentrated to dryness. The residue was purified by column chromatography to afford methyl (S)-2-amino-3-(2-(benzo[d][1,3]dioxol-5-ylmethyl)-1H-indol yl)propanoate as an off-white solid (450 mg, 74%). $^1$H NMR (400 MHz, CDCl$_3$) δ 8.11 (s, 1H), 7.57 (d, J=7.2 Hz, 1H), 7.20 (d, J=7.5 Hz, 1H), 7.16-7.07 (m, 2H), 6.73 (d, J=8.2 Hz, 1H), 6.67-6.61 (m, 2H), 5.90 (s, 2H), 4.01 (s, 2H), 3.83 (dd, J=7.9, 5.2 Hz, 1H), 3.70 (s, 3H), 3.30 (dd, J=14.3, 5.1 Hz, 1H), 3.04 (dd, J=14.3, 8.1 Hz, 1H). $^{13}$C NMR (100 MHz, CDCl$_3$) δ 175.9, 148.0, 146.4, 135.6, 135.3, 132.3, 128.5, 121.6, 121.5, 119.5, 118.4, 110.7, 109.1, 108.4, 107.6, 101.0, 55.4, 52.1, 32.0, 30.1. HRMS (ESI) m/z: [M+H]$^+$ calcd. for [C$_{20}$H$_{21}$N$_2$O$_4$]$^+$: 353.1496, found 353.1489. Step 2. Synthesized following the reported procedures (E. D. Goddard-Borger, et al., Org. Lett., 2007, 9, 3797), and the desired azide was afforded as a brown oil (68%). $^1$H NMR (400 MHz, CDCl$_3$) δ 7.77 (s, 1H), 7.56-7.49 (m, 1H), 7.23-7.18 (m, 1H), 7.15-7.07 (m, 2H), 6.74 (d, J=7.7 Hz, 1H), 6.66 (d, J=7.8 Hz, 2H), 5.89 (s, 2H), 4.17 (dd, J=8.5, 5.5 Hz, 1H), 4.03 (s, 2H), 3.73 (s, 3H), 3.36 (dd, J=14.6, 5.5 Hz, 1H), 3.15 (dd, J=14.6, 8.5 Hz, 1H). $^{13}$C NMR (100 MHz, CDCl$_3$) δ 170.9, 148.1, 146.5, 135.6, 135.5, 132.0, 128.1, 121.8, 121.7, 119.7, 118.0, 110.8, 109.2, 108.5, 106.5, 101.1, 62.7, 52.7, 32.0, 27.2. HRMS (ESI) m/z: [M+H]$^+$ calcd. for [C$_{20}$H$_{19}$N$_4$O$_4$]$^+$: 379.1401, found 379.1395.

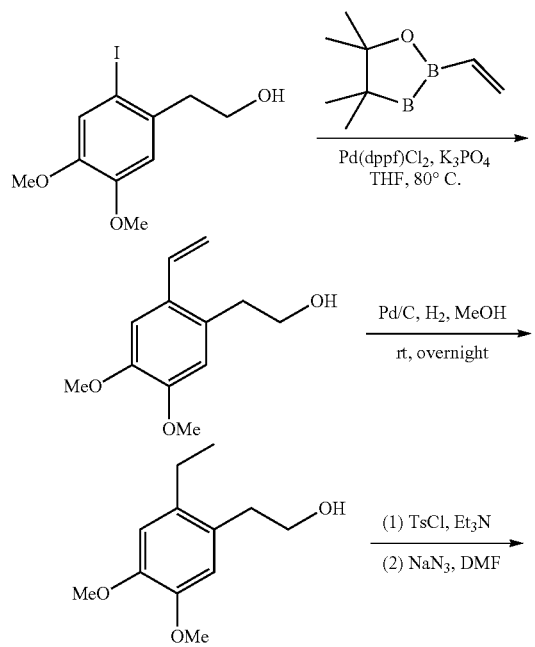

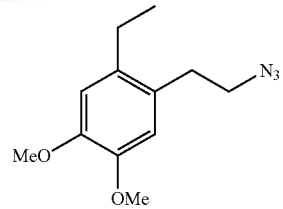

2-(4,5-dimethoxy-2-vinylphenyl)ethan-1-ol: Synthesized following the reported procedure (H. Liu, et al., Org. Lett., 2015, 17, 4444) from 2-(2-iodo-4,5-dimethoxyphenyl)ethan-1-ol (J. Ruiz, et al., Tetrahedron, 2005, 61, 3311). To a solution of vinylboronic acid pinacol cyclic ester (274 mg, 1.78 mmol, 2.2 equiv.) in THF (10 mL) was added H$_2$O (0.3 mL), PdCl$_2$(dppf) (11.8 mg, 0.016 mmol, 0.02 equiv.), K$_3$PO$_4$ (515 mg, 2.4, 3 equiv. mmol) in sequence. The resulting suspension was stirred for 15 min and then added 2-(2-iodo-4,5-dimethoxyphenyl)ethan-1-ol (250 mg, 0.811 mmol). The reaction mixture was warmed to 80° C. and stirred overnight and then was diluted with H$_2$O (20 mL). The organic layer was collected, and the aqueous layer was further extracted with ethyl acetate (3×20 mL). The combined organic layers were washed with NaCl (saturated aq., 50 mL), dried over Na$_2$SO$_4$, filtered and concentrated in vacuo. The residue was subjected to purification by column chromatography on silica gel to afford desired product as a yellow oil (157 mg, 93% yield). $^1$H NMR (400 MHz, CDCl$_3$) δ 7.01 (s, 1H), 6.92 (dd, J=17.3, 10.9 Hz, 1H), 6.68 (s, 1H), 5.54 (d, J=17.3 Hz, 1H), 5.19 (d, J=11.0 Hz, 1H), 3.86 (s, 3H), 3.84 (s, 3H), 3.73 (t, J=7.2 Hz, 2H), 2.92 (br, 1H), 2.88 (t, J=7.1 Hz, 2H). $^{13}$C NMR (100 MHz, CDCl$_3$) δ 148.6, 147.5, 133.7, 128.9, 128.5, 113.4, 113.1, 108.4, 63.0, 55.7, 35.8, 24.5. HRMS (ESI) m/z: [M+H]$^+$ calcd. for [C$_{12}$H$_{17}$O$_3$]$^+$: 209.1172, found 209.1170.

2-(2-ethyl-4,5-dimethoxyphenyl)ethan-1-ol: Synthesized following the general procedure B and the desired product was afforded as a yellow oil (69%) after flash chromatography. $^1$H NMR (400 MHz, CDCl$_3$) δ 6.73-6.66 (m, 2H), 3.83 (s, 3H), 3.82 (s, 3H), 3.76 (t, J=7.2 Hz, 2H), 2.96 (br, 1H), 2.82 (t, J=7.2 Hz, 2H), 2.59 (q, J=7.5 Hz, 2H), 1.19 (t, J=7.6 Hz, 3H). $^{13}$C NMR (100 MHz, CDCl$_3$) δ 147.5, 146.8, 134.8, 127.8, 113.4, 112.2, 63.4, 55.9, 55.9, 35.5, 25.3, 15.9. HRMS (ESI) m/z: [M+H]$^+$ calcd. for [C$_{12}$H$_{19}$O$_3$]$^+$: 211.1329, found 211.1325.

1-(2-azidoethyl)-2-ethyl-4,5-dimethoxybenzene: Synthesized following the general procedure A from 2-(2-ethyl-4,5-dimethoxyphenyl)ethan-1-ol and obtained as a colorless oil (59% over two steps). $^1$H NMR (400 MHz, CDCl$_3$) δ 6.70 (s, 1H), 6.67 (s, 1H), 3.85 (s, 3H), 3.84 (s, 3H), 3.42 (t, J=7.5 Hz, 2H), 2.85 (t, J=7.5 Hz, 2H), 2.59 (q, J=7.6 Hz, 2H), 1.21 (t, J=7.6 Hz, 3H). $^{13}$C NMR (100 MHz, CDCl$_3$) δ 147.9, 147.1, 134.6, 127.2, 113.0, 112.2, 56.0, 55.9, 52.3, 31.8, 25.3, 15.8. HRMS (ESI) m/z: [M–N$_2$+H]$^+$ calcd. for [C$_{12}$H$_{18}$NO$_2$]$^+$: 208.1332, found 208.1330.

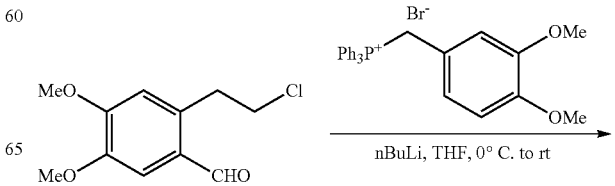

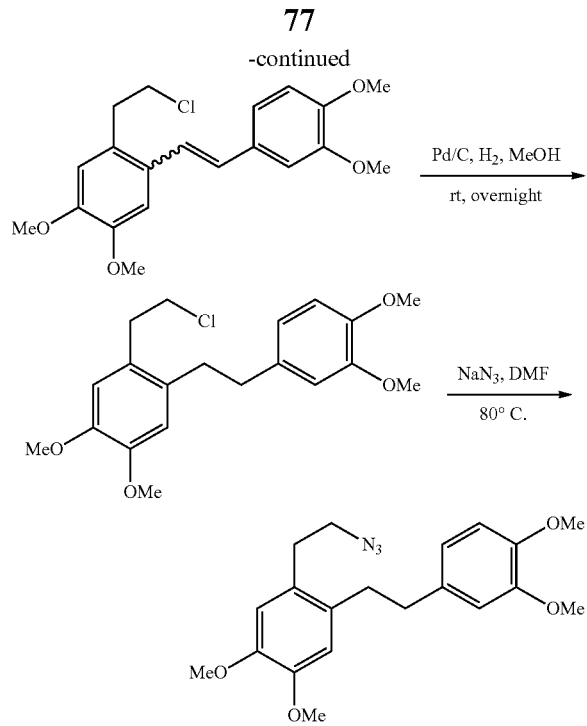

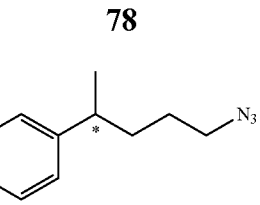

1-(2-chloroethyl)-2-(3,4-dimethoxystyryl)-4,5-dimethoxybenzene: Synthesized following the reported procedures (J. D. Harling, et al., *Tetrahedron*, 1998, 54, 14905) from 2-(2-chloroethyl)-4,5-dimethoxybenzaldehyde (M. Yamato, et al., *Tetrahedron*, 1990, 46, 5909) and obtained as a pink solid (69%). $^1$H NMR (400 MHz, CDCl$_3$) δ 6.76 (s, 1H), 6.75-6.69 (m, 3H), 6.65 (s, 1H), 6.55 (s, 2H), 3.89 (s, 3H), 3.84 (s, 3H), 3.66 (s, 3H), 3.63 (t, J=7.4 Hz, 2H), 3.56 (s, 3H), 3.02 (t, J=7.4 Hz, 2H). $^{13}$C NMR (100 MHz, CDCl$_3$) δ 148.4, 148.2, 148.0, 130.9, 129.7, 129.6, 128.6, 126.6, 122.4, 113.4, 112.7, 111.7, 110.8, 100.1, 56.1, 56.0, 55.9, 55.6, 44.6, 36.9.

1-(2-chloroethyl)-2-(3,4-dimethoxyphenethyl)-4,5-dimethoxybenzene: Synthesized following the general procedure B and the desired product was obtained as a white solid (82%) after flash chromatography. $^1$H NMR (400 MHz, CDCl$_3$) δ 6.79 (d, J=8.1 Hz, 1H), 6.69 (dd, J=8.1, 2.0 Hz, 1H), 6.67 (s, 1H), 6.63 (s, 2H), 3.86 (s, 3H+3H), 3.83 (s, 3H), 3.82 (s, 3H), 3.56 (t, J=7.8 Hz, 1H), 2.96 (t, J=7.9 Hz, 1H), 2.88-2.77 (m, 4H). $^{13}$C NMR (100 MHz, CDCl$_3$) δ 145.0, 148.0, 147.6, 147.4, 134.2, 132.2, 128.0, 120.5, 113.1, 113.0, 112.1, 111.5, 56.2, 56.2, 56.1, 56.0, 44.7, 37.7, 36.0, 34.7. HRMS (ESI) m/z: [M+Na]$^+$ calcd. for [C$_{20}$H$_{25}$ClO$_4$Na]$^+$: 387.1334, found 387.1327.

1-(2-azidoethyl)-2-(3,4-dimethoxyphenethyl)-4,5-dimethoxybenzene: Synthesized following the second step in the general procedure A (the tosylate was replaced by alkyl chloride) and obtained as a white solid (93%). $^1$H NMR (400 MHz, CDCl$_3$) δ 6.79 (d, J=8.1 Hz, 1H), 6.69 (dd, J=8.3, 1.8 Hz, 1H), 6.66 (s, 1H), 6.63 (s, 1H), 6.61 (d, J=2.0 Hz, 1H), 3.86 (s, 3H), 3.86 (s, 3H), 3.82 (s, 3H+3H), 3.35 (t, J=7.5 Hz, 2H), 2.88-2.80 (m, 4H), 2.77 (t, J=7.5 Hz, 2H). $^{13}$C NMR (100 MHz, CDCl$_3$) δ 148.8, 147.7, 147.4, 147.3, 134.1, 132.0, 127.7, 120.4, 112.9, 112.8, 111.9, 111.3, 56.0, 56.0, 55.9, 55.8, 52.3, 37.6, 34.5, 31.8. HRMS (ESI) m/z: [M+Na]$^+$ calcd. for [C$_{20}$H$_{25}$N$_3$O$_4$Na]$^+$: 394.1737, found 394.1732.

1-(2-azidoethyl)-2-benzylbenzene (3p) and (S)-(5-azidopentan-2-yl)benzene (S-3p): Synthesized following the general procedure A from 4-phenylpentan-1-ol and (S)-4-phenylpentan-1-ol respectively (D. J. Weix, et al., *J. Am. Chem. Soc.*, 2000, 122, 10027) and obtained as a colorless oil (71% over two steps). $^1$H NMR (400 MHz, CDCl$_3$) δ 7.34-7.14 (m, 5H), 3.21 (t, J=6.8 Hz, 2H), 2.76-2.63 (m, 1H), 1.70-1.61 (m, 2H), 1.59-1.41 (m, 2H), 1.26 (d, J=6.9 Hz, 3H). $^{13}$C NMR (100 MHz, CDCl$_3$) δ 146.8, 128.5, 126.9, 126.1, 51.6, 39.7, 35.3, 27.1, 22.4. Data is consistent with literature values[5]. (S)-(5-azidopentan-2-yl)benzene was determined to be 98% ee by chiral HPLC analysis (CHIRALCEL OD-H, Hexanes, 0.9 mL/min, 210 nm, tr (minor)=11.4 min, tr (major)=12.1 min).

General Procedure for Catalytic C—H Amination:

Iron-Catalyzed Intramolecular C—H Amination of Alkyl Azides:

An oven-dried Schlenk tube was charged with organic alkyl azides (0.2 mmol, 1.0 equiv.), Boc$_2$O (2.0 equiv), iron catalyst $^t$Bu$_4$PcFe(py)$_2$ (1-3 mol %), and dry toluene (2.0 mL) under argon. The mixture was refluxed violently (130° C.) until full completion as detected by TLC (usually completion within 6 h). The reaction mixture was cooled to room temperature and concentrated, and the residue was purified by silica gel column chromatography to give the corresponding products. For reported products, their characterization are done by comparing with literature reported $^1$H NMR data. For new products, they were characterized by techniques such as $^1$H, $^{13}$C and $^{19}$F NMR spectroscopy and high-resolution mass spectrometry. This represents the standard condition. Yields below refer to isolated yields.

C—H amination products 1b to 31b, produced according to the standard condition above and their respective yields, were as follows:

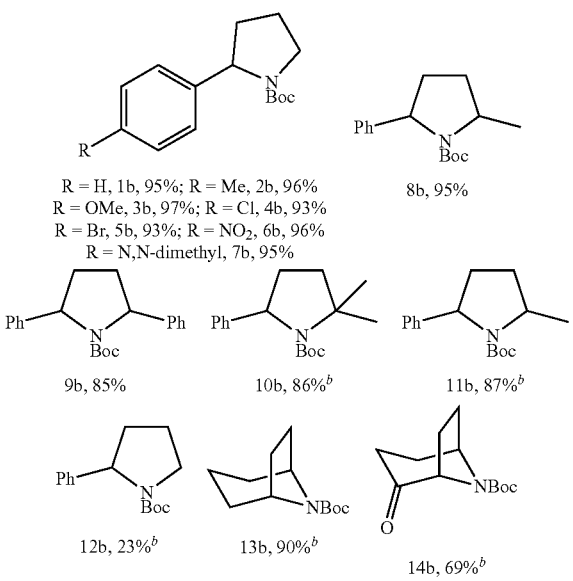

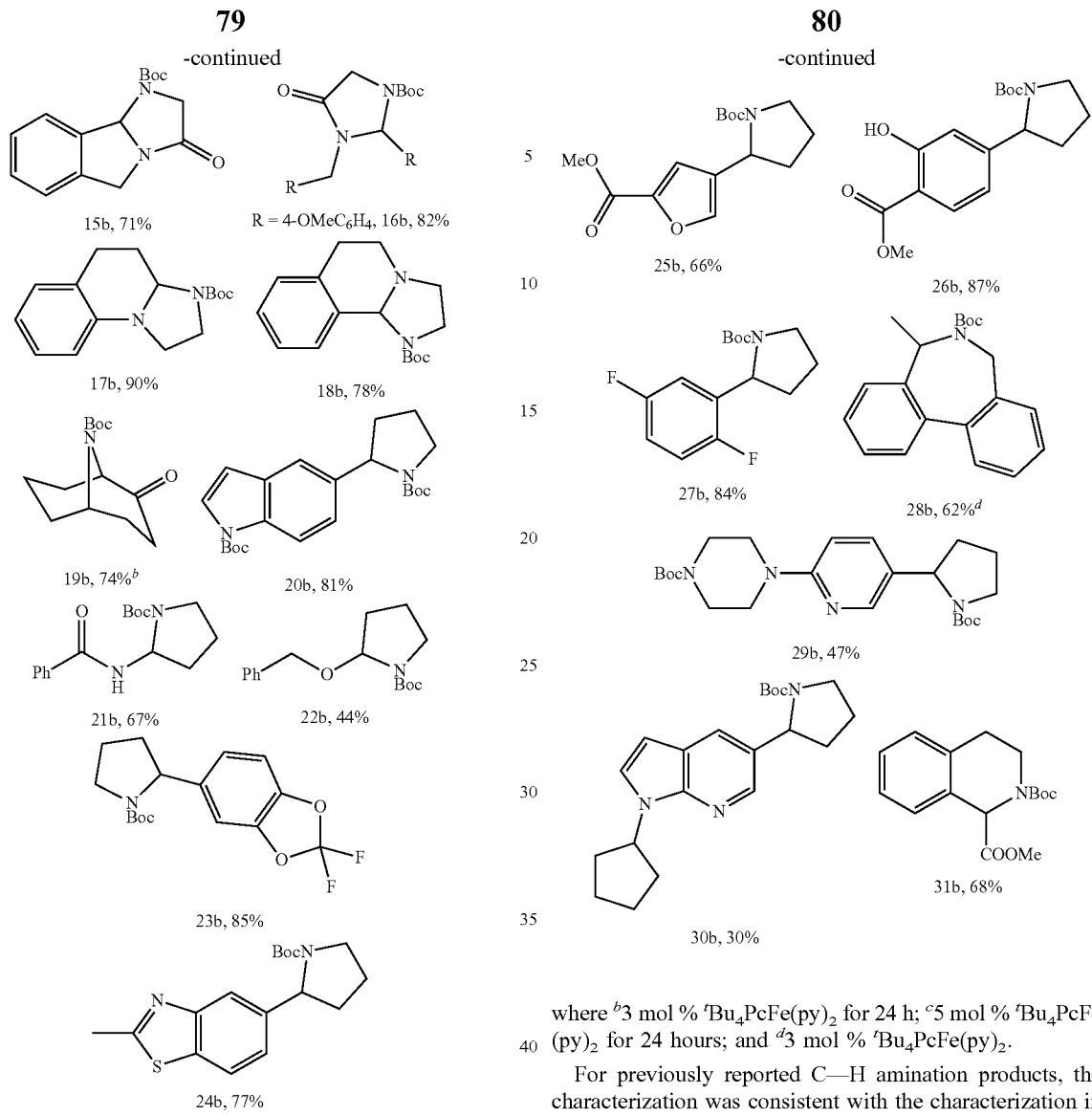
where [b]3 mol % 'Bu₄PcFe(py)₂ for 24 h; [c]5 mol % 'Bu₄PcFe(py)₂ for 24 hours; and [d]3 mol % 'Bu₄PcFe(py)₂.
For previously reported C—H amination products, the characterization was consistent with the characterization in the references listed in Table 2 below.
TABLE 2
| Reported products in the literature | |
|---|---|
| Compounds | References |
|  | E. T. Hennessy and T. A. Betley, *Science*, 2013, 340, 591 |

TABLE 2-continued

Reported products in the literature

| Compounds | References |
|---|---|
| 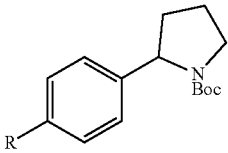<br>R = Me; R = OMe<br>R = N,N-dimethyl; R = F<br>R = Cl | J. Qin, Z. Zhou, T. Cui, M. Hemming and E. Meggers, *Chem. Sci.*, 2019, 10, 3202 |
| 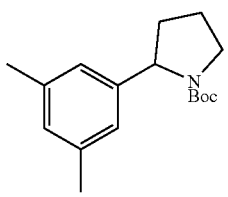 [SMILES: Cc1cc(C)cc(C2CCCN2C(=O)OC(C)(C)C)c1] | S. E. Denmark, W.-T. T. Chang, K. N. Houk and P. Liu, *J. Org. Chem.*, 2015, 80, 313 |
| 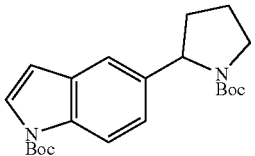 [SMILES: CC(C)(C)OC(=O)N1CCCC1c1ccc2c(ccn2C(=O)OC(C)(C)C)c1] | K. R. Campos, A. Klapars, J. H. Waldman, P. G. Dormer and C.-y. Chen, *J. Am. Chem. Soc.*, 2006, 128, 3538 |
| 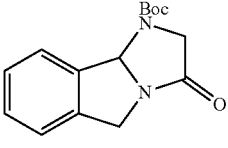 [SMILES: CC(C)(C)OC(=O)N1CC(=O)N2Cc3ccccc3C21]<br>R = 4-OMeC$_6$H$_4$ | Z. Zhou, S. Chen, J. Qin, X. Nie, X. Zheng, K. Harms, R. Riedel, K. N. Houk and E. Meggers, *Angew. Chem. Int. Ed.*, 2019, 58, 1088 |
| 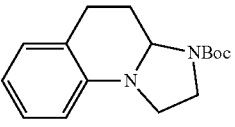 | Y.-D. Du, C.-Y. Zhou, W.-P. To, H.-X. Wang and C.-M. Che, *Chem. Sci.*, 2020, 11, 4680 |
| 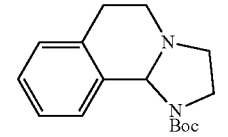 [SMILES: CC(C)(C)OC(=O)N1CCN2CCc3ccccc3C21] | |
| 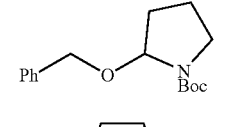 | A. R. Katritzky and Z. Luo, *Heterocycles*, 2001, 55, 1467 |
| 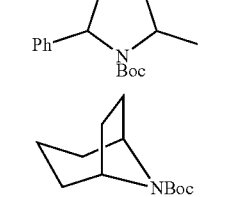 | K.-P. Shing, Y. Liu, B. Cao, X.-Y. Chang, T. You and C.-M. Che, *Angew. Chem. Int. Ed.*, 2018, 57, 11947 |

TABLE 2-continued

| Reported products in the literature | |
|---|---|
| Compounds | References |
| [structure: bicyclic ketone with NBoc] | |
| [structure: tetracyclic terpenoid with NBoc] | |
| [structure: 2,5-diphenyl-N-Boc-pyrrolidine] | D. A. Iovan, M. J. T. Wilding, Y. Baek, E. T. Hennessy and T. A. Betley, *Angew. Chem. Int. Ed.*, 2017, 56, 15599 |
| [structure: N-Boc bicyclic ketone] | Y.-D. Du, C.-Y. Zhou, W.-P. To, H.-X. Wang and C.-M. Che, *Chem. Sci.*, 2020, 11, 4680 |
| [structure: tetrahydroisoquinoline with NBoc and COOMe] | T. Mita, M. Sugawara, H. Hasegawa and Y. Sato, *J. Org. Chem.*, 2012, 77, 2159 |
| [structure: dibenzazepine with NBoc and methyl] | S. L. Pira, T. W. Wallace and J. P. Graham, *Org. Lett.*, 2009, 11, 1663 |
| [structure: 1-phenyl-N-Boc-tetrahydroisoquinoline] | X. Li and I. Coldham, *J. Am. Chem. Soc.*, 2014, 136, 5551 |
| [structure: tetrahydro-β-carboline with COOMe, NBoc, and benzodioxole] | S. Xiao, X.-X. Shi, J. Xing, J.-J. Yan, S.-L. Liu and W.-D. Lu, *Tetrahedron: Asymmetry*, 2009, 20, 2090 |

TABLE 2-continued

Reported products in the literature

| Compounds | References |
| --- | --- |
| 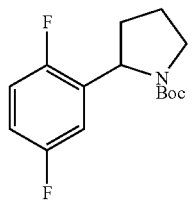 [SMILES: CC(C)(C)OC(=O)N1CCCC1c1cc(F)ccc1F] (structure with NBoc, OMe, MeO) | X. Li, D. Leonori, N. S. Sheikh and I. Coldham, *Chem.-Eur. J.*, 2013, 19, 7724 |
| 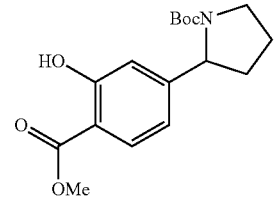 (structure with NBoc, OMe groups) | |

New C—H Amination Products Characterization Data:

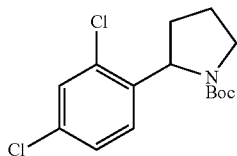 [SMILES: CC(C)(C)OC(=O)N1CCCC1c1ccc(Cl)cc1Cl]

tert-butyl 2-(2,5-difluorophenyl)pyrrolidine-1-carboxylate: $^1$H NMR (400 MHz, CDCl$_3$) δ 7.06-6.70 (m, 3H), 5.26-4.89 (br m, 1H), 3.73-3.40 (br m, 2H), 2.45-2.22 (m, 1H), 1.98-1.77 (m, 3H), 1.47 and 1.23 (br 2s, 3+6H). $^{13}$C NMR (125 MHz, CDCl$_3$) (minor rotamer was shown in the parentheses) δ 158.7 (d, J=242.3 Hz), 155.6 (d, J=240.5 Hz), 154.2 (154.3), 134.26-132.22 (m), 116.64-115.78 (m), 114.57-113.88 (m), 113.82-112.87 (m), 79.6 (79.7), 55.2 (55.3), 46.9 (47.2), 34.3 (33.3), 28.1 (28.5), 23.3 (23.6). $^{19}$F NMR (376 MHz, CDCl$_3$) δ −119.21 (d, J=17.9 Hz), −119.29−−119.38 (m), −124.63−−124.73 (m), −125.83 (d, J=17.8 Hz). HRMS (ESI) m/z: [M+Na]$^+$ calcd. for [C$_{15}$H$_{19}$F$_2$NO$_2$Na]$^+$: 306.1276, found 306.1277.

tert-butyl 2-(2,4-dichlorophenyl)pyrrolidine-1-carboxylate: $^1$H NMR (500 MHz, CDCl$_3$) δ 7.28 (s, 1H), 7.13 (d, J=8.0 Hz, 1H), 7.00 (dd, J=28.3, 8.2 Hz, 1H), 5.16-5.00 (br m, 1H), 3.60-3.39 (br m, 2H), 2.35-2.23 (m, 1H), 1.85-1.75 (m, 2H), 1.73-1.67 (m, 1H), 1.39 (br s, 3H), 1.14 (br s, 6H). $^{13}$C NMR (125 MHz, CDCl$_3$) (minor rotamer was shown in the parentheses)$^{13}$C NMR (126 MHz, Chloroform-d) δ 154.3, 140.9 (139.8), 132.6 (132.8), 132.4, 129.6 (129.6), 129.1, 126.9 (127.3), 79.6 (79.7), 58.3, 47.1 (47.5), 33.9 (32.7), 28.1 (28.5), 23.0 (23.3). HRMS (ESI) m/z: [M+Na]$^+$ calcd. for [C$_{15}$H$_{19}$Cl$_2$NO$_2$Na]$^+$ 338.0685, found: 338.0684.

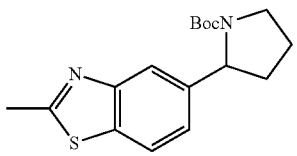 [SMILES: Cc1nc2cc(C3CCCN3C(=O)OC(C)(C)C)ccc2s1]

tert-butyl 2-(3-hydroxy-4-(methoxycarbonyl)phenyl)pyrrolidine-1-carboxylate: $^1$H NMR (500 MHz, CDCl$_3$) δ 10.66 (br s, 1H), 7.64 (s, 1H), 7.28 (d, J=7.8 Hz, 1H), 6.93 (d, J=8.6 Hz, 1H), 4.98-4.54 (br m, 1H), 3.94 (s, 3H), 3.69-3.47 (br m, 2H), 2.36-2.23 (br m, 1H), 1.94-1.76 (m, 3H), 1.50-1.15 (br m, 9H). $^{13}$C NMR (125 MHz, CDCl$_3$) (minor rotamer was shown in the parentheses) δ 170.5, 160.3, 154.6, 135.8 (134.8), 133.2 (133.0), 126.6, 117.3 (117.6), 111.8 (112.0), 79.4, 60.5 (60.0), 52.3 (52.2), 47.0 (47.3), 35.9 (34.8), 28.2 (28.4), 23.2 (23.5). HRMS (ESI) m/z: [M+H]$^+$ calcd. for [C$_{17}$H$_{24}$NO$_5$]$^+$: 322.1649, found 322.1647.

tert-butyl 2-(2-methylbenzo[d]thiazol-5-yl)pyrrolidine-1-carboxylate: $^1$H NMR (500 MHz, CDCl$_3$) δ 7.87 (d, J=8.4 Hz, 1H), 7.61 (s, 1H), 7.26 (d, J=8.5 Hz, 1H), 5.14-4.80 (br m, 1H), 3.74-3.51 (br m, 2H), 2.82 (s, 3H), 2.43-2.28 (br m, 1H), 1.98-1.83 (br m, 3H), 1.50-1.07 (br m, 9H). $^{13}$C NMR (125 MHz, CDCl$_3$) (minor rotamer was shown in the parentheses) δ 166.6 (166.4), 154.6, 152.2 (152.3), 142.2 (141.2), 135.7 (135.8), 124.0 (123.7), 122.0 (122.2), 118.0, 79.4, 61.3 (60.7), 47.1 (47.5), 36.2 (35.1), 28.2 (28.5), 23.2 (23.5), 20.13. HRMS (ESI) m/z: [M+H]⁺ calcd. for [C₁₇H₂₃N₂O₂S]⁺: 319.1475. found 319.1471.

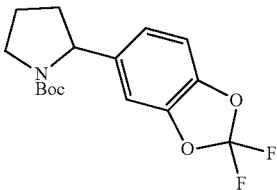 [SMILES: CC(C)(C)OC(=O)N1CCCC1c1ccc2c(c1)OC(F)(F)O2]

tert-butyl 2-(2,2-difluorobenzo[d][1,3]dioxol-5-yl)pyrrolidine-1-carboxylate: ¹H NMR (500 MHz, CDCl₃) δ 6.98 (d, J=8.4 Hz, 1H), 6.93-6.86 (m, 2H), 4.99-4.69 (br m, 1H), 3.70-3.45 (br m, 2H), 2.39-2.23 (br m, 1H), 1.93-1.83 (br m, 2H), 1.83-1.72 (br m, 1H), 1.52-1.17 (br m, 9H). ¹³C NMR (125 MHz, CDCl₃) (minor rotamer was shown in the parentheses) δ 154.4 (154.5), 143.8 (143.9), 142.3 (142.4), 141.7 (140.7), 131.65 (t, J=254.4 Hz), 120.4, 108.9 (109.2), 106.8, 79.6 (79.7), 60.98 (60.5), 47.1 (47.4), 36.1 (35.1), 28.2 (28.5), 23.0 (23.5). ¹⁹F NMR (376 MHz, CDCl₃) δ −49.88 (d, J=11.3 Hz), −50.17 (d, J=9.1 Hz). HRMS (ESI) m/z: [M+Na]⁺ calcd. for [C₁₆H₁₉F₂NO₄Na]⁺: 350.1174, found 350.1172.

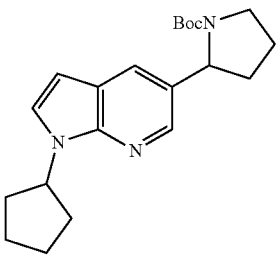 [SMILES: CC(C)(C)OC(=O)N1CCCC1c1cnc2c(ccn2C2CCCC2)c1]

tert-butyl 2-(1-cyclopentyl-1H-pyrrolo[2,3-b]pyridin-5-yl)pyrrolidine-1-carboxylate: ¹H NMR (500 MHz, CDCl₃) δ 8.17 (s, 1H), 7.68 (d, J=1.8 Hz, 1H), 7.29 (s, 1H), 6.41 (d, J=3.6 Hz, 1H), 5.32-5.22 (br m, 1H), 5.16-4.86 (br m, 1H), 3.74-3.48 (br m, 2H), 2.43-2.17 (br m, 3H), 1.93-1.73 (br m, 9H), 1.50-1.15 (br m, 9H). ¹³C NMR (125 MHz, CDCl₃) (minor rotamer was shown in the parentheses) δ 154.6 (154.6), 147.0, 141.2 (140.7), 132.2 (131.3), 125.4 (125.5), 125.3 (125.2), 120.3 (120.5), 99.2 (99.3), 79.3, 59.5 (59.1), 54.9, 47.0 (47.4), 36.3 (35.3), 32.9 (32.9), 28.3 (28.6), 24.1, 23.1 (23.4). HRMS (ESI) m/z: [M+H]⁺ calcd. for [C₂₁H₃₀N₃O₂]⁺: 356.2333, found 356.2329.

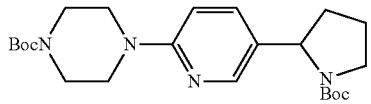

tert-butyl 4-(5-(1-(tert-butoxycarbonyl)pyrrolidin-2-yl)pyridin-2-yl)piperazine-1-carboxylate: ¹H NMR (500 MHz, CDCl₃) δ 8.04 (s, 1H), 7.33 (d, J=8.2 Hz, 1H), 6.61 (d, J=8.7 Hz, 1H), 4.93-4.62 (br m, 1H), 3.62-3.45 (m, 10H), 2.34-2.19 (br m, 1H), 1.94-1.83 (br m, 2H), 1.82-1.75 (br m, 1H), 1.48 (s, 9H), 1.47-1.22 (m, 9H). ¹³C NMR (125 MHz, CDCl₃) (minor rotamer was shown in the parentheses) δ 158.5, 154.8, 154.5, 145.7 (145.1), 135.1 (135.5), 130.0, (129.0), 106.9 (107.1), 79.9, 79.4, 58.6 (58.2), 46.9 (47.1), 45.4, 43.8, 42.9, 35.7 (34.5), 28.4 (28.3), 23.2 (23.5). HRMS (ESI) m/z: [M+H]⁺ calcd. for [C₂₃H₃₇N₄O₄]⁺: 433.2809, found 433.2807.

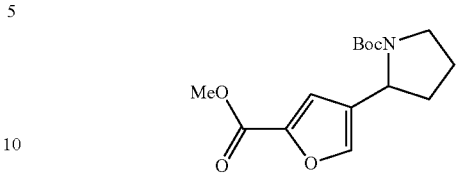

tert-butyl 2-(5-(methoxycarbonyl)furan-3-yl)pyrrolidine-1-carboxylate: ¹H NMR (500 MHz, CDCl₃) δ 7.49-7.36 (m, 1H), 7.08 (s, 1H), 5.00-4.65 (br m, 1H), 3.89 (s, 3H), 3.59-3.34 (br m, 2H), 2.30-2.12 (br m, 1H), 1.95-1.85 (m, 3H), 1.53-1.33 (br m, 9H). ¹³C NMR (125 MHz, CDCl₃) (minor rotamer was shown in the parentheses) δ 159.1, 154.3 (154.5), 144.6, 142.7 (142.9), 131.01 (130.4), 116.9 (117.2), 79.7, 52.8 (52.4), 51.9, 46.2 (46.5), 33.9 (32.6), 28.4, 23.2 (24.0). HRMS (ESI) m/z: [M+Na]⁺ calcd. for [C₁₅H₂₁NO₅Na]⁺: 318.1312, found 318.1310.

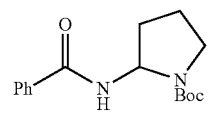

tert-butyl 2-benzamidopyrrolidine-1-carboxylate: ¹H NMR (400 MHz, CDCl₃) δ 7.58-7.32 (m, 5H), 5.67-5.03 (br, m, 2H), 3.82-3.24 (br, m, 2H), 2.42-1.70 (br, m, 4H), 1.54-1.26 (br, m, 9H). ¹³C NMR (125 MHz, CDCl₃) (minor rotamer was shown in the parentheses) δ 171.1 (170.0), 154.9 (153.2), 136.5, 130.1, 128.3, 127.3 (126.7), 79.7, 66.7 (66.1), 50.0 (45.9), 34.5 (30.7), 28.3, 24.5 (21.3). HRMS (ESI): m/z: M⁺ calcd. for C₁₆H₂₂N₂O₃: 290.1630, found 290.1629.

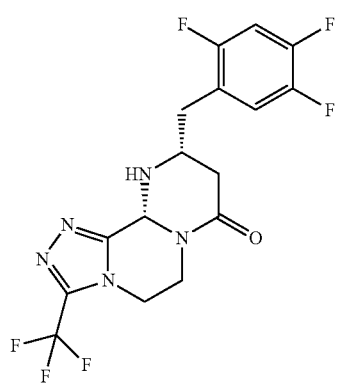 [SMILES: O=C1C[C@@H](Cc2cc(F)c(F)cc2F)N[C@H]2c3nnc(C(F)(F)F)n3CCN12]

(10R,11aR)-10-(2,4,5-trifluorobenzyl)-3-(trifluoromethyl)-5,6,9,10,11,11a-hexahydro-8H-[1,2,4]triazolo[3',4':3,4]pyrazino[1,2-a]pyrimidin-8-one: ¹H NMR (500 MHz, CDCl₃) δ 7.13 (q, J=8.8 Hz, 1H), 6.94 (q, J=9.4 Hz, 1H), 5.70 (d, J=8.6 Hz, 1H), 5.14 (dd, J=14.3, 4.0 Hz, 1H), 4.22 (dd, J=12.6, 4.0 Hz, 1H), 4.12 (td, J=12.3, 4.3 Hz, 1H), 3.55-3.43 (m, 1H), 3.18-3.08 (m, 1H), 2.99 (dd, J=13.9, 6.1 Hz, 1H), 2.92 (t, J=8.9 Hz, 1H), 2.85 (dd, J=13.9, 7.2 Hz, 1H), 2.48 (dd, J=17.2, 3.3 Hz, 1H), 2.25 (dd, J=17.2, 11.8 Hz, 1H). ¹³C NMR (125 MHz, CDCl₃) δ 167.0, 156.1 (ddd, J=244.6, 9.3, 2.4 Hz), 151.4, 149.1 (dt, J=250.8, 13.4 Hz), 146.7 (ddd, J=245.4, 12.5, 3.5 Hz), 143.9 (q, J=40.1 Hz), 120.2 (dt, J=18.3, 4.6 Hz), 119.0 (dd, J=19.0, 5.6 Hz), 118.0 (q, J=270.8 Hz), 105.7 (dd, J=28.6, 20.8 Hz), 67.1, 51.3, 43.4, 38.1, 35.9, 34.4. $^{19}$F NMR (376 MHz, CDCl$_3$) δ −63.16, −118.56−−118.68 (m), −134.84−−135.00 (m), −142.23−−142.44 (m).

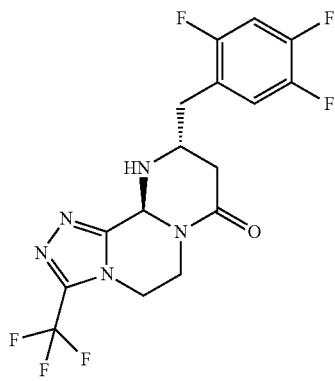 [SMILES: O=C1C[C@@H](Cc2cc(F)c(F)cc2F)N[C@@H]2c3nnc(C(F)(F)F)n3CCN12]

(10R,11aS)-10-(2,4,5-trifluorobenzyl)-3-(trifluoromethyl)-5,6,9,10,11,11a-hexahydro-8H-[1,2,4]triazolo[3',4':3,4]pyrazino[1,2-a]pyrimidin-8-one: $^1$H NMR (500 MHz, CDCl$_3$) δ 7.17 (q, J=8.7 Hz, 1H), 6.93 (td, J=9.6, 6.6 Hz, 1H), 5.77 (s, 1H), 5.06 (d, J=13.6 Hz, 1H), 4.15 (d, J=6.1 Hz, 2H), 3.32-3.19 (m, 2H), 2.95 (dd, J=14.1, 6.3 Hz, 1H), 2.82 (dd, J=14.1, 6.7 Hz, 1H), 2.73-2.52 (m, 1H), 2.43 (dd, J=16.7, 3.3 Hz, 1H), 2.27 (dd, J=16.7, 10.5 Hz, 1H). $^{13}$C NMR (125 MHz, CDCl$_3$) δ 167.7, 156.1 (ddd, J=244.1, 9.0, 2.4 Hz), 152.8, 149.1 (dt, J=251.3, 13.4 Hz), 146.8 (ddd, J=245.4, 12.2, 3.2 Hz), 144.8 (q, J=39.4 Hz), 119.8 (dt, J=18.3, 4.7 Hz), 118.9 (dd, J=19.2, 5.8 Hz), 118.0 (q, J=270.8 Hz), 105.7 (dd, J=28.7, 20.7 Hz), 66.8, 49.4, 42.8, 38.5, 38.3, 33.4. $^{19}$F NMR (376 MHz, CDCl$_3$) δ −63.43, −118.32−−118.44 (m), −134.68−−134.83 (m), −141.99−−142.29 (m). HRMS (ESI) m/z: [M+H]$^+$ calcd. for [C$_{16}$H$_{14}$F$_6$N$_5$O]$^+$: 406.1097, found 406.1088.

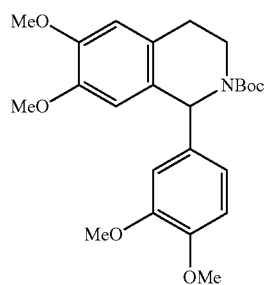

tert-butyl 1-(3,4-dimethoxyphenyl)-6,7-dimethoxy-3,4-dihydroisoquinoline-2(1H)-carboxylate (M. Kaur, et al., *Eur. J. Org. Chem.*, 2016, 2016, 4159): $^1$H NMR (500 MHz, CDCl$_3$) δ 6.96 (s, 1H), 6.74 (d, J=8.2 Hz, 1H), 6.68 (s, 1H), 6.61 (d, J=6.7 Hz, 1H), 6.52 (s, 1H), 6.43-6.05 (br m, 1H). 4.22-3.94 (br m, 1H), 3.89 (s, 3H), 3.85 (s, 3H), 3.83 (s, 3H), 3.77 (s, 3H), 3.12-3.00 (br m, 1H), 2.99-2.86 (br m, 1H), 2.73-2.60 (br m, 1H), 1.52 (s, 9H). $^{13}$C NMR (125 MHz, CDCl$_3$) (minor rotamer was shown in the parentheses) δ 154.7 (154.3), 148.7, 148.2, 147.9, 147.3, 135.8, 127.3, 127.1, 120.8, 111.8, 111.2, 111.1, 110.3, 79.9, 57.1, 55.9, 55.8, 55.8, 55.8, 37.8 (36.5), 28.6, 28.1. HRMS (ESI) m/z: [M+H]$^+$ calcd. for [C$_{24}$H$_{32}$NO$_6$]$^+$: 430.2224, found 430.2224.

Discussion:

As shown above, a variety of alkyl azides bearing different electronic properties and functional groups underwent C—H amination in moderate to excellent yields to afford compounds 1b to 31b.

Both electron-donating and withdrawing substituents on the phenyl moiety in the model substrate produced no difference, all leading to the benzylic C—H aminated pyrrolidine products in high yields (1b to 7b).

The aminations of secondary azides with benzylic, tertiary, secondary, and primary C—H bonds, afforded pyrrolidine products (9b to 12b) in 95% to 23% yields, indicating the following reactivity order: benzylic >3°~2°>1° C. H bonds.

When the alkyl azide precursor to product 13b was treated according to the system, tropane derivative 13b was synthesized in good yield when utilizing 3 mol % catalyst. Similarly, α-azido ketone precursors were well aminated to tropane analogues 14b and 19b in 69% and 74% yield, respectively.

Additionally, functional groups like indole, amide, ester, ether thiazole, furan and phenol were well tolerated in the catalytic system, yielding the corresponding pyrrolidines in yields of 30% to 87% (20b-31b).

A seven-member ring product of azepine analogue 28b was obtained using the instant method in 62% yield.

Notably intramolecular C—H aminations of alkyl azides producing products 20b to 31b have not, to the best of our knowledge and as of the filing of this application, been reported in previous works.

In summary, the iron (II)-phthalocyanine complex $^t$Bu$_4$PcFe(py)$_2$ is a useful catalyst which can be reacted with various alkyl azides featuring benzylic, tertiary, secondary, and primary C—H bonds to induce intramolecular C—H insertion and afford the ring-closure amination products in moderate to excellent yields.

Example 3: Large Scale C—H Amination of Azidocycloheptane

Procedure: An oven-dried Schlenk flask was charged with azidocycloheptane (3 mmol; 417 mg), Boc$_2$O (2.0 equiv), iron catalyst $^t$Bu$_4$PcFe(py)$_2$ (3 mol %), and dry toluene (15 mL) under argon. The reaction was refluxed violently (130° C.) for 2 days, and then cooled to room temperature and concentrated. The residue was purified by silica gel column chromatography to give the amination product. The characterization of this product was done by comparing with literature data (*Angew. Chem. Int. Ed.*, 2018, 57, 11947). The product (13b) was obtained in 90% ($^1$H NMR yield) and 61% isolated yield.

Discussion:

To demonstrate the synthetic application of the C—H amination reaction, a large-scale reaction was carried out to afford the tropane derivative in 90% $^1$H NMR yield by scaling up the catalytic by 15-fold. The tropane derivative had the following chemical structure:

Example 4: Synthesis of Complex Molecules and Late-Stage Functionalization of Active Pharmaceutical Ingredient Using C—H Amination Using the standard reaction conditions given in Example 2 above, the following natural product derivatives were formed at the specified yields, as follows:

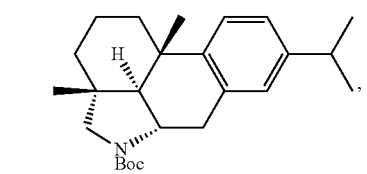

Leelamine derivative
3 mol % cat. for 24 h, 69%

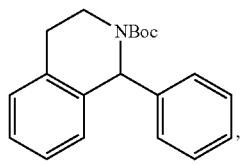

Vesicare derivative
90%

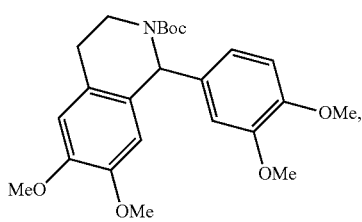

Cryptostyline II derivative
96%

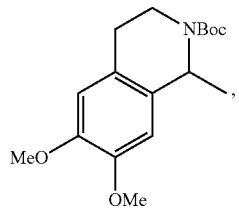

Salsolidine derivative
3 mol % cat., 35%

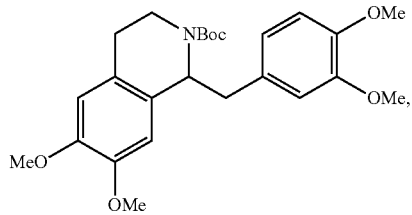

Norlaudanosine derivative
3 mol % cat., 50%

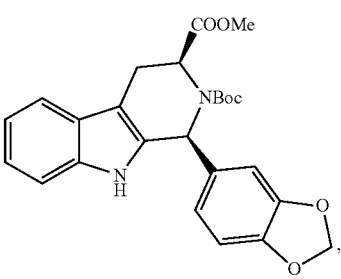

Tadalafil precursor
3 mol % cat., 70%

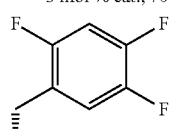

+

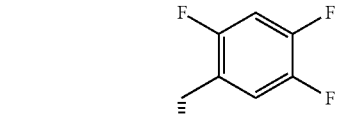

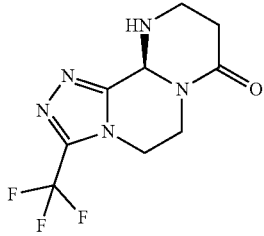

Sitagliptin derivatives
SC, 3 mol % catalyst, 24 h
58% + 23%

Discussion:

Characterization for the compounds above is given in Example 2 above. The application of the catalytic transformation was explored for late-stage functionalization of active pharmaceutical ingredients and the synthesis of alkaloids related natural products derivatives. For example, a cyclization reaction afforded 32b in 69% yield from an azide derived from leelamine. In another instance, N-Boc-1-phenyltetrahydroisoquinoline (33b), the key intermediate for preparation of vesicare (also called solifenacin), a potent antimuscarinic medication with urinary antispasmodic properties, was constructed using this method. Similarly, N-Boc-protected salsolidine (35b), norlaudanosine (36b) and cryptostyline II (34b) derivatives were also constructed from their azides precursors, albeit with less efficiency as compared to the former two molecules. Product 37b, which can be converted to tadalafil (cialis) in three steps (*Tetrahedron: Asymmetry*, 2009, 20, 2090), can be obtained from the azides derived from L-tryptophan. Lastly, late-stage amination of the drug molecule sitagliptin was realized from a derived azide precursor to afford 38b and 38b' where the structures of the corresponding products was confirmed by x-ray analysis, as shown in FIG. 1.

The above example demonstrates that the catalytic transformation using the iron (II)-phthalocyanine complex $^tBu_4PcFe(py)_2$ catalyst for C—H amination could also be successfully applied in the synthesis of natural product derivatives and late-stage functionalization of commercially available acyclic amines to gain the corresponding alkaloids.

Example 5: Comparison of Catalyst Performance for C—H Amination

Iron-dipyrrinato catalyst (1) was applied in intramolecular amination of $C(sp^3)$—H bonds of alkyl azides by Betley and co-workers in 2013. Other catalysts with different catalytic reactivities for amination of alkyl azides have also been developed by several groups. Some representative iron catalysts (1-4) are compared with the catalysis performance of $^tBu_4PcFe(py)_2$ (5). Table 3 provides the chemical structures of known catalysts.

TABLE 3

| Iron Catalysts | | |
|---|---|---|
| Catalysts | By | References |
| 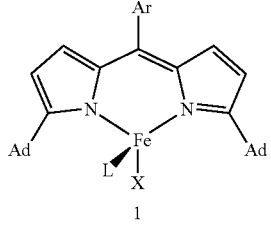 1 | Betley et al. | E. T. Hennessy, T. A. Betley, *Science* 2013, 340, 591; and D. A. Iovan, M. J. T. Wilding, Y. Baek, E. T. Hennessy, T. A. Betley, *Angew. Chem. Int. Ed.* 2017, 56, 15599 |
| 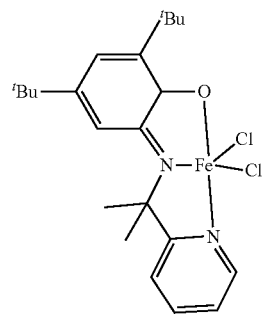 2 | van der Vlugt et al. | B. Bagh, D. L. J. Broere, V. Sinha, P. F. Kuijpers, N. P. van Leest, B. de Bruin, S. Demeshko, M. A. Siegler, J. I. van der Vlugt, *J. Am. Chem. Soc.* 2017, 139, 5117 |
| 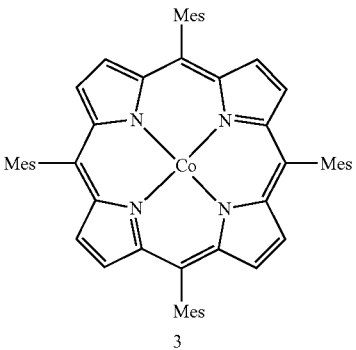 3 | de Bruin et al. | P. F. Kuijpers, M. J. Tiekink, W. B. Breukelaar, D. L. J. Broere, N. P. van Leest, J. I. van der Vlugt, J. N. H. Reek and B. de Bruin, *Chem. Eur. J.* 2017, 23, 7945 |

TABLE 3-continued

Iron Catalysts

| Catalysts | By | References |
|---|---|---|
| 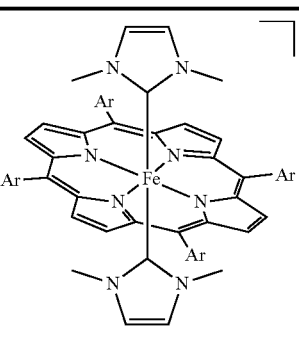<br>4 | Che et al. | K.-P. Shing, Y. Liu, B. Cao, X.-Y. Chang, T. You, C.-M. Che, *Angew. Chem. Int. Ed.* 2018, 57, 11947. |
| 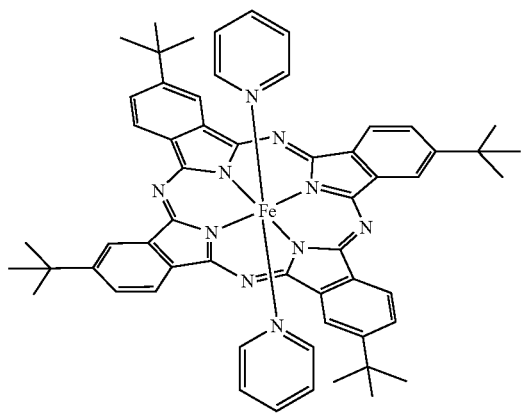<br>$^t$Bu$_4$PcFe(py)$_2$, 5 | Instant Work and Examples | J. Metz, O. Schneider, M. Hanack, *Inorg. Chem.* 1984, 23, 1065; (b) G. Zanotti, S. Notarantonio, A. M. Paoletti, G. Pennesi, G. Rossi *J. Porphyrins Phthalocyanines* 2011, 15: 748. |

Compounds 12b, 10b, 13b, and 32b, as discussed in above examples, were synthesized using the C—H amination method using catalysts 1-5. The compounds are shown below.

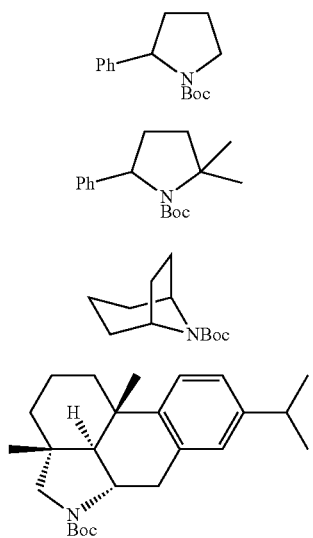

TABLE 4

Reaction Results

| | Yields (%) | | | |
|---|---|---|---|---|
| Catalyst | Product 12b | Product 10b | Product 13b | Product 32b |
| 1<br>(20 mol %-1 equiv., 65° C.) | 57-93 | 70 | — | — |
| 2<br>(5 mol %, 100° C.) | 60 | — | — | — |
| 3<br>(4 mol %, 100° C.) | 89 | — | — | — |
| 4<br>(10 mol %, 115° C.) | 74 | 93 | 63 | 78 |
| 5<br>(1 mol %, 130° C.) | 95 | 86<br>(3 mol %) | 90<br>(3 mol %) | 69<br>(3 mol %) |

"—"denotes not performed.

As shown in Table 4, catalyst 5 ($^t$Bu$_4$PcFe(py)$_2$) showed good catalytic reactivity to obtain corresponding products 12b, 10b, 13b and 32b with lower catalyst loading and/or higher yields, as compared to catalysts 1-4.

Example 6: Mechanistic Studies

In order to gain an understanding of the mechanism of the catalytic amination process described herein, three reactions were performed as shown in Scheme 2 below.

Scheme 2.

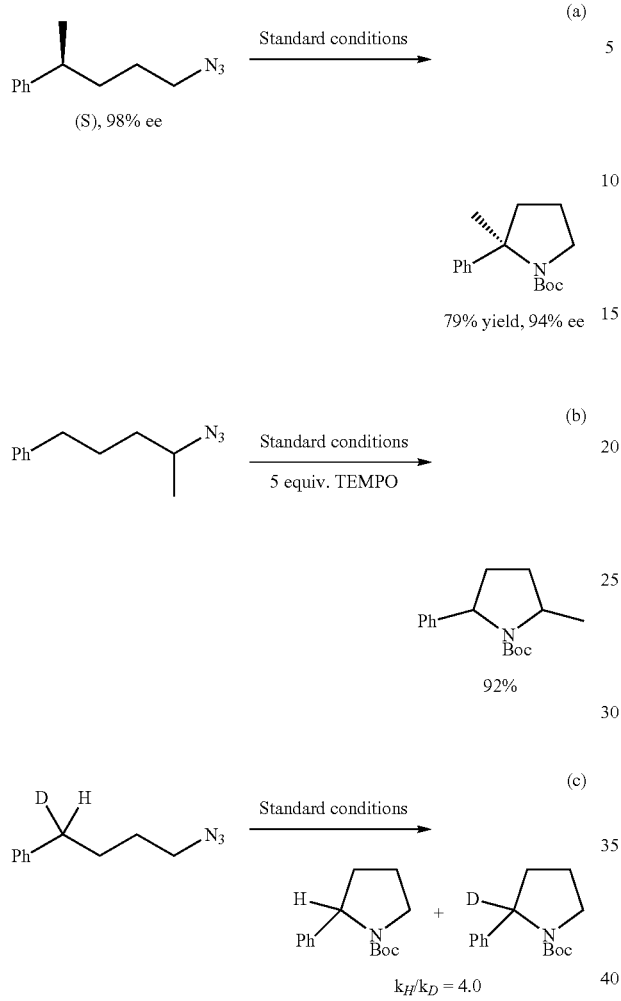

The standard conditions were those of Example 2 above. In (a) (S)-(5-azidopentan-2-yl)benzene (98% ee) was treated according to the method and resulted in tert-butyl (R)-2-methyl-2-phenylpyrrolidine-1-carboxylate (94% ee) with retention of stereochemistry, which is similar with the reported result (*Science*, 2013, 340, 591).

In (b) adding 5 equivalents of TEMPO to the catalytic system did not shut down the amination reaction, and no radical trapped products were detected.

In (c), the intramolecular kinetic isotope effect (KIE) value was calculated as 4.0 when monodeuterated azide 1-azido-4-deutero-4-phenylbutane was subjected to standard conditions, which was smaller than the reported data 5.1 at 60° C. by Betley (*Science*, 2013, 340, 591) but larger than the value 1.9 at 115° C. by Che's group (*Angew. Chem. Int. Ed.*, 2018, 57, 11947). This was indicative that a stepwise mechanism was involved in the catalytic reaction.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of C—H bond amination comprising the steps of:
   (a) forming a reaction mixture comprising an alkyl azide, an iron(II)-phthalocyanine catalyst, and one or more solvents in a reaction vessel; and
   (b) heating the reaction mixture to a temperature of at least about 100° C. sufficient to induce a direct intramolecular C—H bond amination of the alkyl azide;
   wherein the iron(II)-phthalocyanine catalyst is defined according to any one of Formulae A, B, C, or D:

Formula A

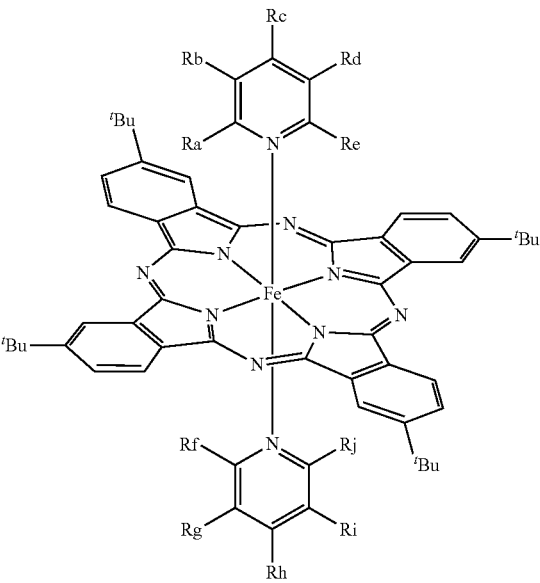

Formula B

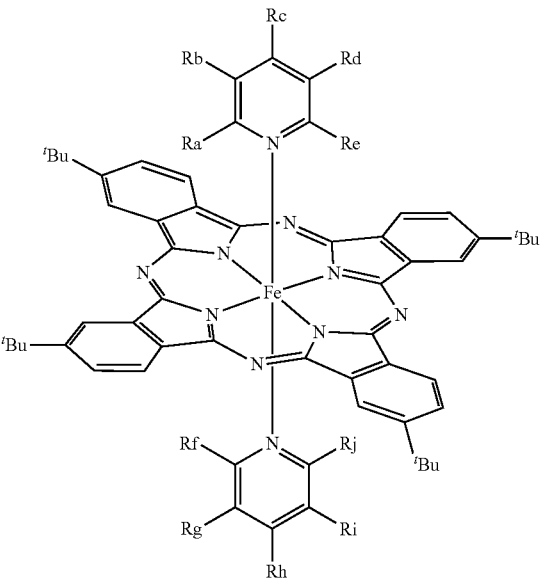

-continued

Formula C

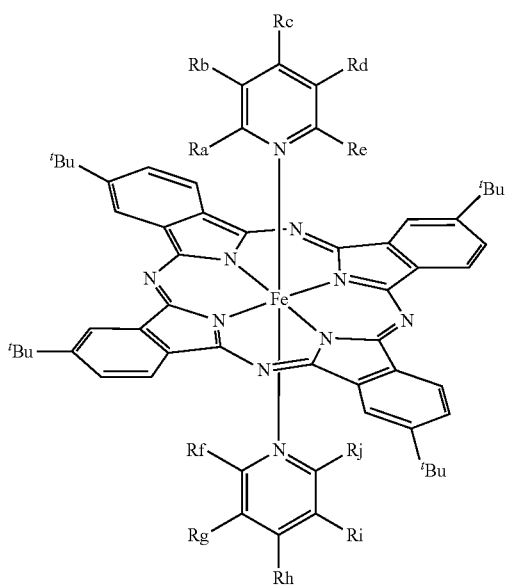

Formula D

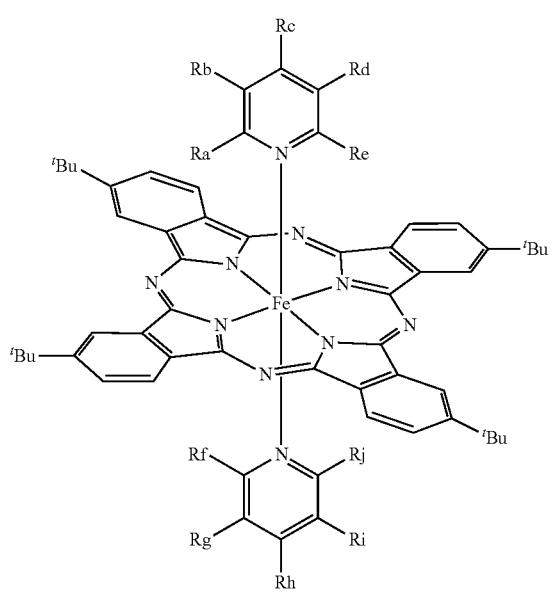

wherein Ra, Rb, Rc, Rd, Re, Rf, Rg, Rh, Ri, and Rj in each of Formulae A-D are each independently selected from the group consisting of a hydrogen; halogen group; a $C_2$-$C_5$ linear or branched alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group, such as methoxy, ethoxy, propoxy, or butoxy; an aryl group; a heteroaryl group; a benzyl group; an acyl group; an ester group; a carbonyl group; a carboxylate group; an amino group; an amide group; and a nitro group.

2. The method of claim 1, wherein Ra and Rb, Rb and Rc, Rc and Rd, or Rd and Re can together form a saturated, unsaturated, or aromatic, optionally substituted ring having a total of from 5 to 10 carbon atoms; and/or Rf and Rg, Rg and Rh, Rh and Ri, or Ri and Rj can together form a saturated, unsaturated, or aromatic, optionally substituted ring having a total of from 5 to 10 carbon atoms.

3. The method of claim 1, wherein the iron(II)-phthalocyanine catalyst of Formula A has one of the following chemical structures:

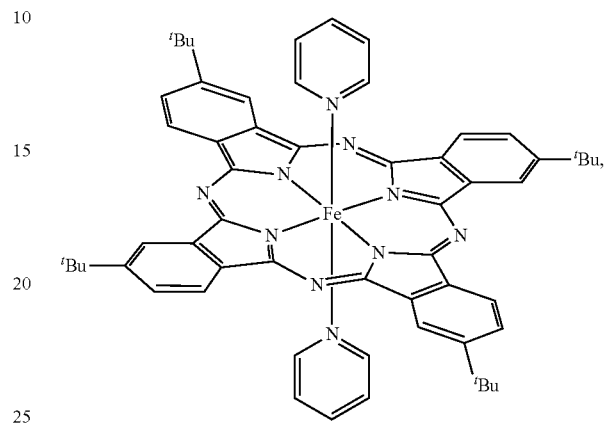

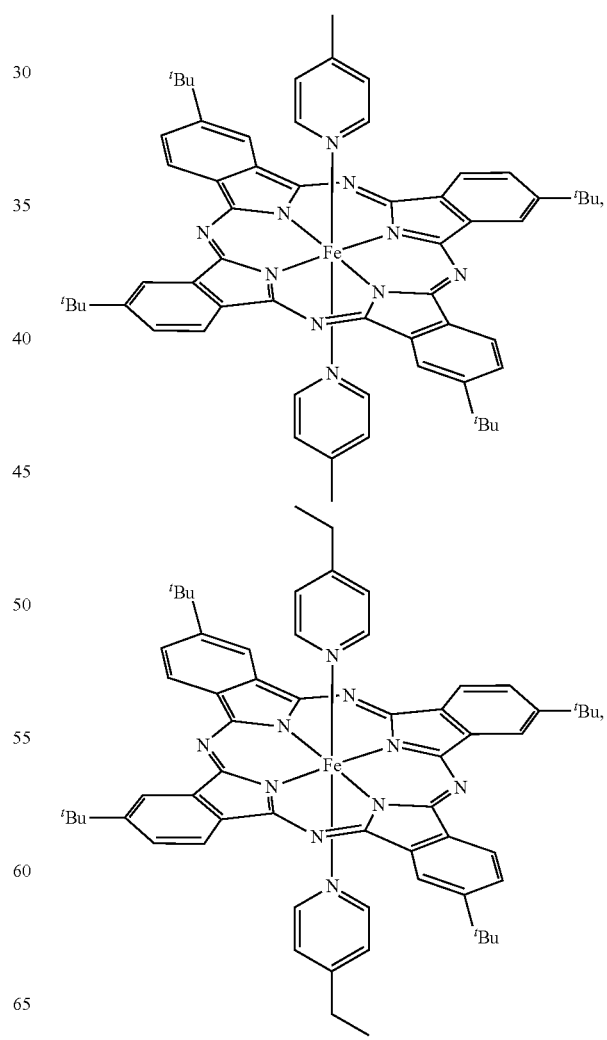

101
-continued
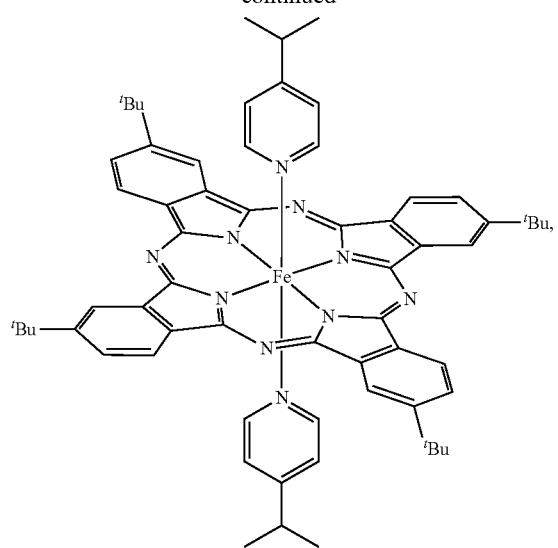
102
-continued
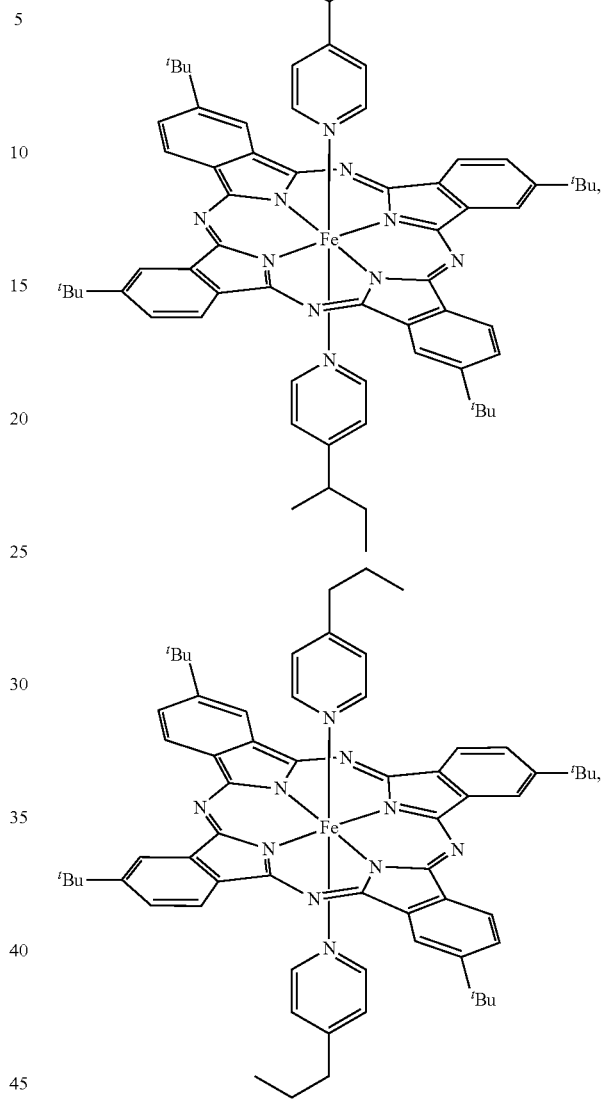
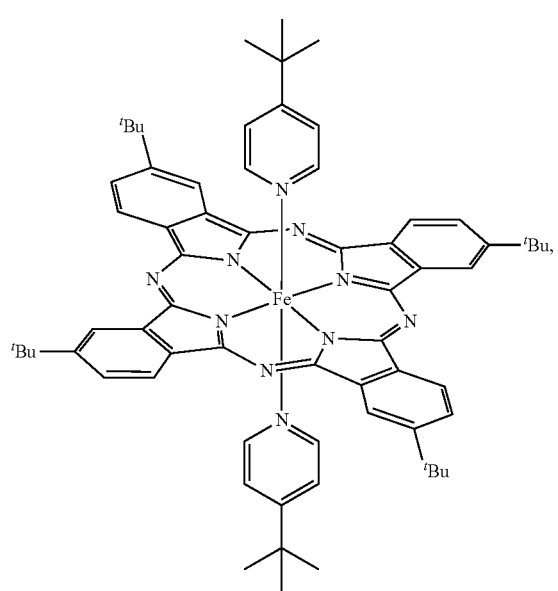
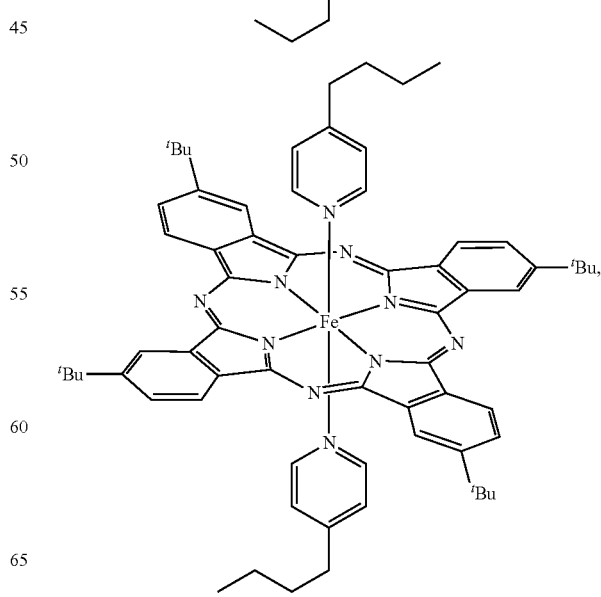

103
-continued
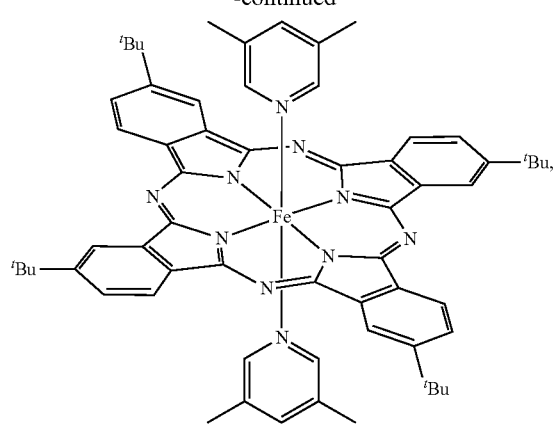
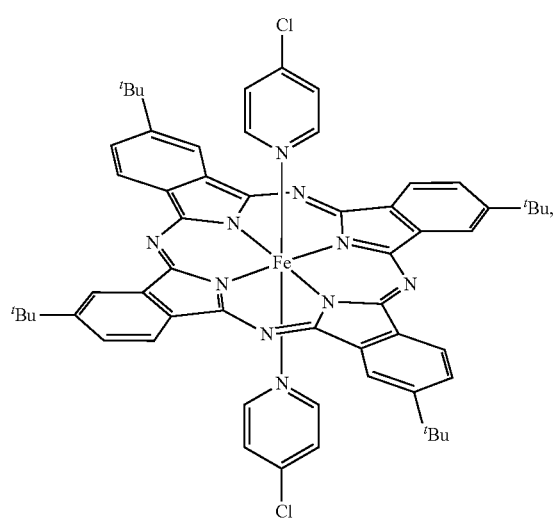
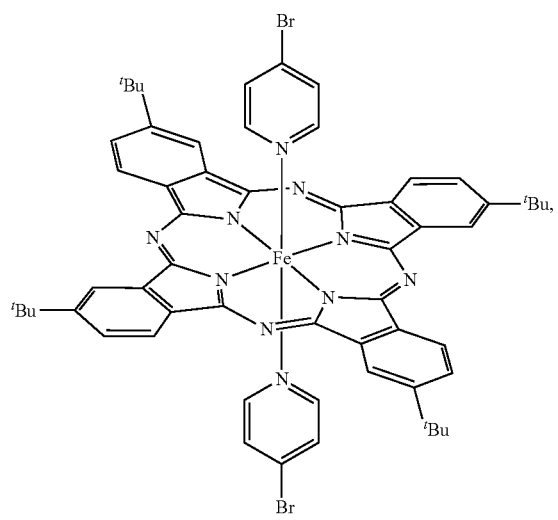
104
-continued
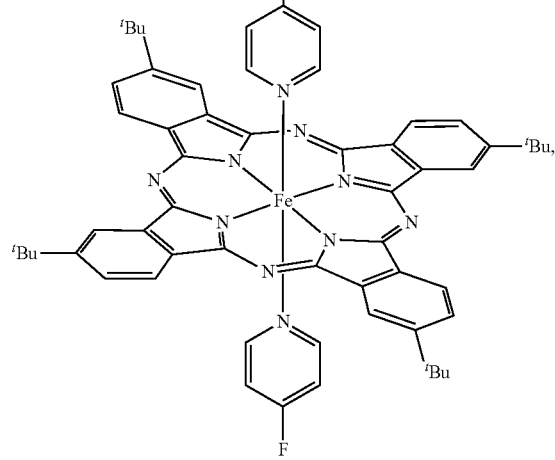
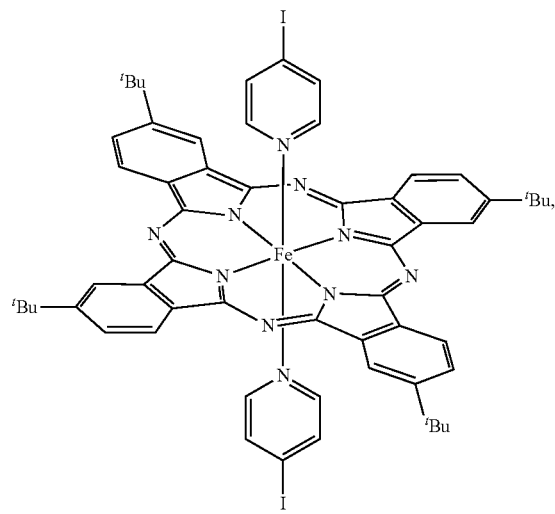
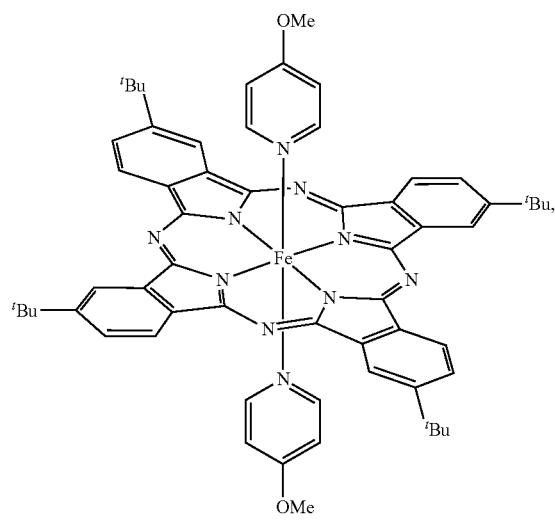

105
-continued
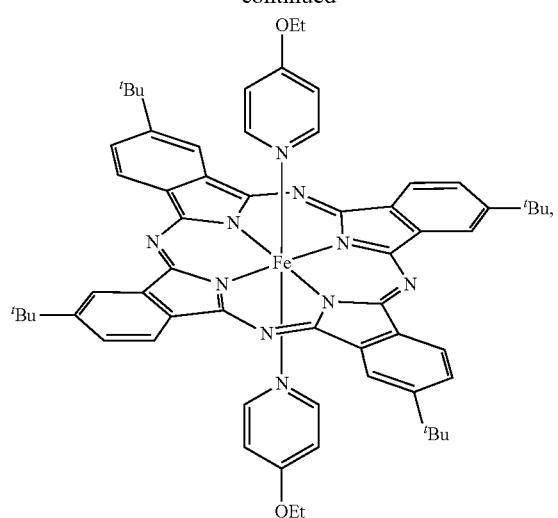
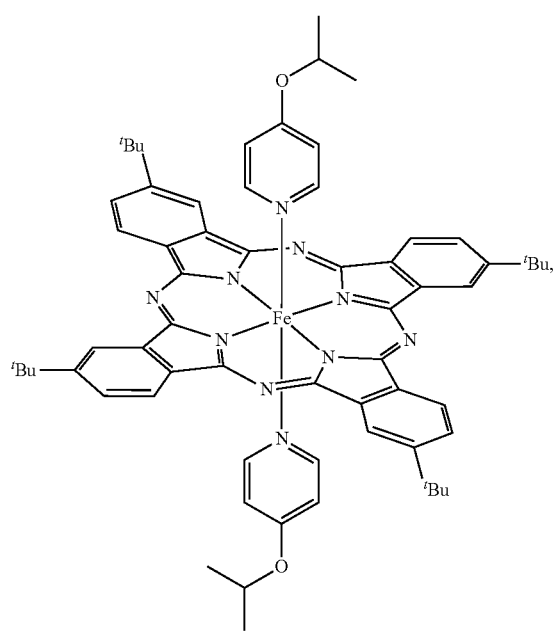
106
-continued
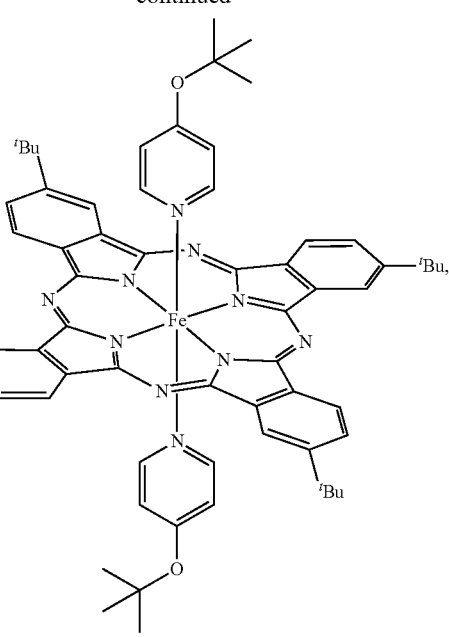
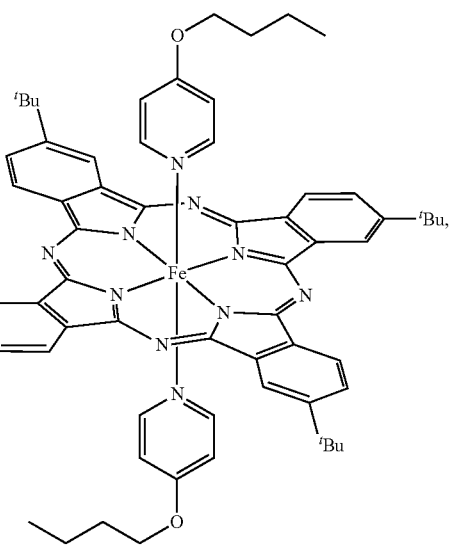
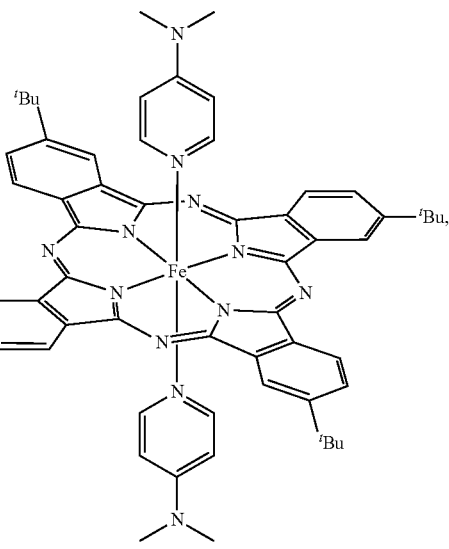

107
-continued
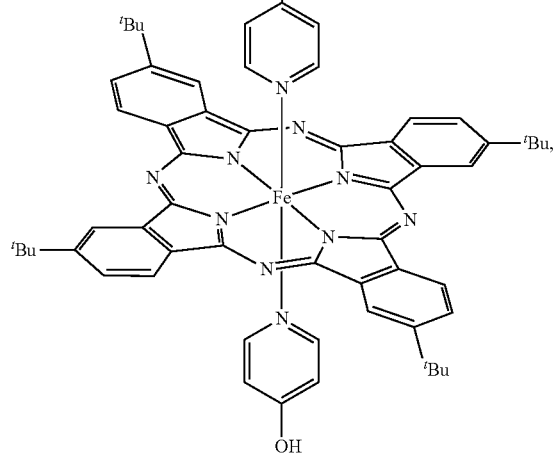
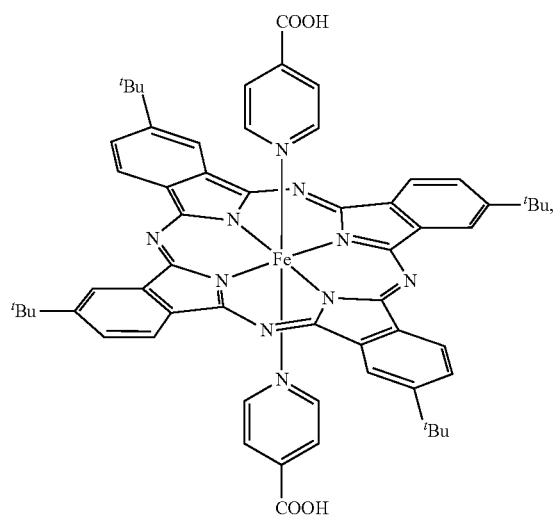
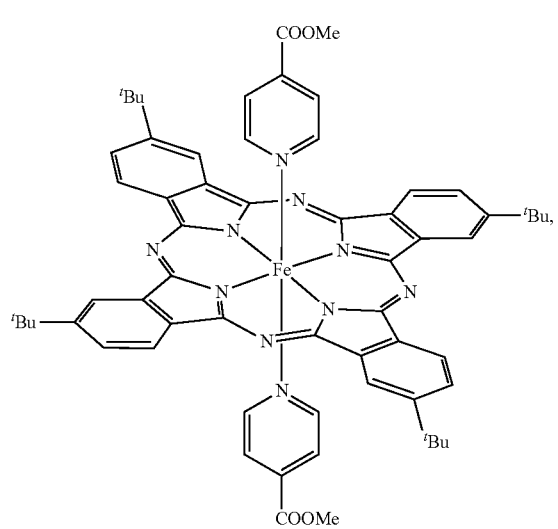
108
-continued
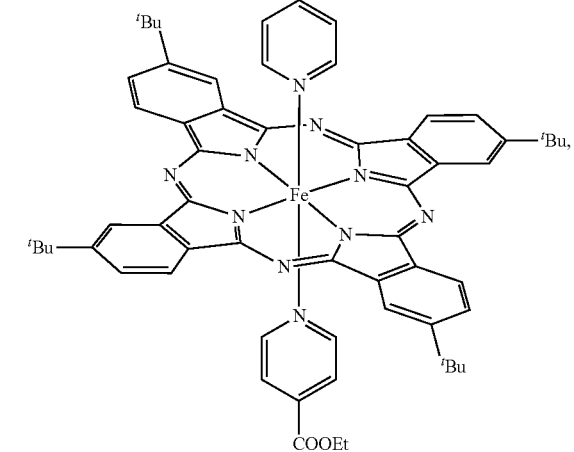
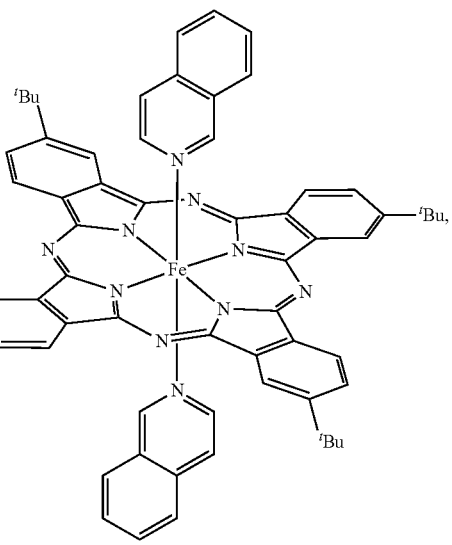
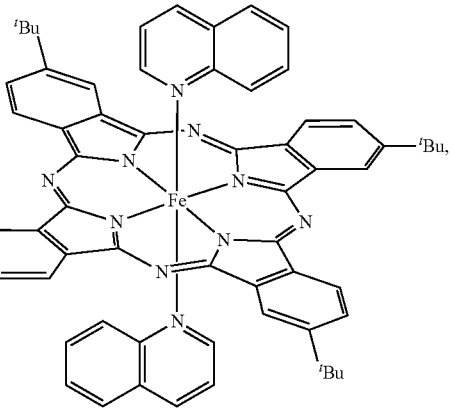
and isomers thereof.
4. The method of claim 1, wherein the iron(II)-phthalocyanine catalyst is:

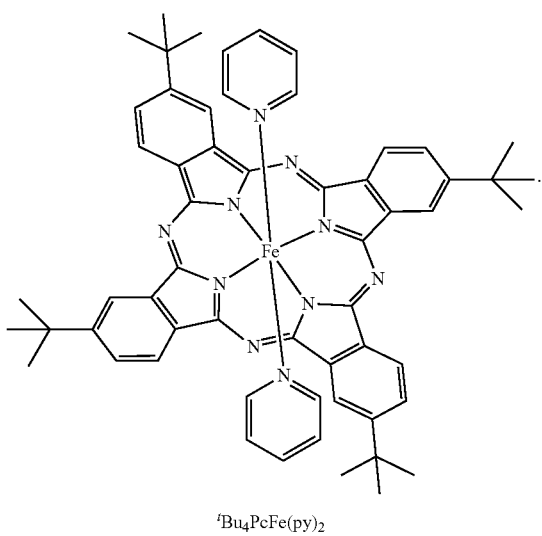

$^t$Bu$_4$PcFe(py)$_2$

5. The method of claim 1, wherein the iron(II)-phthalocyanine catalyst is present in the reaction mixture at an amount of about 0.1 to 5 mol % of the amount of the alkyl azide present; or at an amount of at least about 1, 2, 3, 4, or 5 mol % of the amount of the alkyl azide present.

6. The method of claim 1, wherein the reaction mixture is heated to a temperature in a range of between about 105° C. to about 130° C.

7. The method of claim 1, wherein the reaction mixture further comprises at least one reagent for protecting amine groups.

8. The method of claim 7, wherein the at least one reagent for protecting amine groups is selected from the group consisting of fluorenylmethoxycarbonyl (Fmoc) and di-tert-butyl dicarbonate (Boc$_2$O).

9. The method of claim 1, wherein the alkyl azide comprises a benzylic, tertiary, secondary, or primary C—H bond.

10. The method of claim 1, wherein the alkyl azide has a chemical structure according to Formula I, as follows:

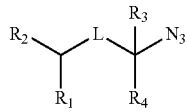

Formula I wherein R$_1$, R$_2$, R$_3$, and R$_4$ are each independently selected from the group consisting of hydrogen; halogen group; a C$_2$-C$_5$ alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group; a heteroaryl group; a benzyl group; an oxo (=O) group; an acyl group; an ester group; a carbonyl group; a carboxylate group; an amino group; an amide group; and a nitro group; and wherein L is a substituted or unsubstituted alkyl radical chain having 3, 4, 5, 6, 7, or 8 carbons, the chain optionally interrupted by at least one heteroatom; and, when substituted, substituents on each of the carbons present are independently selected from the group consisting of hydrogen; halogen group; a C$_2$-C$_5$ alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group; a heteroaryl group; a benzyl group; an oxo (=O) group; an acyl group; an ester group; a carbonyl group; a carboxylate group; an amino group; an amide group; and a nitro group.

11. The method of claim 10, wherein R$_1$ and R$_2$ together form a saturated, unsaturated, or aromatic, optionally substituted ring having a total of from 5 to 10 carbon atoms.

12. The method of claim 10, wherein R$_3$ and R$_4$ together form a saturated, unsaturated, or aromatic, optionally substituted ring having a total of from 5 to 10 carbon atoms.

13. The method of claim 10, wherein R$_1$ and R$_3$ or R$_4$ are linked by a saturated, unsaturated, optionally substituted alkyl chain having a total of from 3 to 10 carbon atoms.

14. The method of claim 10, wherein R$_2$ and R$_3$ or R$_4$ are linked by a saturated, unsaturated, optionally substituted alkyl chain having a total of from 3 to 10 carbon atoms.

15. The method of claim 1, wherein the alkyl azide has a chemical structure of Formula II, as follows:

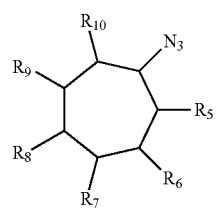

Formula II wherein R$_1$, R$_2$, R$_3$, R$_4$, R$_5$, R$_6$, R$_7$, R$_8$, R$_9$, and R$_{10}$ are each independently selected from the group consisting of hydrogen; halogen group; a C$_2$-C$_5$ alkyl group, such as a methyl, ethyl, propyl, butyl, or pentyl group; alkenyl group; alkynyl group; cycloalkyl group; cycloalkenyl group; cycloalkynyl group; a hydroxyl group; an alkoxy group; an aryl group; a heteroaryl group; a phenyl group; a benzyl group; an oxo (=O) group; an acyl group; an ester group; a carbonyl group; a carboxylate group; an amino group; an amide group; and a nitro group.

16. The method of claim 1, wherein the direct intramolecular C—H bond amination of the alkyl azide affords a ring-closure amination product of the alkyl azide.

17. The method of claim 16, wherein the ring-closure amination product has a chemical structure shown below:

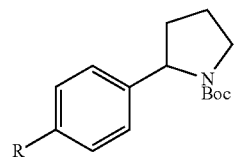

wherein R is H, Me, OMe, Cl, Br, F, NO$_2$, or N,N-dimethyl;

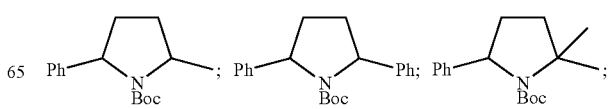

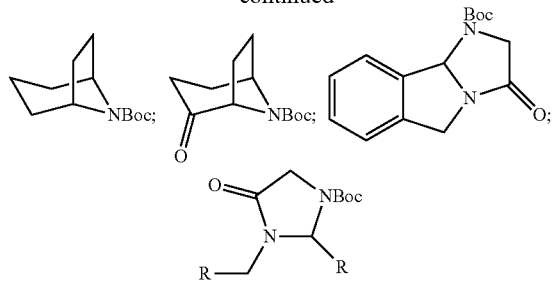
wherein each R is 4-OMeC$_6$H$_4$;
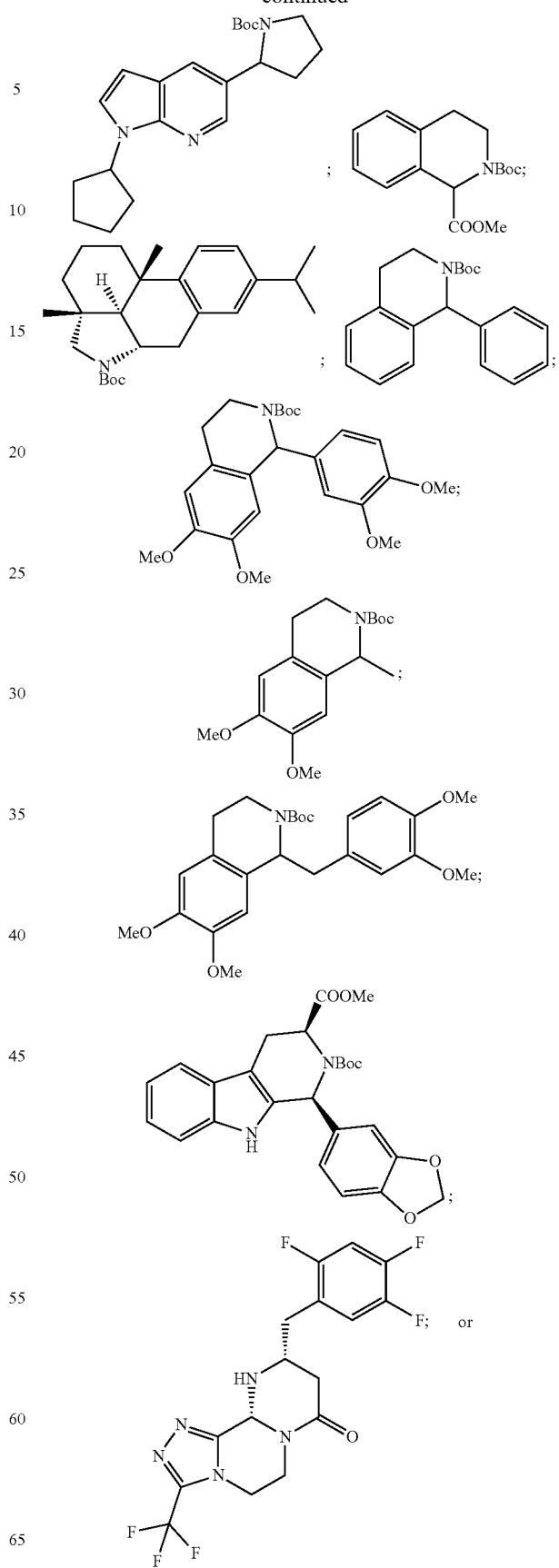

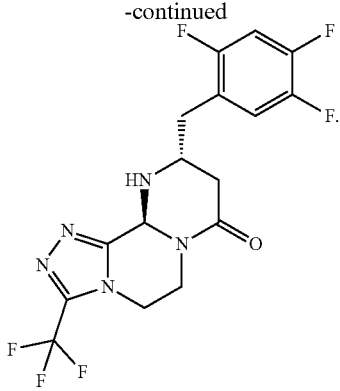

UNITED STATES PATENT AND TRADEMARK OFFICE
CERTIFICATE OF CORRECTION

| | |
|---|---|
| PATENT NO. | : 12,098,126 B2 |
| APPLICATION NO. | : 17/821314 |
| DATED | : September 24, 2024 |
| INVENTOR(S) | : Chi-Ming Che and Tingjie You |

It is certified that error appears in the above-identified patent and that said Letters Patent is hereby corrected as shown below:

In the Claims

Claim 1, Column 99, Lines 55-56, delete: ", such as a methyl, ethyl, propyl, butyl, or pentyl group".
Claim 1, Column 99, Lines 59-60, delete: ", such as methoxy, ethoxy, propoxy, or butoxy".
Claim 10, Column 109, Lines 54-55, delete: ", such as a methyl, ethyl, propyl, butyl, or pentyl group".
Claim 10, Column 110, Lines 1-2, delete: ", such as a methyl, ethyl, propyl, butyl, or pentyl group".
Claim 13, Column 110, Line 16, replace: "saturated," with --saturated or--.
Claim 14, Column 110, Line 19, replace: "saturated," with --saturated or--.
Claim 15, Column 110, Lines 37-38, delete: ", such as a methyl, ethyl, propyl, butyl, or pentyl group".

Signed and Sealed this
Third Day of December, 2024

Katherine Kelly Vidal
*Director of the United States Patent and Trademark Office*